United States Patent
Walcheck et al.

(10) Patent No.: US 12,269,887 B2
(45) Date of Patent: Apr. 8, 2025

(54) ANTI-CANINE CD16 POLYPEPTIDES, ANTI-CANINE CD64 POLYPEPTIDES, COMPOSITIONS INCLUDING SAME, AND METHODS OF USING

(71) Applicant: REGENTS OF THE UNIVERSITY OF MINNESOTA, Minneapolis, MN (US)

(72) Inventors: Bruce K. Walcheck, Lino Lakes, MN (US); Jianming Wu, Plymouth, MN (US); Daniel A. Vallera, Richfield, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 18/099,448

(22) Filed: Jan. 20, 2023

(65) Prior Publication Data
US 2023/0227561 A1    Jul. 20, 2023

Related U.S. Application Data

(60) Provisional application No. 63/301,143, filed on Jan. 20, 2022.

(51) Int. Cl.
C07K 16/28    (2006.01)
G01N 33/58    (2006.01)

(52) U.S. Cl.
CPC ......... *C07K 16/283* (2013.01); *G01N 33/582* (2013.01); *C07K 2317/31* (2013.01); *C07K 2317/55* (2013.01); *C07K 2317/565* (2013.01); *C07K 2317/622* (2013.01)

(58) Field of Classification Search
CPC .............. C07K 16/283; C07K 2317/31; C07K 2317/55; C07K 2317/565; C07K 2317/622; G01N 33/582
See application file for complete search history.

(56) References Cited

U.S. PATENT DOCUMENTS

| | | | |
|---|---|---|---|
| 5,234,809 | A | 8/1993 | Boom et al. |
| 7,776,616 | B2 | 8/2010 | Heath et al. |
| 7,957,913 | B2 | 6/2011 | Chinitz et al. |
| 9,012,208 | B2 | 4/2015 | Selden et al. |
| 9,994,641 | B2 * | 6/2018 | Sonoda ............. C07K 16/2881 |
| 2011/0091483 | A1 | 4/2011 | Beall |
| 2016/0194399 | A1 | 7/2016 | Irving et al. |
| 2018/0079811 | A1 * | 3/2018 | Molloy ................... A61P 37/02 |

OTHER PUBLICATIONS

Winkler et al. (2000) Journal of Immunology 165(8): 4505-4514. (Year: 2000).*
Edwards et al. (2003) Journal of Molecular Biology 334(1): 103-118. (Year: 2003).*
Lloyd et al. (2009) Protein Engineering, Design and Selection 22(3): 159-168. (Year: 2009).*
Schroeder and Cavacini. (2010) Journal of Allergy and Clinical Immunology 125(2, Suppl.2): S41-S52. (Year: 2010).*
Sela-Culang et al. (2013) Frontiers in Immunology 4: 302. (Year: 2013).*
Bannas et al. (2017) Frontiers in Immunology 8: 1603 (Year: 2017).*
Jovčevska and Muyldermans (2020) BioDrugs 34:11-16. (Year: 2020).*
Alderson et al., Clinical cancer therapy by NK cells via antibody-dependent cell-mediated cytotoxicity. J Biomed Biotechnol 2011, 379123 (2011).
Bergeron et al., Comparative functional characterization of canine IgG subclasses. Vet Immunol Immunopathol 157, 31-41 (2014).
Bibeau et al., Impact of FcgammaRIIa-FcgammaRIIIa polymorphisms and KRAS mutations on the clinical outcome of patients with metastatic colorectal cancer treated with cetuximab plus irinotecan. J Clin Oncol 27, 1122-1129 (2009).
Binyamin et al., Blocking NK cell inhibitory self-recognition promotes antibody-dependent cellular cytotoxicity in a model of anti-lymphoma therapy. J Immunol 180, 6392-6401 (2008).
Bjorkstrom et al., Elevated numbers of Fc gamma RIIIA+ (CD16+) effector CD8 T cells with NK cell-like function in chronic hepatitis C virus infection. J Immunol 181, 4219-4228 (2008).
Blazquez-Moreno et al., Transmembrane features governing Fc receptor CD16A assembly with CD16A signaling adaptor molecules. Proc Natl Acad Sci U S A 114, E5645-E5654 (2017).
Bruhns, Properties of mouse and human IgG receptors and their contribution to disease models. Blood 119, 5640-5649 (2012).
Canter et al., Radiotherapy enhances natural killer cell cytotoxicity and localization in pre-clinical canine sarcomas and first-in-dog clinical trial. J Immunother Cancer 5, 98 (2017).
Cartron et al., Therapeutic activity of humanized anti-CD20 monoclonal antibody and polymorphism in IgG Fc receptor FcgammaRIIIa gene. Blood 99, 754-758 (2002).
Dixon et al., Engineering Anti-Tumor Monoclonal Antibodies and Fc Receptors to Enhance ADCC by Human NK Cells. Cancers (Basel) 13, (2021).
Donaghy et al., Identification of canine IgG and its subclasses, IgG1, IgG2, IgG3 and IgG4, by immunofixation and commercially available antisera. Vet Immunol Immunopathol 221, 110014 (2020).
Felices et al., IL-15 super-agonist (ALT-803) enhances natural killer (NK) cell function against ovarian cancer. Gynecol Oncol 145, 453-461 (2017).

(Continued)

*Primary Examiner* — Brad Duffy
*Assistant Examiner* — Elizabeth A Shupe
(74) *Attorney, Agent, or Firm* — Mueting Raasch Group

(57) ABSTRACT

An anti-canine CD16 polypeptide generally includes a CDR region of SEQ ID NO:5, a CDR region of SEQ ID NO:9, or a functional variant of either CDR region. An anti-canine CD64 polypeptide generally includes a CDR region of SEQ ID NO:13, a CDR region of SEQ ID NO:17, or a functional variant of either CDR region. The anti-canine CD16 polypeptide and anti-canine CD64 polypeptide may be incorporated into a therapeutic compound, a multispecific compound, a targeted imaging compound, or a capture assay device.

20 Claims, 16 Drawing Sheets
Specification includes a Sequence Listing.

(56) References Cited

OTHER PUBLICATIONS

Foltz et al., NCR1 Expression Identifies Canine Natural Killer Cell Subsets with Phenotypic Similarity to Human Natural Killer Cells. Front Immunol 7, 521 (2016).
Gauthier et al., Natural Killer cells and monoclonal antibodies: Two partners for successful antibody dependent cytotoxicity against tumor cells. Crit Rev Oncol Hematol 160, 103261 (2021).
Gibbons et al., Phenotypic heterogeneity of peripheral monocytes in healthy dogs. Vet Immunol Immunopathol 190, 26-30 (2017).
Gingrich et al., Characterization and Potential Applications of Dog Natural Killer Cells in Cancer Immunotherapy. J Clin Med 8, (2019).
Gingrich et al., Comparative Immunogenomics of Canine Natural Killer Cells as Immunotherapy Target. Front Immunol 12, 670309 (2021).
Graves et al., Development and characterization of a canine-specific anti-CD94 (KLRD-1) monoclonal antibody. Vet Immunol Immunopathol 211, 10-18 (2019).
Groh et al., Human lymphocytes bearing T cell receptor gamma/delta are phenotypically diverse and evenly distributed throughout the lymphoid system. J Exp Med 169, 1277-1294 (1989).
Grondahl-Rosado et al., NCR1+ cells in dogs show phenotypic characteristics of natural killer cells. Vet Res Commun 39, 19-30 (2015).
Grondahl-Rosado et al., NCR1 is an activating receptor expressed on a subset of canine NK cells. Vet Immunol Immunopathol 177, 7-15 (2016).
Hintz et al., Simultaneous Engagement of Tumor and Stroma Targeting Antibodies by Engineered NK-92 Cells Expressing CD64 Controls Prostate Cancer Growth. Cancer Immunol Res 9, 1270-1282 (2021).
Huang et al., CD5-low expression lymphocytes in canine peripheral blood show characteristics of natural killer cells. J Leukoc Biol 84, 1501-1510 (2008).
Huizinga et al., Binding characteristics of dimeric IgG subclass complexes to human neutrophils. J Immunol 142, 2359-2364 (1989).
Jing et al., Identification of an ADAM17 cleavage region in human CD16 (FcgammaRIII) and the engineering of a non-cleavable version of the receptor in NK cells. PLoS One 10, e0121788 (2015).
Jones et al., Generation of a new gamma delta T cell-specific monoclonal antibody (GD3.5). Biochemical comparisons of GD3.5 antigen with the previously described Workshop Cluster 1 (WC1) family. J Immunol 156, 3772-3779 (1996).
Judge et al., Blood and tissue biomarker analysis in dogs with osteosarcoma treated with palliative radiation and intra-tumoral autologous natural killer cell transfer. PLoS One 15, e0224775 (2020).
Kim et al., Canine non-B, non-T NK lymphocytes have a potential antibody-dependent cellular cytotoxicity function against antibody-coated tumor cells. BMC Vet Res 15, 339 (2019).
Kisseberth et al., Adoptive Natural Killer Cell Immunotherapy for Canine Osteosarcoma. Front Vet Sci 8, 672361 (2021).
Koene et al., Fc gammaRIIIa-158V/F polymorphism influences the binding of IgG by natural killer cell Fc gammaRIIIa, independently of the Fc gammaRIIIa-48L/R/H phenotype. Blood 90, 1109-1114 (1997).
Lajoie et al., ADAM17-mediated shedding of FcgammaRIIIA on human NK cells: identification of the cleavage site and relationship with activation. J Immunol 192, 741-751 (2014).
Lanier et al., Human NKR-P1A. A disulfide-linked homodimer of the C-type lectin superfamily expressed by a subset of NK and T lymphocytes. J Immunol 153, 2417-2428 (1994).
Lanier et al., Functional properties of a unique subset of cytotoxic CD3+ T lymphocytes that express Fc receptors for IgG (CD16/Leu-11 antigen). J Exp Med 162, 2089-2106 (1985).
Lanier et al., Co-association of CD3 zeta with a receptor (CD16) for IgG Fc on human natural killer cells. Nature 342, 803-805 (1989).
Lee et al., Comparison of Phenotypic and Functional Characteristics Between Canine Non-B, Non-T Natural Killer Lymphocytes and CD3(+)CD5(dim)CD21(−) Cytotoxic Large Granular Lymphocytes. Front Immunol 9, 841 (2018).
Letourneur et al., Characterization of the family of dimers associated with Fc receptors (Fc epsilon RI and Fc gamma RIII). J Immunol 147, 2652-2656 (1991).
Liu et al., Development of Effective Therapeutics Targeting HER3 for Cancer Treatment. Biol Proced Online 21, 5 (2019).
Loveday et al., Effect of Inactivation Methods on SARS-CoV-2 Virion Protein and Structure. Viruses 13, (2021).
Miller et al., Expansion and homing of adoptively transferred human natural killer cells in immunodeficient mice varies with product preparation and in vivo cytokine administration: implications for clinical therapy. Biol Blood Marrow Transplant 20, 1252-1257 (2014).
Miller et al., "Natural Killer Cells in Cancer Immunotherapy" *Annu Rev Cancer Biol*, 3:77-103 (Mar. 2019).
Mishra et al., Blocking ADAM17 Function with a Monoclonal Antibody Improves Sepsis Survival in a Murine Model of Polymicrobial Sepsis. Int J Mol Sci 21, (2020).
Mishra et al., Anti-ADAM17 monoclonal antibody MEDI3622 increases IFNgamma production by human NK cells in the presence of antibody-bound tumor cells. Cancer Immunol Immunother 67, 1407-1416 (2018).
Mizuno et al., Generation of a canine anti-canine CD20 antibody for canine lymphoma treatment. Sci Rep 10, 11476 (2020).
Mizuno et al., Development of a cell line-based assay to measure the antibody-dependent cellular cytotoxicity of a canine therapeutic antibody. Vet Immunol Immunopathol 240, 110315 (2021).
Musolino et al., Immunoglobulin G fragment C receptor polymorphisms and clinical efficacy of trastuzumab-based therapy in patients with HER-2/neu-positive metastatic breast cancer. J Clin Oncol 26, 1789-1796 (2008).
Nimmerjahn et al., FcgammaRIV: a novel FcR with distinct IgG subclass specificity. Immunity 23, 41-51 (2005).
Nimmerjahn et al., Fcgamma receptors: old friends and new family members. Immunity 24, 19-28 (2006).
Nimmerjahn et al., Fcgamma receptors as regulators of immune responses. Nat Rev Immunol 8, 34-47 (2008).
Otani et al., CD56 is expressed exclusively on CD3+ T lymphocytes in canine peripheral blood. J Vet Med Sci 64, 441-444 (2002).
Park et al., The anti-canine distemper virus activities of ex vivo-expanded canine natural killer cells. Vet Microbiol 176, 239-249 (2015).
Patel et al., Multiple Variables at the Leukocyte Cell Surface Impact Fc gamma Receptor-Dependent Mechanisms. Front Immunol 10, 223 (2019).
Pomeroy et al., A Genetically Engineered Primary Human Natural Killer Cell Platform for Cancer Immunotherapy. Mol Ther 28, 52-63 (2020).
Ravetch et al., Alternative membrane forms of Fc gamma RIII(CD16) on human natural killer cells and neutrophils. Cell type-specific expression of two genes that differ in single nucleotide substitutions. J Exp Med 170, 481-497 (1989).
Rios-Doria et al., A Monoclonal Antibody to ADAM17 Inhibits Tumor Growth by Inhibiting EGFR and Non-EGFR-Mediated Pathways. Mol Cancer Ther 14, 1637-1649 (2015).
Romee et al., NK cell CD16 surface expression and function is regulated by a disintegrin and metalloprotease-17 (ADAM17). Blood 121, 3599-3608 (2013).
Selvaraj et al., The major Fc receptor in blood has a phosphatidylinositol anchor and is deficient in paroxysmal nocturnal haemoglobinuria. Nature 333, 565-567 (1988).
Snyder et al., Expression of a Recombinant High Affinity IgG Fc Receptor by Engineered NK Cells as a Docking Platform for Therapeutic mAbs to Target Cancer Cells. Front Immunol 9, 2873 (2018).
Snyder et al., Ectodomain shedding by ADAM17 (a disintegrin and metalloproteinase 17) in canine neutrophils. Vet Immunol Immunopathol 231, 110162 (2021).
Tatusova et al., BLAST 2 Sequences, a new tool for comparing protein and nucleotide sequences. FEMS Microbiol Lett 174, 247-250 (1999).

(56) References Cited

OTHER PUBLICATIONS

Tuohy et al., Association of Canine Osteosarcoma and Monocyte Phenotype and Chemotactic Function. J Vet Intern Med 30, 1167-1178 (2016).
Vitale et al., Effect of tumor cells and tumor microenvironment on NK-cell function. Eur J Immunol 44, 1582-1592 (2014).
Walcheck et al., The monoclonal antibody CHO-131 binds to a core 2 O-glycan terminated with sialyl-Lewis x, which is a functional glycan ligand for P-selectin. Blood 99, 4063-4069 (2002).
Walcheck et al., iNK-CD64/16A cells: a promising approach for ADCC? Expert Opin Biol Ther 19, 1229-1232 (2019).
Wang et al., ADAM17 cleaves CD16b (FcgammaRIIIb) in human neutrophils. Biochim Biophys Acta 1833, 680-685 (2013).
Wu et al., A novel polymorphism of FcgammaRIIIa (CD16) alters receptor function and predisposes to autoimmune disease. J Clin Invest 100, 1059-1070 (1997).
Wu et al., Role of ADAM17 as a regulatory checkpoint of CD16A in NK cells and as a potential target for cancer immunotherapy. J Leukoc Biol 105, 1297-1303 (2019).
Yamamoto et al., A novel bispecific single-chain antibody for ADAM17 and CD3 induces T-cell-mediated lysis of prostate cancer cells. Biochem J 445, 135-144 (2012).
Ye et al., The development of Nanosota-1 as anti-SARS-CoV-2 nanobody drug candidates. Elife 10, (2021).
Zahavi et al., Enhancing antibody-dependent cell-mediated cytotoxicity: a strategy for improving antibody-based immunotherapy. Antib Ther 1, 7-12 (2018).
Zahavi et al., Monoclonal Antibodies in Cancer Therapy. Antibodies (Basel) 9, (2020).
Zhu et al., Pluripotent stem cell-derived NK cells with high-affinity noncleavable CD16a mediate improved antitumor activity. Blood 135, 399-410 (2020).
Zidovetzki et al., Transmembrane domains in the functions of Fc receptors. Biophys Chem 100, 555-575 (2003).
PCT International Application No. PCT/US2022/033820 filed Jun. 16, 2022, International Search Report and Written Opinion, mailed on Nov. 15, 2022, 15 pages.

* cited by examiner (A)

(B)

(A)

(B)

(A)

(B)

(A)

(B)

SEQUENCE LISTING

```
Sequence total quantity: 57
SEQ ID NO: 1               moltype = AA   length = 254
FEATURE                    Location/Qualifiers
source                     1..254
                           mol_type = protein
                           organism = Homo sapiens
SEQUENCE: 1
MWQLLLPTAL LLLVSAGMRT EDLPKAVVFL EPQWYRVLEK DSVTLKCQGA YSPEDNSTQW    60
FHNESLISSQ ASSYFIDAAT VDDSGEYRCQ TNLSTLSDPV QLEVHIGWLL LQAPRWVFKE   120
EDPIHLRCHS WKNTALHKVT YLQNGKGRKY FHHNSDFYIP KATLKDSGSY FCRGLFGSKN   180
VSSETVNITI TQGLAVSTIS SFFPPGYQVS FCLVMVLLFA VDTGLYFSVK TNIRSSTRDW   240
KDHKFKWRKD PQDK                                                    254

SEQ ID NO: 2               moltype = AA   length = 248
FEATURE                    Location/Qualifiers
source                     1..248
                           mol_type = protein
                           organism = Canis lupus
SEQUENCE: 2
MWQLVSSTAL LLLVSAGTQA DVPKAVVVLE PKWNRVLTMD SVTLKCQGDH LLRDNYTWLH    60
NGRPISNQIS TYIIKNASIK NSGEYRCQTD QSKLSDPVQL EVHTGWLLLQ VPRLVFQEGE   120
LIQLKCHSWK NTPVRNVQYF QNGRGKKFFY NNSEYHIPAA TSEHNGSYFC RGIIGKKNES   180
SEAVNIIQG SSLPSTSLLL SHWPQIPFSL VMALLFAVDT GLYFAVQRDL RSSMGNLKNS    240
KVIWSQGS                                                           248

SEQ ID NO: 3               moltype = AA   length = 357
FEATURE                    Location/Qualifiers
source                     1..357
                           mol_type = protein
                           organism = Homo sapiens
SEQUENCE: 3
MWFLTTLLLW VPVDGQVDTT KAVISLQPPW VSVFQEETVT LHCEVLHLPG SSSTQWFLNG    60
TATQTSTPSY RITSASVNDS GEYRCQRGLS GRSDPIQLEI HRGWLLLQVS SRVFTEGEPL   120
ALRCHAWKDK LVYNVLYYRN GKAPKFFHWN SNLTILKTNI SHNGTYHCSG MGKHRYTSAG   180
ISVTVKELFP APVLNASVTS PLLEGNLVTL SCETKLLLQR PGLQLYFSFY MGSKTLRGRN   240
TSSEYQILTA RREDSGLYWC EAATEDGNVL KRSPELELQV LGLQLPTPVW PHVLFYLAVG   300
IMFLVNTVLV VTIRKELKRK KKWDLEISLD SGHEKKVTSS LQEDRHLEEE LKCQEQK      357

SEQ ID NO: 4               moltype = AA   length = 372
FEATURE                    Location/Qualifiers
source                     1..372
                           mol_type = protein
                           organism = Canis lupus
SEQUENCE: 4
MWLLTVLLLW VPAGAQTDPV KAVITLQPPW VSVFQEESVT LWCEGPHLPG DSSTQWFLNG    60
TATQTLTPRY RIAAASVNDN GEYRCQTGLS VLSDPIQLGI HRDWLILQVS GRVFTEGEPL   120
TLRCHGWNNK LVYNVLFYQN GTVLKFSPQN SEFTILKTTL HHNGIYHCSA MGKHRYESAG   180
VSITIKELFP APVLKASLSS PILEGHVVNL SCETKLLLQR PGLQLYFSFY MGSKTLLSRN   240
TSSEYQILTA KKEDSGLYWC EATTEDGNVV KRSPELELQV VGPQTLTPVW PHVLFYVAMG   300
MIFLVDTIFC MIIHKELQRK KKWNLEISLY SGLEKRVDSY LQKERDLEEP KYQELEQQE    360
KTPQKPPEGE QQ                                                      372

SEQ ID NO: 5               moltype = AA   length = 211
FEATURE                    Location/Qualifiers
source                     1..211
                           mol_type = protein
                           organism = Canis lupus
SEQUENCE: 5
MKCSWVIFFL MAVVIGINSE VQLQQSGAEL VRSGASVKLS CTASGFNIKD YYMHWVKQRP    60
EQGLEWIGWL DPENGDTVYA PKFQGRATMT ADTSSNTAYL HLSSLTSEDT AVYYCNALVY   120
SLLGQDYWGQ GTTLTVSSAK TTPPSVYPLA PGSAAQTNSM VTLGCLVKGY FPEPVTVTWN   180
SGSLSSGVHT FPAVLQSDLY TLSSSVTVPS S                                 211

SEQ ID NO: 6               moltype = AA   length = 8
FEATURE                    Location/Qualifiers
source                     1..8
                           mol_type = protein
                           organism = Canis lupus
SEQUENCE: 6
GFNIKDYY                                                             8
```

```
SEQ ID NO: 7              moltype = AA   length = 8
FEATURE                   Location/Qualifiers
source                    1..8
                          mol_type = protein
                          organism = Canis lupus
SEQUENCE: 7
LDPENGDT                                                              8

SEQ ID NO: 8              moltype = AA   length = 12
FEATURE                   Location/Qualifiers
source                    1..12
                          mol_type = protein
                          organism = Canis lupus
SEQUENCE: 8
NALVYSLLGQ DY                                                         12

SEQ ID NO: 9              moltype = AA   length = 204
FEATURE                   Location/Qualifiers
source                    1..204
                          mol_type = protein
                          organism = Canis lupus
SEQUENCE: 9
MDFQVQIFSF LLISASVIMS RGQILLTQSP AIMSASPGEK VTMTCSASSS VGYMHWYQQK      60
PGSSPKPWIY DTSDLASGFP ARFSGSRSGT SYSLIISSME AEDAATYYCH QRSFYPYTFG     120
GGTKLEIKRA DAAPTVSIFP PSSEQLTSGG ASVVCFLNNF YPKDINVKWK IDGSERQNGV     180
LNSWTDQDSK DSTYSMSSTL TLTK                                           204

SEQ ID NO: 10             moltype = AA   length = 5
FEATURE                   Location/Qualifiers
source                    1..5
                          mol_type = protein
                          organism = Canis lupus
SEQUENCE: 10
SSVGY                                                                 5

SEQ ID NO: 11             moltype =      length =
SEQUENCE: 11
000

SEQ ID NO: 12             moltype = AA   length = 9
FEATURE                   Location/Qualifiers
source                    1..9
                          mol_type = protein
                          organism = Canis lupus
SEQUENCE: 12
HQRSFYPYT                                                             9

SEQ ID NO: 13             moltype = AA   length = 118
FEATURE                   Location/Qualifiers
source                    1..118
                          mol_type = protein
                          organism = Canis lupus
SEQUENCE: 13
QVQLQQSGAE LVRPGASVTL SCKASGYTFI DFEIHWVKQT PVHGLEWIGA IDPETGGTAY      60
NQKFKGKATL TADKSSSAAY MELRSLTSED SAVYYCTRRA TVVGSDYWGQ GTTLTVSS      118

SEQ ID NO: 14             moltype = AA   length = 5
FEATURE                   Location/Qualifiers
source                    1..5
                          mol_type = protein
                          organism = Canis lupus
SEQUENCE: 14
DFEIH                                                                 5

SEQ ID NO: 15             moltype = AA   length = 20
FEATURE                   Location/Qualifiers
source                    1..20
                          mol_type = protein
                          organism = Canis lupus
SEQUENCE: 15
AIDPETGGTA YNQKFKGKAT                                                 20

SEQ ID NO: 16             moltype = AA   length = 9
FEATURE                   Location/Qualifiers
source                    1..9
                          mol_type = protein
                          organism = Canis lupus
SEQUENCE: 16
```

```
RATVVGSDY                                                                     9

SEQ ID NO: 17            moltype = AA  length = 107
FEATURE                  Location/Qualifiers
source                   1..107
                         mol_type = protein
                         organism = Canis lupus
SEQUENCE: 17
DIVMTQSHKF MSTSVGDRVS IACKASQDVG AAVAWYHQKP GQSPKLLIYW ASTRHTGVPD     60
RFTGSGSGTD STLTISTVQS EDLAEYFCQQ YSSYPFTFGS GTKLEIK                  107

SEQ ID NO: 18            moltype = AA  length = 11
FEATURE                  Location/Qualifiers
source                   1..11
                         mol_type = protein
                         organism = Canis lupus
SEQUENCE: 18
KASQDVGAAV A                                                                 11

SEQ ID NO: 19            moltype = AA  length = 7
FEATURE                  Location/Qualifiers
source                   1..7
                         mol_type = protein
                         organism = Canis lupus
SEQUENCE: 19
WASTRHT                                                                       7

SEQ ID NO: 20            moltype = AA  length = 9
FEATURE                  Location/Qualifiers
source                   1..9
                         mol_type = protein
                         organism = Canis lupus
SEQUENCE: 20
QQYSSYPFT                                                                     9

SEQ ID NO: 21            moltype = DNA  length = 39
FEATURE                  Location/Qualifiers
source                   1..39
                         mol_type = other DNA
                         organism = synthetic construct
SEQUENCE: 21
gcccagccgg ccagatctca aacagacccc gtaaaggca                                   39

SEQ ID NO: 22            moltype = DNA  length = 41
FEATURE                  Location/Qualifiers
source                   1..41
                         mol_type = other DNA
                         organism = synthetic construct
SEQUENCE: 22
gcggatcccg ggagatctaa aaagaagtgg gaggcaccat c                                41

SEQ ID NO: 23            moltype = DNA  length = 42
FEATURE                  Location/Qualifiers
source                   1..42
                         mol_type = other DNA
                         organism = synthetic construct
SEQUENCE: 23
tctagactgc cggatccaga gggtgagatg acaacaccca ga                               42

SEQ ID NO: 24            moltype = DNA  length = 42
FEATURE                  Location/Qualifiers
source                   1..42
                         mol_type = other DNA
                         organism = synthetic construct
SEQUENCE: 24
tcgaatttaa atggatcctt aagggatgct gtcgttttct at                               42

SEQ ID NO: 25            moltype = DNA  length = 22
FEATURE                  Location/Qualifiers
source                   1..22
                         mol_type = other DNA
                         organism = synthetic construct
SEQUENCE: 25
tagctggaag aacacgcccg ta                                                     22

SEQ ID NO: 26            moltype = DNA  length = 22
FEATURE                  Location/Qualifiers
source                   1..22
                         mol_type = other DNA
```

```
                        organism = synthetic construct
SEQUENCE: 26
gcagaagtag gagccattgt gt                                                22

SEQ ID NO: 27           moltype = DNA  length = 44
FEATURE                 Location/Qualifiers
source                  1..44
                        mol_type = other DNA
                        organism = synthetic construct
SEQUENCE: 27
gaagacaccg actctagagc agtgacttgc tgaccctaat gtga                        44

SEQ ID NO: 28           moltype = DNA  length = 59
FEATURE                 Location/Qualifiers
source                  1..59
                        mol_type = other DNA
                        organism = synthetic construct
SEQUENCE: 28
gtagtcagcc cgggatcctt aatgatgatg atgatgatgg ggccagtgtg aaaggagta        59

SEQ ID NO: 29           moltype = DNA  length = 39
FEATURE                 Location/Qualifiers
source                  1..39
                        mol_type = other DNA
                        organism = synthetic construct
SEQUENCE: 29
gactctagag gagataacat gtggctcttg acagttcta                              39

SEQ ID NO: 30           moltype = DNA  length = 52
FEATURE                 Location/Qualifiers
source                  1..52
                        mol_type = other DNA
                        organism = synthetic construct
SEQUENCE: 30
ccgggatcct taatgatgat gatgatgatg cacttgaagc tccaactcag gg               52

SEQ ID NO: 31           moltype = DNA  length = 22
FEATURE                 Location/Qualifiers
source                  1..22
                        mol_type = other DNA
                        organism = synthetic construct
SEQUENCE: 31
catgggaaag catcgctacg aa                                                22

SEQ ID NO: 32           moltype = DNA  length = 22
FEATURE                 Location/Qualifiers
source                  1..22
                        mol_type = other DNA
                        organism = synthetic construct
SEQUENCE: 32
tcagattgac cacatgcccc tc                                                22

SEQ ID NO: 33           moltype = AA  length = 15
FEATURE                 Location/Qualifiers
source                  1..15
                        mol_type = protein
                        organism = synthetic construct
SEQUENCE: 33
GGGGSGGGGS GGGGS                                                        15

SEQ ID NO: 34           moltype = AA  length = 18
FEATURE                 Location/Qualifiers
source                  1..18
                        mol_type = protein
                        organism = synthetic construct
SEQUENCE: 34
GSTSGSGKPG SGEGSTKG                                                     18

SEQ ID NO: 35           moltype = AA  length = 20
FEATURE                 Location/Qualifiers
source                  1..20
                        mol_type = protein
                        organism = synthetic construct
SEQUENCE: 35
PSGQAGAAAS ESLFVSNHAY                                                   20

SEQ ID NO: 36           moltype = AA  length = 7
FEATURE                 Location/Qualifiers
source                  1..7
```

-continued

```
                         mol_type = protein
                         organism = synthetic construct
SEQUENCE: 36
EASGGPE                                                              7

SEQ ID NO: 37            moltype = AA   length = 38
FEATURE                  Location/Qualifiers
source                   1..38
                         mol_type = protein
                         organism = synthetic construct
SEQUENCE: 37
AEAAKEAAKE AAKEAAKALE AEAAKEAAKE AAKEAAKA                            38

SEQ ID NO: 38            moltype = AA   length = 10
FEATURE                  Location/Qualifiers
source                   1..10
                         mol_type = protein
                         organism = synthetic construct
SEQUENCE: 38
AEAAKEAAKA                                                          10

SEQ ID NO: 39            moltype = AA   length = 22
FEATURE                  Location/Qualifiers
source                   1..22
                         mol_type = protein
                         organism = synthetic construct
SEQUENCE: 39
SGGGGSGGGG SGGGGSGGGG SG                                            22

SEQ ID NO: 40            moltype = AA   length = 10
FEATURE                  Location/Qualifiers
source                   1..10
                         mol_type = protein
                         organism = synthetic construct
SEQUENCE: 40
GGGGSGGGGS                                                          10

SEQ ID NO: 41            moltype = AA   length = 18
FEATURE                  Location/Qualifiers
source                   1..18
                         mol_type = protein
                         organism = synthetic construct
SEQUENCE: 41
GSTSGSGKPG SGEGSTKG                                                 18

SEQ ID NO: 42            moltype = AA   length = 15
FEATURE                  Location/Qualifiers
source                   1..15
                         mol_type = protein
                         organism = synthetic construct
SEQUENCE: 42
EPKSSDKTHT SPPSP                                                    15

SEQ ID NO: 43            moltype = AA   length = 25
FEATURE                  Location/Qualifiers
source                   1..25
                         mol_type = protein
                         organism = synthetic construct
SEQUENCE: 43
RATPSHNSHQ VPSAGGPTAN SGTSG                                         25

SEQ ID NO: 44            moltype = AA   length = 19
FEATURE                  Location/Qualifiers
source                   1..19
                         mol_type = protein
                         organism = synthetic construct
SEQUENCE: 44
SSGGGGSGGG GGGSSRSSL                                                19

SEQ ID NO: 45            moltype = AA   length = 197
FEATURE                  Location/Qualifiers
source                   1..197
                         mol_type = protein
                         organism = Homo sapiens
SEQUENCE: 45
RNLPVATPDP GMFPCLHHSQ NLLRAVSNML QKARQTLEFY PCTSEEIDHE DITKDKTSTV    60
EACLPLELTK NESCLNSRET SFITNGSCLA SRKTSFMMAL CLSSIYEDLK MYQVEFKTMN   120
AKLLMDPKRQ IFLDQNMLAV IDELMQALNF NSETVPQKSS LEEPDFYKTK IKLCILLHAF   180
RIRAVTIDRV MSYLNAS                                                 197
```

```
SEQ ID NO: 46          moltype = AA   length = 306
FEATURE                Location/Qualifiers
source                 1..306
                       mol_type = protein
                       organism = Homo sapiens
SEQUENCE: 46
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCS                                                              306

SEQ ID NO: 47          moltype = AA   length = 114
FEATURE                Location/Qualifiers
source                 1..114
                       mol_type = protein
                       organism = Homo sapiens
SEQUENCE: 47
NWVNVISDLK KIEDLIQSMH IDATLYTESD VHPSCKVTAM KCFLLELQVI SLESGDASIH    60
DTVENLIILA NNSLSSNGNV TESGCKECEE LEEKNIKEFL QSFVHIVQMF INTS         114

SEQ ID NO: 48          moltype = DNA   length = 43
FEATURE                Location/Qualifiers
source                 1..43
                       mol_type = other DNA
                       organism = synthetic construct
SEQUENCE: 48
ctctagactg ccggatccgc agtgacttgc tgaccctaat gtg                      43

SEQ ID NO: 49          moltype = DNA   length = 42
FEATURE                Location/Qualifiers
source                 1..42
                       mol_type = other DNA
                       organism = synthetic construct
SEQUENCE: 49
tcgaatttaa atggatccag agaggtccag aggggttgct tt                       42

SEQ ID NO: 50          moltype = DNA   length = 39
FEATURE                Location/Qualifiers
source                 1..39
                       mol_type = other DNA
                       organism = synthetic construct
SEQUENCE: 50
gcccagccgg ccagatctac acaagctgca gatgtccca                           39

SEQ ID NO: 51          moltype = DNA   length = 42
FEATURE                Location/Qualifiers
source                 1..42
                       mol_type = other DNA
                       organism = synthetic construct
SEQUENCE: 51
gcggatcccg ggagatctag agaggtccag aggggttgct tt                       42

SEQ ID NO: 52          moltype = DNA   length = 38
FEATURE                Location/Qualifiers
source                 1..38
                       mol_type = other DNA
                       organism = synthetic construct
SEQUENCE: 52
tctagactgc cggatccact agtaacggcc gccagtgt                            38

SEQ ID NO: 53          moltype = DNA   length = 42
FEATURE                Location/Qualifiers
source                 1..42
                       mol_type = other DNA
                       organism = synthetic construct
SEQUENCE: 53
tcgaatttaa atggatccag agaggtccag aggggttgct tt                       42

SEQ ID NO: 54          moltype = DNA   length = 47
FEATURE                Location/Qualifiers
source                 1..47
                       mol_type = other DNA
                       organism = synthetic construct
SEQUENCE: 54
tctagactgc cggatccgga gataacatgt ggctcttgac agttcta                  47
```

```
SEQ ID NO: 55          moltype = DNA  length = 41
FEATURE                Location/Qualifiers
source                 1..41
                       mol_type = other DNA
                       organism = synthetic construct
SEQUENCE: 55
tcgaatttaa atggatccaa aaagaagtgg gaggcaccat c                              41

SEQ ID NO: 56          moltype = AA  length = 505
FEATURE                Location/Qualifiers
source                 1..505
                       mol_type = protein
                       organism = synthetic construct
SEQUENCE: 56
MEQILLTQSP AIMSASPGEK VTMTCSASSS VGYMHWYQQK PGSSPKPWIY DTSDLASGFP    60
ARFSGSRSGT SYSLIISSME AEDAATYYCH QRSFYPYTFG GGTKLEIKGG GGSGGGGSGG    120
GGSEVQLQQS GAELVRSGAS VKLSCTASGF NIKDYYMHWV KQRPEQGLEW IGWLDPENGD    180
TVYAPKFQGR ATMTADTSSN TAYLHLSSLT SEDTAVYYCN ALVYSLLGQD YWGQGTTLTV    240
SSPSGQAGAA ASESLFVSNH AYNWQDVILD LEKIDNLIQS IHMDATLYTE SDVHPSCKVT    300
AMKCFLLELG VISLESGSHP IKEAVENLII LANSDLSSKG NITETGCKEC EELEEKSIKE    360
FLQSFVHIVQ MFINSSEASG GPEQVQLVES GGGLVQPGGS LRLSCAASGF TFSSYWMYWV    420
RQTPGKGLEW VSTINRDGSA TWYADSVKGR FTISRDNAKN TGYLQMNSLK PDDTAVYYCV    480
SDPDNYSSDE MVPYWGQGTQ VTVSS                                         505

SEQ ID NO: 57          moltype = AA  length = 629
FEATURE                Location/Qualifiers
source                 1..629
                       mol_type = protein
                       organism = synthetic construct
SEQUENCE: 57
MEQILLTQSP AIMSASPGEK VTMTCSASSS VGYMHWYQQK PGSSPKPWIY DTSDLASGFP    60
ARFSGSRSGT SYSLIISSME AEDAATYYCH QRSFYPYTFG GGTKLEIKGG GGSGGGGSGG    120
GGSEVQLQQS GAELVRSGAS VKLSCTASGF NIKDYYMHWV KQRPEQGLEW IGWLDPENGD    180
TVYAPKFQGR ATMTADTSSN TAYLHLSSLT SEDTAVYYCN ALVYSLLGQD YWGQGTTLTV    240
SSPSGQAGAA ASESLFVSNH AYNWQDVILD LEKIDNLIQS IHMDATLYTE SDVHPSCKVT    300
AMKCFLLELG VISLESGSHP IKEAVENLII LANSDLSSKG NITETGCKEC EELEEKSIKE    360
FLQSFVHIVQ MFINSSEASG GPEGTDIVMT QPPAIMSASP GEKVTMTCSA SSSVSYMHWY    420
QQKSGTSPKR WIYDTSKLAS GVPDRFSSSG SGTDFTLRIS RVEAEDVGVY YCAQNLELPF    480
TFGGGTKLEI KSSGGGGSGG GGGGSSRSSL EVNVVESGGG LVQPGDSLRL SCATSGFTFD    540
YFMSWVRQPP GKSLEWLGLI RNKVNGYTAE YSASVKGRFT ISRDNSRGIL YLQMYTLRAE    600
DSATYYCVRA STGTSFVYWG QGTLVTVSA                                     629
```

ANTI-CANINE CD16 POLYPEPTIDES, ANTI-CANINE CD64 POLYPEPTIDES, COMPOSITIONS INCLUDING SAME, AND METHODS OF USING

CROSS-REFERENCE TO RELATED APPLICATION

This application claims the benefit of U.S. Provisional Patent Application No. 63/301,143, filed Jan. 20, 2022, which is incorporated herein by reference in its entirety.

SEQUENCE LISTING

This application contains a Sequence Listing electronically submitted to the United States Patent and Trademark Office via EFS-Web as an ASCII text file entitled "0110-000687US01.xml" having a size of 53 kilobytes and created on Jan. 19, 2023. Due to the electronic filing of the Sequence Listing, the electronically submitted Sequence Listing serves as both the paper copy required by 37 CFR § 1.821(c) and the CRF required by § 1.821(e). The information contained in the Sequence Listing is incorporated by reference herein.

SUMMARY

This disclosure describes, in one aspect, an anti-canine CD16 polypeptide. Generally, the anti-canine CD16 polypeptide includes a CDR region of SEQ ID NO:5, a CDR region of SEQ ID NO:9, or a functional variant of either CDR region. In one or more embodiments, the anti-canine CD16 polypeptide includes SEQ ID NO:6 or a functional variant thereof, SEQ ID NO: 7 or a functional variant thereof, SEQ ID NO:8 or a functional variant thereof, SEQ ID NO: 10 or a functional variant thereof, SEQ ID NO: 11 (DTS) or a functional variant thereof, or SEQ ID NO: 12, or a functional variant thereof.

In another aspect, this disclosure describes an anti-canine CD64 polypeptide. Generally, the anti-canine CD64 polypeptide includes a CDR region of SEQ ID NO:13, a CDR region of SEQ ID NO:17, or a functional variant of either CDR region. In one or more embodiments, the anti-canine CD64 polypeptide includes SEQ ID NO:14 or a functional variant thereof, SEQ ID NO:15 or a functional variant thereof, SEQ ID NO:16 or a functional variant thereof, SEQ ID NO:18 or a functional variant thereof, SEQ ID NO:19 or a functional variant thereof, or SEQ ID NO:20, or a functional variant thereof.

In another aspect, this disclosure describes multispecific compounds that include an anti-canine CD16 polypeptide or an anti-canine CD64 polypeptide linked to one or more additional functional domains. In one or more embodiments, the multispecific compound can further include a targeting domain that selectively binds to a target. In one or more embodiments, the multispecific compound can further include an immune cell activating domain. In one or more embodiments, functional domains in the multispecific compound may be linked by linking segments.

In another aspect, this disclosure describes an isolated nucleic acid sequence that encodes an anti-canine CD16 polypeptide, an anti-canine CD64 polypeptide, a multispecific compound that includes an anti-canine CD16 polypeptide, or a multispecific compound that includes an anti-canine CD64 polypeptide.

In another aspect, this disclosure describes a host cell that includes a nucleic acid sequence that encodes an anti-canine CD16 polypeptide, an anti-canine CD64 polypeptide, a multispecific compound that includes an anti-canine CD16 polypeptide, or a multispecific compound that includes an anti-canine CD64 polypeptide.

In another aspect, this disclosure describes a human NK cell engineered to express canine CD16.

In another aspect, this disclosure describes a human NK cell engineered to express canine CD64.

In another aspect, this disclosure describes a canine NK cell engineered to express canine CD64.

In another aspect, this disclosure describes a method that includes administering to a subject a multispecific compound that includes an anti-canine CD16 polypeptide or a multispecific compound that includes an anti-canine CD64 polypeptide in an amount effective to induce natural killer (NK)-mediated killing of a cell.

In another aspect, this disclosure describes a method that includes administering to the subject NK cells engineered to express canine CD64 and administering to a subject a multispecific compound that includes an anti-canine CD64 polypeptide in an amount effective to induce natural killer (NK)-mediated killing of a cell.

In another aspect, this disclosure describes a method of treating a subject having, or at risk of having, cancer in which tumor cells express a tumor antigen. Generally, the method includes administering to the subject a multispecific compound in an amount effective to ameliorate at least one symptom or clinical sign of the cancer or reduce risk of the subject developing cancer compared a comparable untreated individual. In one or more embodiments, the multispecific compound includes an anti-canine CD16 polypeptide or a multispecific compound that includes an anti-canine CD64 polypeptide, and a targeting domain that specifically binds to the tumor antigen.

In one or more embodiments, the cancer being treated can include prostate cancer, lung cancer, colon cancer, rectum cancer, urinary bladder cancer, melanoma, kidney cancer, renal cancer, oral cavity cancer, pharynx cancer, pancreas cancer, uterine cancer, thyroid cancer, skin cancer, head and neck cancer, cervical cancer, ovarian cancer, osteosarcoma, or a hematopoietic cancer.

In one or more embodiments, the multispecific compound is administered prior to, simultaneously with, or following chemotherapy, surgical resection of a tumor, or radiation therapy.

In embodiments in which the multispecific compound includes an anti-canine CD64 polypeptide, the method can further include administering to the subject NK cells engineered to express canine CD64 or a fragment thereof recognized by the anti-canine CD64 polypeptide.

In another aspect, this disclosure describes a method of treating a subject having, or at risk of having, an infectious condition in which infected cells express an infectious antigen. Generally, the method includes administering to the subject a multispecific compound in an amount effective to ameliorate at least one symptom or clinical sign of the infectious condition or reduce risk of the subject developing the infectious compared a comparable untreated individual. In one or more embodiments, the multispecific compound includes an anti-canine CD16 polypeptide or a multispecific compound that includes an anti-canine CD64 polypeptide, and a targeting domain that specifically binds to the infectious antigen.

In embodiments in which the multispecific compound includes an anti-canine CD64 polypeptide, the method can further include administering to the subject NK cells engineered to express canine CD64 or a fragment thereof recognized by the anti-canine CD64 polypeptide.

In another aspect, this disclosure describes a targeted imaging compound, Generally, the targeted imaging compound includes a targeting domain and an imaging domain. The targeting domain includes an anti-canine CD16 polypeptide or an anti-canine CD64 polypeptide.

In one or more embodiments, the imaging domain can include a colorimetric label, a fluorescent label, a radioactive label, a magnetic label, or an enzymatic label.

In yet another aspect, this disclosure describes a capture assay device that includes, immobilized to a substrate, an anti-canine CD16 polypeptide or an anti-canine CD64 polypeptide.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
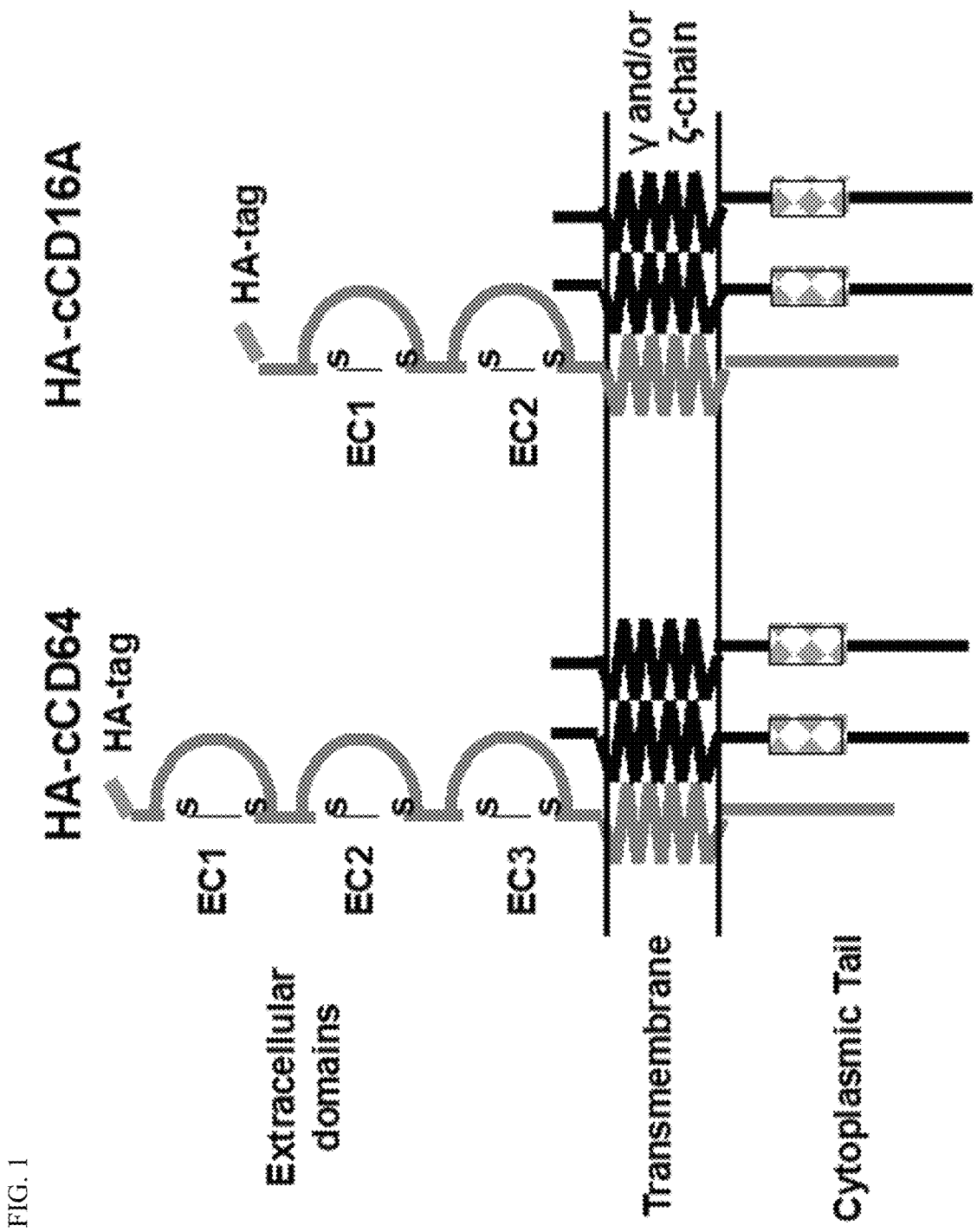
FIG. 1. Characterization of anti-canine CD16A and anti-canine CD64 mAbs. Schematic representation of recombinant intact canine CD16A and canine CD64 with an N-terminus HA-tag. The signaling adaptors FcRγ and/or CD3 ζ (γ and/or ζ chain) non-covalently associate with human CD16A and CD64 as a homodimer or heterodimer.

This disclosure describes anti-canine CD16 polypeptides, anti-canine CD64 polypeptides, compounds and devices that include an anti-canine CD16 polypeptide or an anti-canine CD64 polypeptide, and methods of using such compounds and devices. Exemplary platforms in which an anti-canine CD16 polypeptide or an anti-canine CD64 polypeptide may be used include, but are not limited to, chimeric antigen receptor therapies (e.g., CAR-NK therapy, CAR-T therapy, CAR-macrophage therapy, etc.), multispecific immune cell engager technologies (e.g., bispecific killer engagers, trispecific killer engagers, bispecific T cell engagers, trispecific T cell engagers, etc.), targeted immunotherapies (e.g., targeted ADAM17 blocker (TAB) therapy), delivery of therapeutics (e.g., antibody-drug conjugates, delivery of therapeutic radioisotopes, delivery of toxins, delivery of cytokines, delivery of chemokines), imaging technologies (delivery of labeling constructs and/or labeling radioisotopes), cell and/or ligand capture technologies (e.g., ELISA, etc.).

Human natural killer (NK) cells are innate cytotoxic lymphocytes that interrogate cells in the body to identify those that are stressed, infected, or neoplastic. NK cells are rapidly activated and release cytolytic factors as well as cytokines and chemokines that stimulate other components of the immune system. NK cell activation is mediated by various ligands and attached antibodies on target cells. Thus, for example, NK cells can target tumor cells in an antigen-specific manner by recognizing antibodies bund to tumor cells. This process induces antibody-dependent cell-mediated cytotoxicity (ADCC) and is mediated by the low affinity IgG Fc receptor CD16A (FcγRIIIA). Anti-tumor monoclonal antibodies (mAbs) provide a rapidly expanding repertoire of targeting elements for NK cells. Thus, exploiting ADCC by NK cells is a mechanism exploited by cancer immunotherapies.

The clinical performance of anti-tumor antibodies is limited by certain attributes of CD16A. For example, CD16A undergoes rapid ectodomain shedding by a disintegrin and metalloproteinase 17 (ADAM17) upon NK cell activation with diverse stimuli. Ectodomain shedding can be inhibited in human NK cells by engineering a noncleavable CD16A or blocking ADAM17, thereby enhancing NK cell release of IFNγ and target cell killing in the presence of mAb therapies. As another example, CD16A is a low affinity FcγR that stably binds to cell-bound IgG, but not soluble monomeric IgG. In humans, two CD16A allelic variants exist: one with either phenylalanine (F) at amino acid position 158, the other with a valine (V) at amino acid position 158. The CD16A-158V variant has affinity for IgG1 that is approximately two-fold higher than the CD16A-158F variant. Cancer patients homozygous for CD16A-158V responded significantly better to tumor targeting mAbs, indicating that increased binding affinity between CD16A and tumor-targeting mAbs enhance NK cell anti-tumor effector functions. A strategy to increase both the binding affinity and avidity between NK cells and antibody-opsonized tumor cells has involved modifying the FcγR on NK cells.

CD64 (FcγRI) is a high affinity IgG FcR and it binds to the same IgG isotypes as CD16A, but with more than 30-fold higher affinity than CD16A. CD64 is expressed by myeloid leukocyte populations but not lymphocytes, including NK cells. Human NK cells have been engineered to express recombinant CD64 to increase their ADCC potency (Snyder et al., *Front Immunol*, 2018, 9:2873; Hintz et al., *Cancer Immunol Res* 9(11):1270-1282, 2021). Due to its high affinity state, NK cells expressing recombinant CD64 can be "armed" with anti-tumor mAbs, which can be switched or mixed for universal tumor antigen targeting.

The clinical translation of engineered NK cell immunotherapies into successful cancer therapies has been slow, due in part to the use of animal models with species differences in their immune cell effector functions. For instance, the study of ADCC in mice is confounded by a considerable divergence in human and mouse FcγR expression profiles and function. For instance, mature human NK cells uniformly express high levels of CD16A under steady state conditions, whereas mouse CD16 (FcγRIII) is expressed at low levels by NK cells, and is actually more closely related to human CD32A (FcγRIIA), which is not expressed by human NK cells. Moreover, mouse CD16 shedding by ADAM17 is different, and is regulated differently, than human CD16A. An ideal animal model for understanding the mechanisms that underlie success and failure of human immunotherapies should incorporate heterogeneous spontaneous disease and an intact immune system that is similar to humans.

The dog provides an advantageous model for preclinical testing of engineered NK cells for efficacy and safety. The comparable incidence of human and certain canine malignancies, shared biologic and pathologic characteristics, and similar response to therapy indicate that dogs can provide a clinically-relevant disease model. Based on morphology, canine NK cells are medium to large lymphocytes with electron-dense intracytoplasmic granules that contain granzyme B and perforin. These cells express at the mRNA level several genes associated with NK cells, such as NK1.1, NKG2D, CD94, CD96, NKp30, NKp44, NKp46, NKG2D, CD16A, DNAM-1, perforin, and granzyme B, and based on transcriptome analysis, canine NK cells are globally more similar to human NK cells than to mouse NK cells (Gingrich et al., *Front Immunol*, 12, 670309 (2021)). Canine NK cells also mediate natural cytotoxicity and ADCC. However, a lack of available species-specific antibodies has hindered efforts to study FcγRs on canine leukocytes.

This disclosure describes cloning the canine Fc receptor CD16A and the canine Fc receptor CD64, then generating monoclonal antibodies (mAbs) against each canine protein. This disclosure further reports the expression patterns of these FcγRs on dog peripheral blood leukocytes. CD64 was expressed by neutrophils and monocytes, but not lymphocytes, while canine CD16A was expressed at high levels by a subset of monocytes and lymphocytes. These expression patterns are similar to that of human leukocytes. Based on phenotypic characteristics, the CD16A$^+$ lymphocytes included T cells (CD3$^+$ CD8$^+$ CD5$^{dim}$ α/β TCR$^+$) and NK cells (CD3$^-$ CD5$^-$ CD94$^+$), but not B cells. Like human CD16A, canine CD16A was downregulated by a disintegrin and metalloproteinase 17 (ADAM17) upon leukocyte activation, revealing a conserved means of regulation. Further, this disclosure provides data that directly demonstrate that both canine CD16A and CD64 can induce ADCC when expressed in the NK-92 cell line. Thus, this disclosure allows one to engineer canine NK cells with high affinity recombinant canine CD64 to maximize ADCC and to test their safety and efficacy to benefit both humans and dogs.

Generation of Monoclonal Antibodies (mAbs) Against Canine CD16A and Canine CD64

Figure 11:
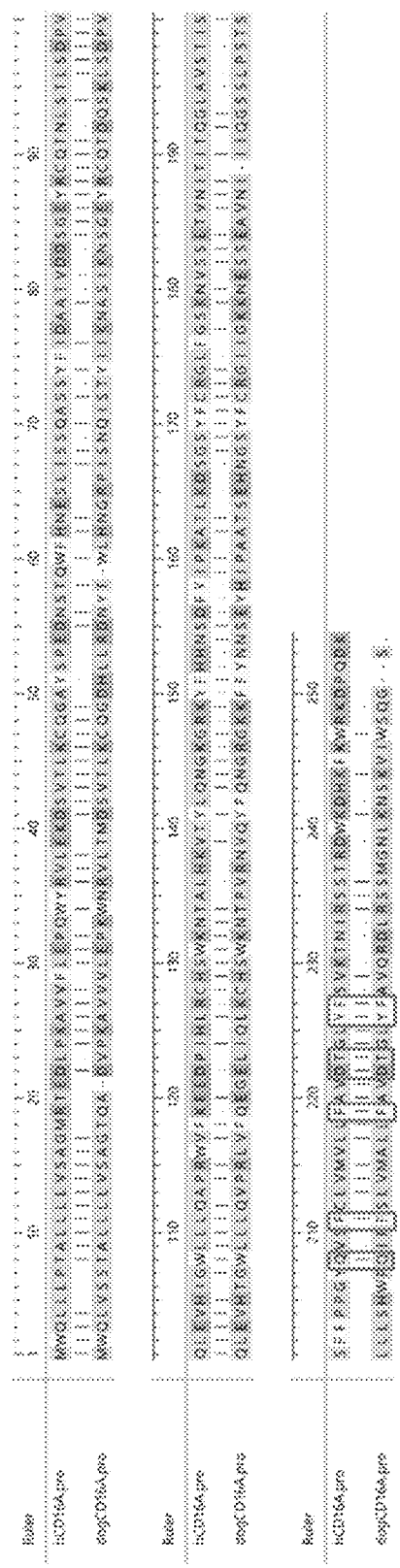
FIG. 11. Amino acid alignment of human CD16A and canine CD16A. The amino acid sequences of human CD16A and canine CD16A are from the NCBI reference sequences (human CD16: X52645.1, SEQ ID NO:1; canine CD16A: XM_022415348, SEQ ID NO:2). The amino acid sequence of the human CD16A transmembrane region (underlined) is previously reported (Zidovetzki et al., *Biophys Chem*, 100 (1-3):555-75, 2003). The boxed residues represent amino acids involved in association with the signaling adaptors FcRγ and CD3ζ, as previously reported (Blazquez-Moreno et al., *Proc Natl Acad Sci USA*, 114(28):E5645-E5654, 2017).
Figure 12:
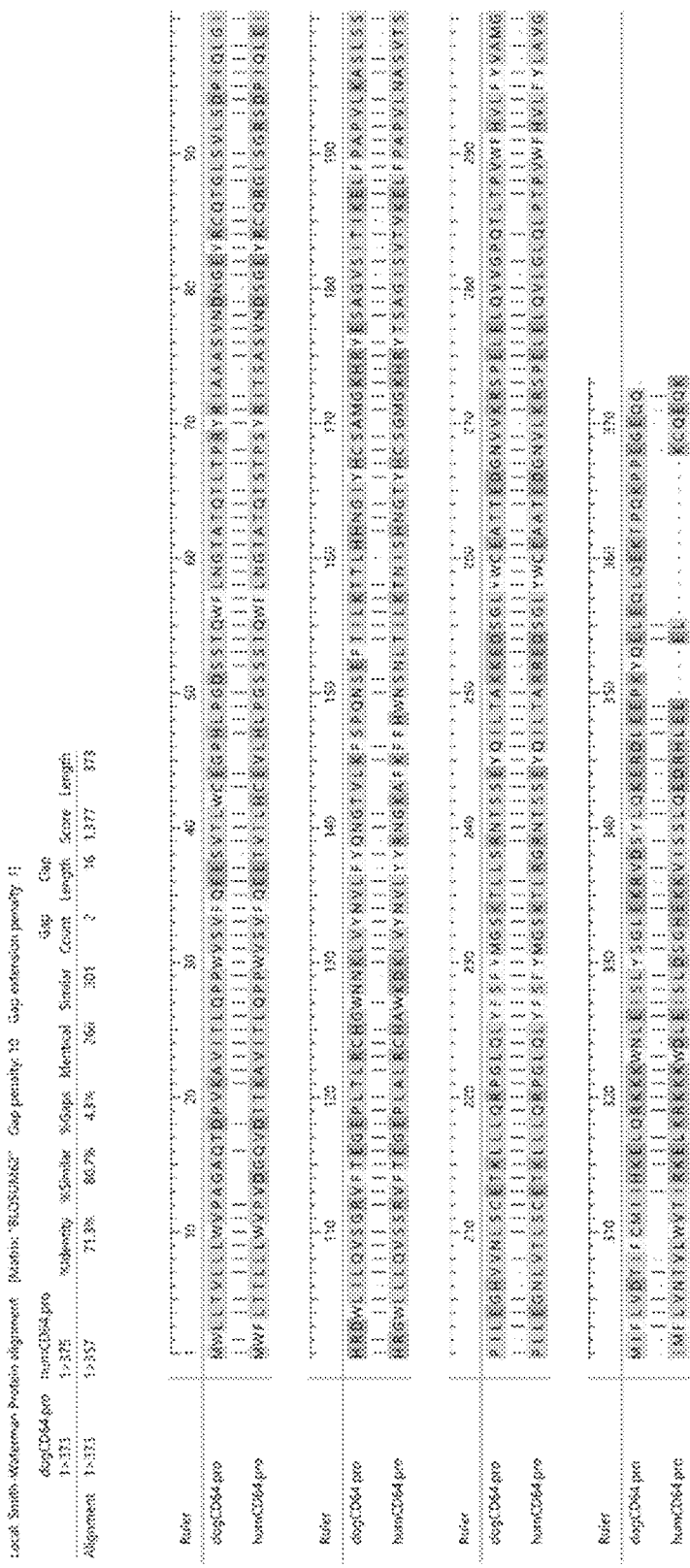
FIG. 12. Amino acid alignment of human and canine CD64. The amino acid sequences of human and canine CD64 are from the NCBI reference sequences (human CD64: X14356.1, SEQ ID NO:3; canine CD64: NM_001002976, SEQ ID NO:4).

In humans, CD16 has two isoforms, CD16A and CD16B, encoded by two highly homologous genes. CD16A is a transmembrane protein expressed by lymphocytes and some monocytes, whereas CD16B is linked to the plasma membrane via a glycophosphatidylinositol (GPI) anchor and primarily expressed by neutrophils. Canine CD16 is a transmembrane protein and therefore we refer to it here as CD16A. The CD16B isoform does not exist in the canine genome or cDNA. Currently, there are no commercially available mAbs specific to canine CD16A or CD64 or any that are cross reactive with either canine CD16 or canine CD64. For canine CD16A, this may be due to its relatively low levels of amino acid sequence identity and similarity with human CD16A (57.1% and 71.7%, respectively) (FIG. 11). The amino acid sequence identity (72.5%) and similarity (80.7%) between canine CD64 and human CD64 are higher (FIG. 12). While reactivity by the anti-human CD16 mAb clone LNK16 with dog peripheral blood monocytes has been reported (Tuohy et al., *J Vet Intern Med*, 30(4): 1167-1178, 2016), others report a lack of specific activity by the same mAb with dog PBMCs (Gibbons et al., *Vet Immunol Immunopathol* 190:26-30, 2017).

Figure 2:
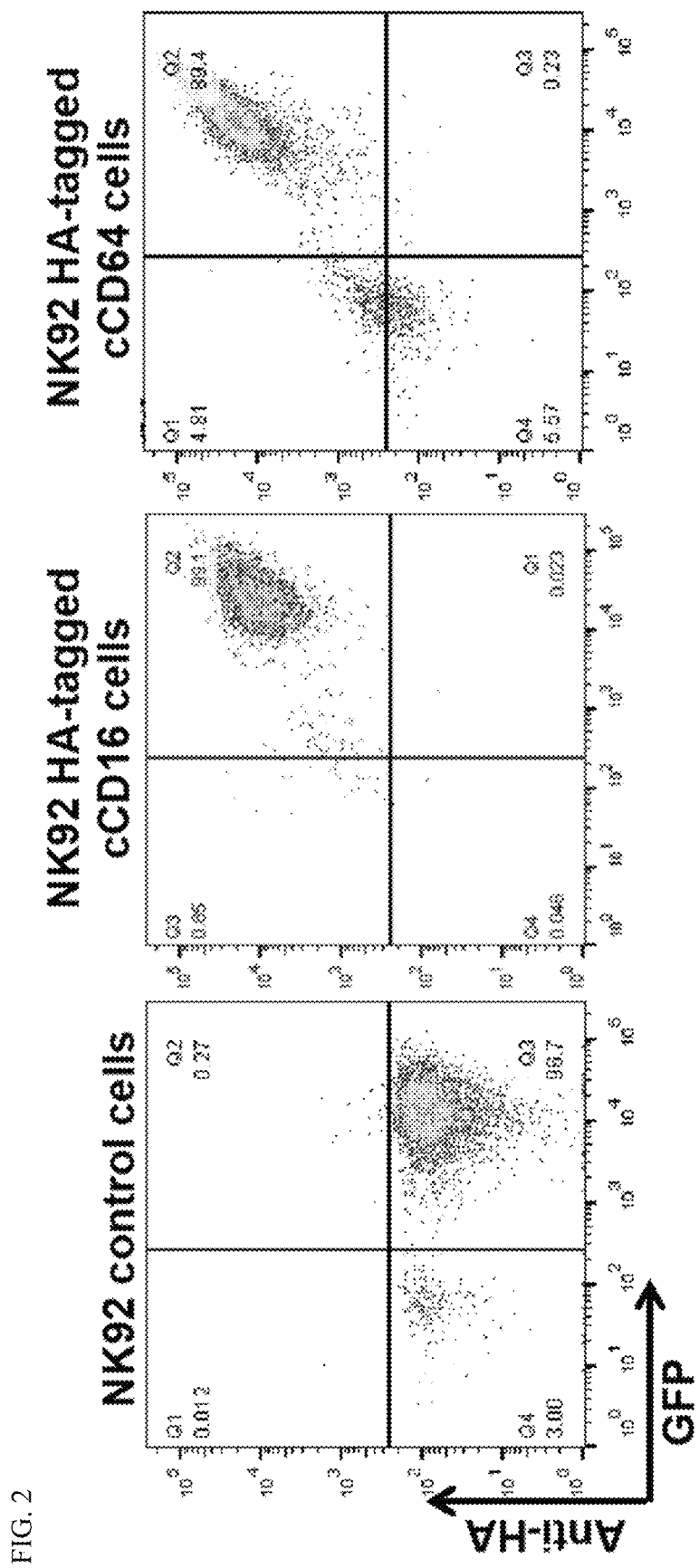
FIG. 2. Characterization of anti-canine CD16A and anti-canine CD64 mAbs. Flow cytometric analyses of NK-92 cells transduced with an empty vector (control cells), NK-92 canine CD16A (cCD16A) cells, and NK-92 canine CD64 (cCD64) cells stained with an anti-HA mAb.
Figure 3:
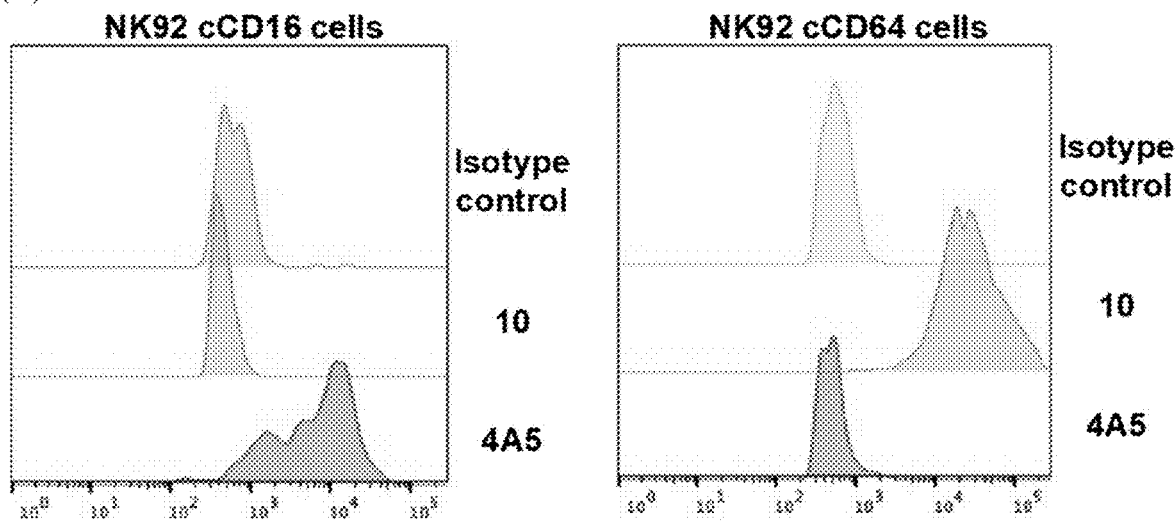
FIG. 3. Characterization of anti-canine CD16A and anti-canine CD64 mAbs. (A) Flow cytometric analyses of NK-92 cCD16A cells and NK-92 cCD64 cells stained with an isotype-matched negative control mAb, the anti-canine CD16A mAb (4A5), or the anti-canine CD64 mAb (10). (B) Western blot analysis of recombinant soluble canine CD16A, recombinant soluble canine CD64, or soluble human CD177 (negative control) using the mAbs 4A5 or 10. Equal protein loading was confirmed by BCA. All data are representative of three independent experiments.
Figure 3:
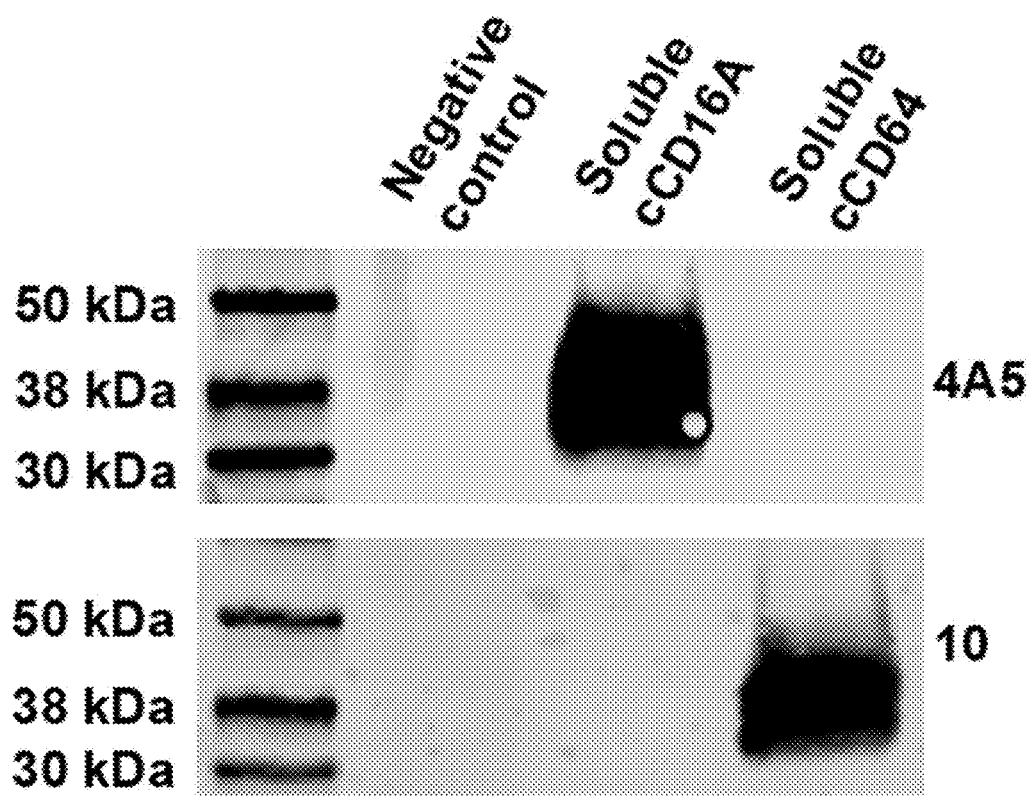

This disclosure reports the expression of soluble forms of canine CD16A and canine CD64, the screening and identification of monoclonal antibodies that specifically bind to canine CD16A or canine CD64, since initial experiments failed to produce specific reactivity to dog leukocytes by LNK16 and several other anti-human CD16 or CD64 mAbs. An anti-CD16A mAb (clone 4A5) and an anti-CD64 mAb (clone 10) were used in all analyses described below. The human NK cell line NK-92 was used to stably express intact versions of canine CD16A or canine CD64. NK-92 cells lack expression of any endogenous FcγRs. The canine CD16A and canine CD64 expression constructs were engineered with an N-terminus HA-tag for detection, as illustrated in FIG. 1. The retroviral vector used for transduction also expressed eGFP as a separate protein for an additional marker (FIG. 2). As shown in FIG. 3A, the anti-CD16A mAb clone 4A5 (IgG1) demonstrated selective reactivity with NK-92 canine CD16A cells and the anti-CD64 mAb clone 10 (IgG1) demonstrated selective reactivity with NK-92 canine CD64 cells. Neither mAb stained NK-92 control cells (FIG. 3A). FIG. 3B shows similar specificity in Western blot analysis against recombinant soluble canine CD16A (clone 4A5) and CD64 (clone 10) by Western bl (FIG. 3B).

Expression of CD16A and CD64 by Canine Leukocytes

Figure 4:
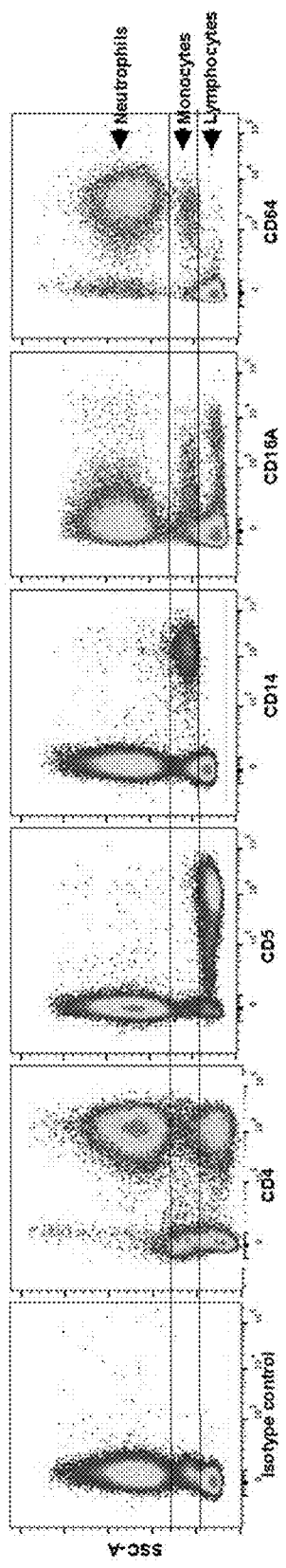
FIG. 4. CD16A and CD64 expression by canine leukocyte subsets. (A) Canine peripheral blood leukocytes were stained for the indicated markers and examined by flow cytometry. The y-axis=light side scatter area (SSC-A) and the x-axis=Log 10 fluorescence. All data are representative of three independent experiments using leukocytes from separate canine donors. (B) CD16A expression on CD5$^-$ and CD5$^+$ lymphocytes. For each dog examined, CD16A versus CD5 staining of lymphocytes was determined (left panel). From this plot, all CD16$^+$ lymphocytes were gated on and their expression of CD3 versus CD5 was examined. (C) Expression of CD94 by CD3$^-$ CD16$^+$ lymphocytes. CD3$^-$ CD16$^+$ lymphocytes were gated on (left panel) and the relative staining levels of CD94 were determined (right panel). The data are representative of three independent experiments using leukocytes from separate canine donors.
Figure 4:
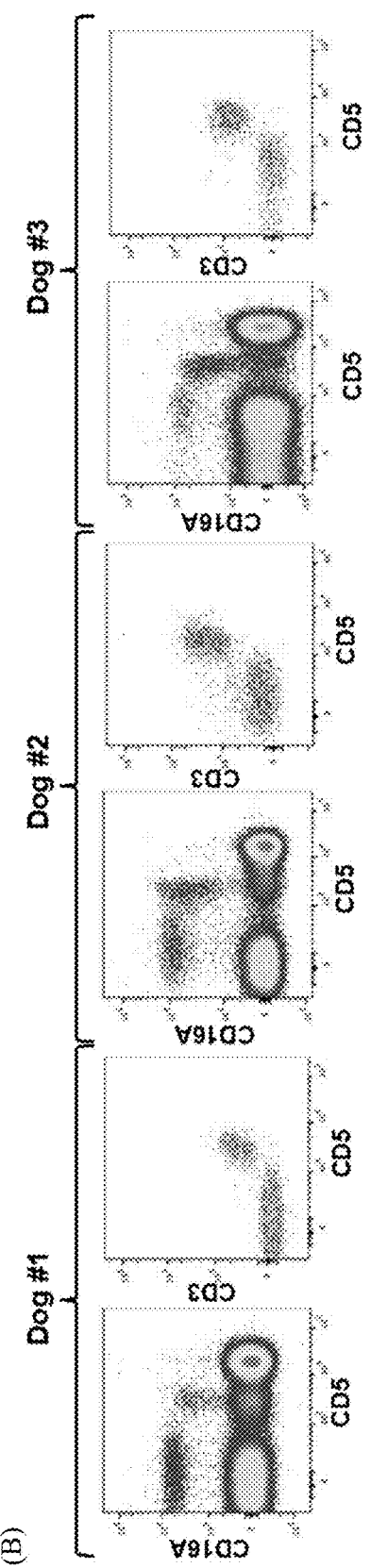
Figure 4:
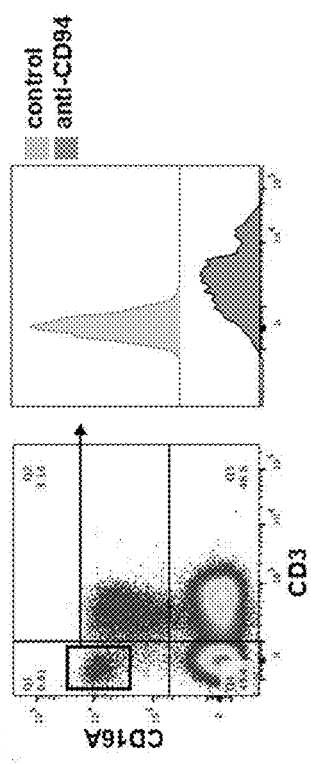

Flow cytometry was used to examine the expression patterns of CD16A and CD64 by dog peripheral blood leukocytes. The general leukocyte populations of polymorphonuclear cells (PMNs), monocytes, and lymphocytes were identified based on their characteristic forward and side light-scattering and by their expression of well characterized markers, including CD4 (neutrophils and lymphocyte), CD14 (monocytes), and CD5 (T cells) (FIG. 4A). The anti-canine CD16A clone 4A5 stained a subset of monocytes and lymphocytes, and for some dogs it marginally stained PMNs and/or a small subset of cells in this population (FIG. 4A). This staining pattern was consistent for all the anti-canine CD16 mAbs generated, which had distinct complementarity-determining region nucleotide sequences from 4A5. In contrast to the expression pattern of CD16A, the anti-canine CD64 clone 10 stained essentially all PMNs and monocytes (FIG. 4A). With some dogs, a small unstained population of PMNs (FIG. 4A). Taken together, the expression patterns of CD16A and CD64 on dog peripheral blood leukocytes were very similar to that of their orthologues on human peripheral blood leukocytes, as previously reported (Patel et al., *Front Immunol* 10:223, 2019).

Figure 5:
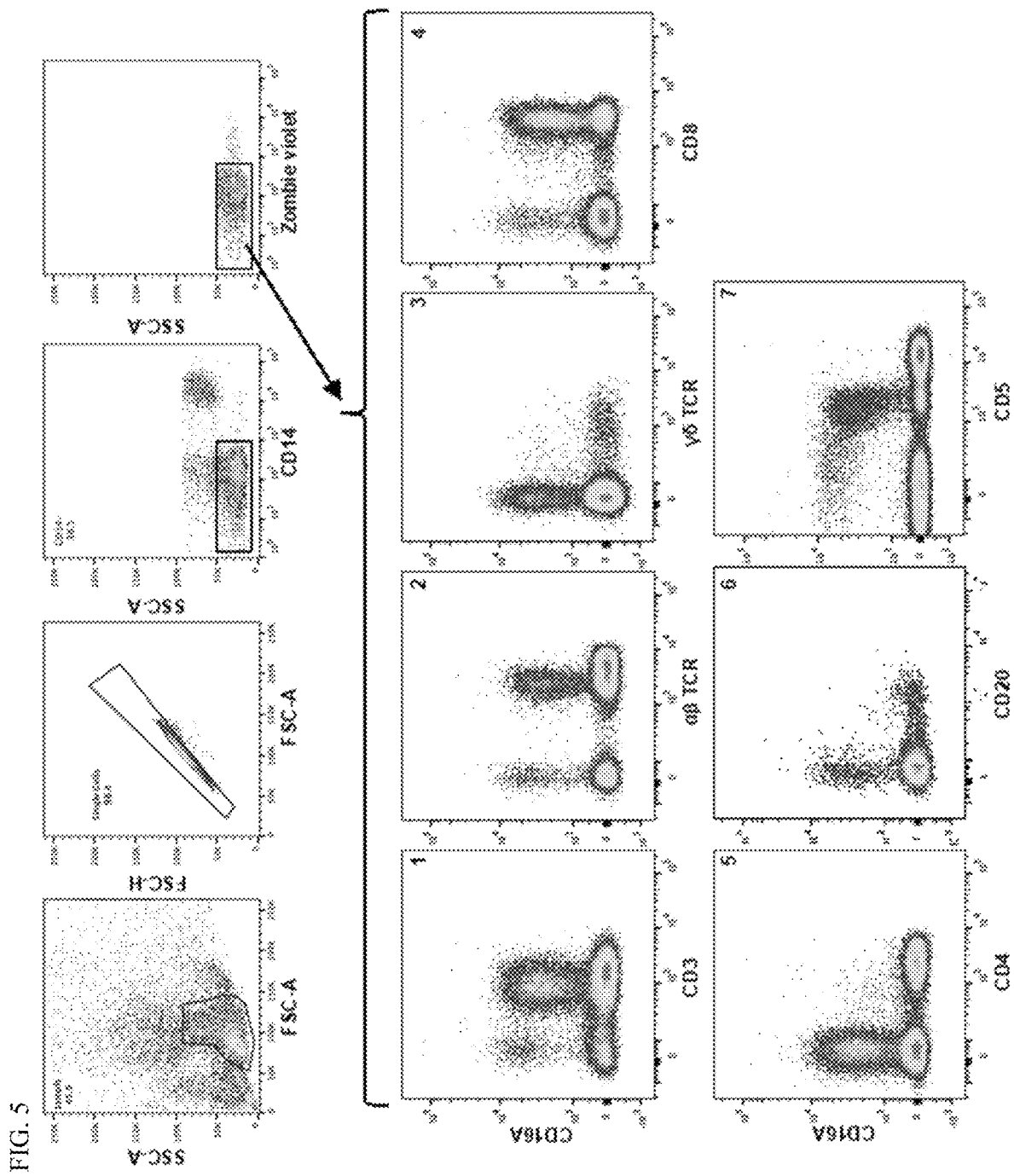
FIG. 5. CD16A and CD64 expression by canine leukocyte subsets. CD16A is expressed by T cells and non-B cell, non-T cell lymphocytes. The top panels show the gating strategy on peripheral blood mononuclear cells to examine single cell, viable, lymphocytes. The bottom panels show the expression of CD16A on various lymphocyte populations using the indicated markers. All data are representative of at least three independent experiments using leukocytes from separate canine donors.

Next, dog peripheral blood lymphocytes were examined to determine which subsets expressed CD16A based on available phenotypic markers. To assess expression of CD16A on T cells, mAbs to canine α/β TCR, γ/δ TCR, CD8, CD4, and CD3 were used. Canine CD16A$^+$ was expressed on T cells (FIG. 5). Moreover, CD3$^+$ CD16A$^+$ T cells (FIG. 5, panel 1) represented 3.08% (±1.94% SD) of the peripheral blood lymphocytes in the group of dogs that were examined (n=12). Moreover, CD16A$^+$ lymphocytes primarily expressed an α/β TCR versus γ/δ TCR (FIG. 5, panels 2 and 3) and CD8 versus CD4 (FIG. 5, panels 4 and 5). CD16A expression was also observed on CD3$^-$ lymphocytes (FIG. 5, panel 1) as well as α/β TCR$^-$ lymphocytes (FIG. 5, panel 2), which usually was a smaller subset than CD3$^+$ CD16A$^+$ T cells and consisted of 1.23%±0.97% SD, n=12) of the peripheral blood lymphocytes. B cells were identified by their expression of CD20 and CD22 and essentially none of these cells expressed CD16A (FIG. 5, panel 6).

In dogs, CD5 is typically classified as a canine T cell marker and is expressed at varying densities, referred to as CD5$^{dim}$ and CD5$^{bright}$ (Gingrich et al., *J Clin Med* 8:11, 2019). CD16A expression was detected on CD5$^-$ and CD5$^{dim}$ lymphocytes, but not on CD5$^{bright}$ lymphocytes (FIG. 5, panel 7). In most dogs, CD5$^{dim}$ CD16A$^+$ lymphocytes were the predominant population observed, but in some dogs CD5$^-$ CD16A$^+$ lymphocytes were an equivalent or the predominant population (FIG. 4B). Within the CD16A$^+$ lymphocyte population, CD5 levels corresponded with CD3 levels (FIG. 4B). Thus, CD16A$^+$ lymphocytes were either CD3$^+$ CD5$^{dim}$ or CD3$^-$ CD5$^-$. In humans, the non-B cell, CD3$^-$ CD5$^-$ CD16A$^+$ lymphocyte population represents NK cells. Unlike humans, CD56 is not an NK cell marker in dogs. CD94 is a broad marker of human NK cells. CD94 was expressed by the majority of CD3$^-$ CD16A$^+$ lymphocytes (FIG. 4C). The above findings thus indicate that CD16$^+$ lymphocytes in the dog consist of NK cells and T cells, and that the latter is the predominant population, which contrasts with humans.

Ectodomain Shedding of Canine CD16A

Figure 6:
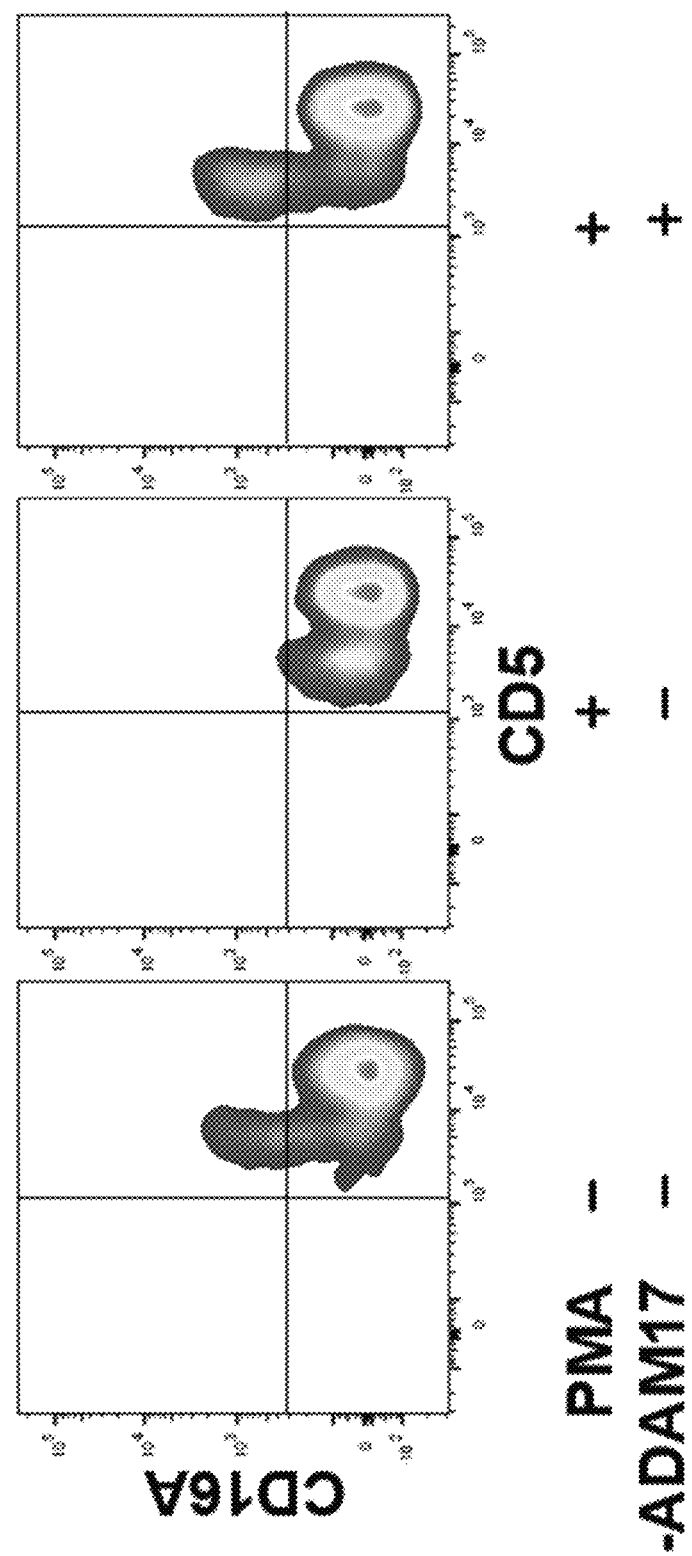
FIG. 6. Canine CD16A is downregulated by ADAM17 upon lymphocyte activation. Canine peripheral blood mononuclear cells were treated with or without PMA in the presence or absence of an ADAM17 function blocking mAb. Relative cell-staining levels of CD16A on CD5$^{dim}$ or CD5$^{bright}$ cells were determined by flow cytometry. All density plots show representative data of three independent experiments using leukocytes from separate canine donors.

Human CD16A undergoes a rapid downregulation in expression by a proteolytic process mediated by a disintegrin and metalloproteinase-17 (ADAM17) upon cell activation with various stimuli. For instance, the treatment of human leukocytes with the phorbol ester PMA induces efficient CD16A downregulation by ADAM17. Similarly, canine CD16A is downregulated upon activation of canine leukocytes with PMA. FIG. 6 shows CD16A levels on CD5$^{dim}$ lymphocytes before and after PMA activation. ADAM17 activity in dog neutrophils can be blocked by an anti-ADAM17 mAb, as previously reported (Snyder et al., *Vet Immunol Immunopathol* 231:110162, 2021). This anti- ADAM17 mAb also blocked the downregulation of CD16A on activated canine lymphocytes (FIG. 6). Taken together, the data reveal similar regulation of human and canine CD16A by ADAM17, a process that does not occur for mouse CD16.

Induction of ADCC by canine CD16A and CD64

Figure 7:
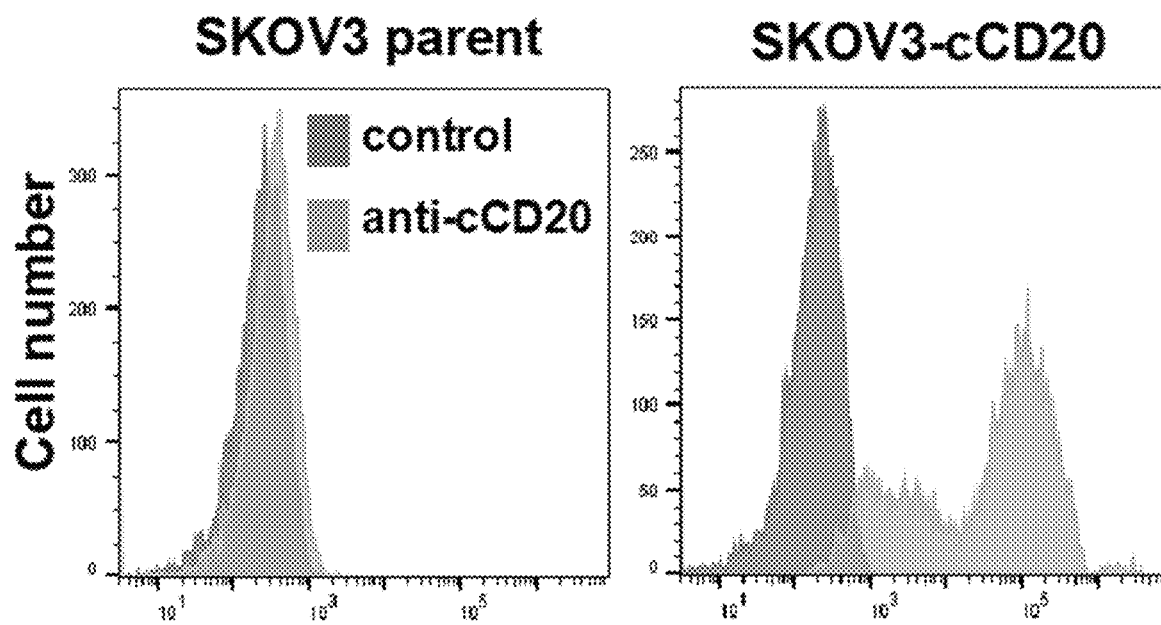
FIG. 7. NK-92 cells expressing canine CD16A mediate ADCC. (A) SKOV-3 parental cells and SKOV-3-canine CD20 (cCD20) cells were stained with an anti-canine CD20 mAb or an isotype-matched negative control mAb (control) and examined by flow cytometry. (B) Schematic representation of antibody-dependent cellular cytotoxicity (ADCC). SKOV-3-canine CD20 cells treated with a caninized anti-canine CD20 mAb in the presence of NK-92-canine CD16A (cCD16A) cells.
Figure 7:
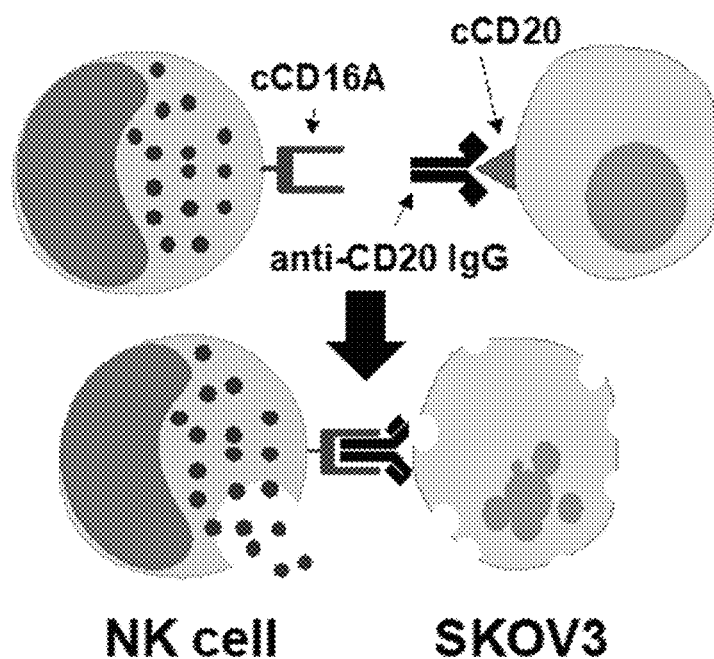
Figure 8:
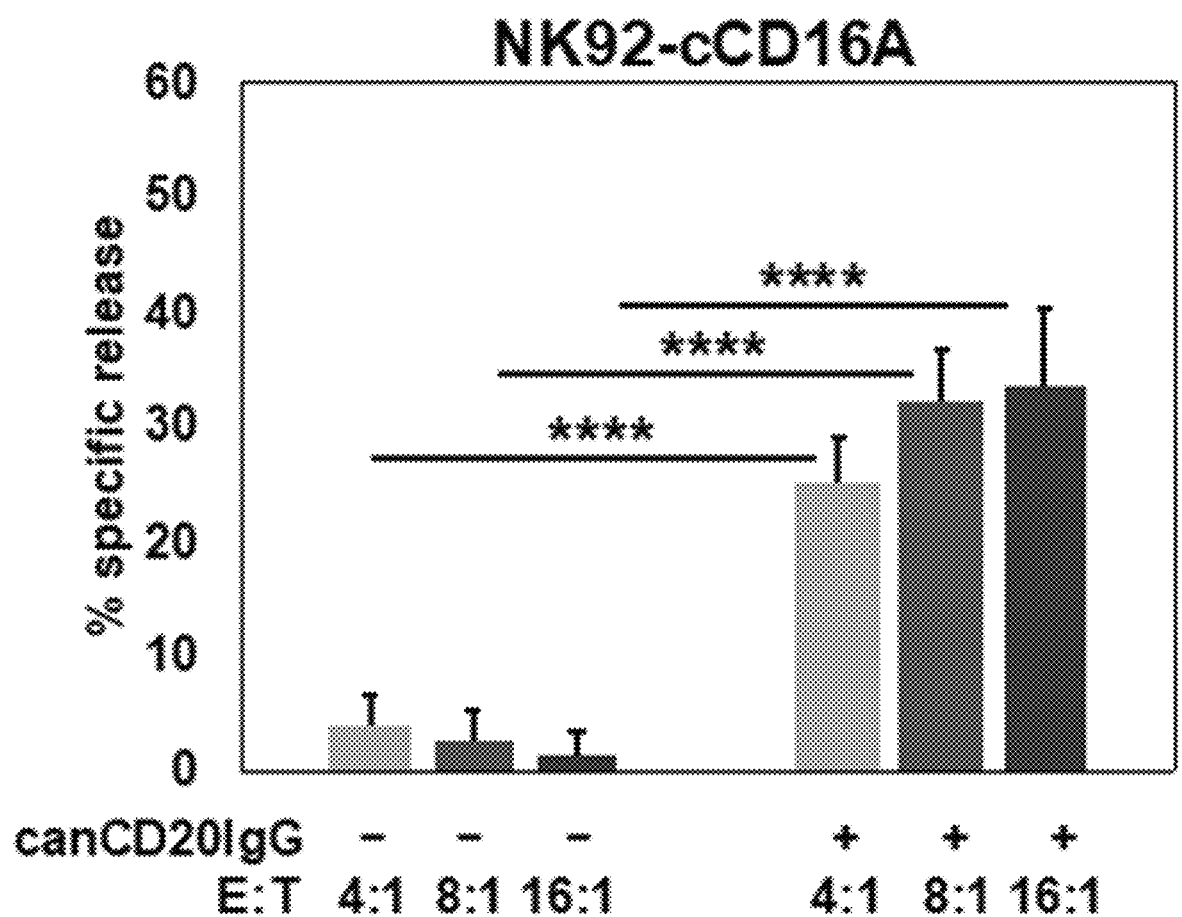
FIG. 8 NK-92 cells expressing canine CD16A mediate antibody-dependent cellular cytotoxicity (ADCC). NK-92 canine CD16A cells were incubated with SKOV-3 canine CD20 cells at the indicated E:T ratios in the presence or absence of a caninized anti-canine CD20 mAb for two hours at 37° C. Data are represented as % specific release and the mean±SD of three independent experiments is shown. Statistical significance is indicated as ****p<0.0001.

Human CD16A is a potent activating receptor that induces antibody-dependent cell-mediated cytotoxicity (ADCC) upon engaging antibodies attached to target cells. To test whether canine CD16A could induce ADCC, NK-92 cells were transduced with intact canine CD16A. Canine CD16A expression was verified using the anti-canine CD16A mAb 4A5. To avoid a xenogeneic response between NK-92 cells and canine target cells, the human ovarian cancer cell line SKOV-3 transduced to express canine CD20 was used as target cell (FIG. 7A). Like human IgGs, canine IgGs consist of four subclasses (IgG 1, 2, 3, and 4 also referred to as A, B, C, and D). Canine IgG2 (IgGB) is the functional analog of human IgG1 and it binds to canine CD16A and canine CD64. To target canine CD20, a commercially available "caninized" mAb containing a canine IgG2 Fc region was used (FIG. 7B). NK-92 cells expressing canine CD16A mediated significantly higher levels of cytolysis in the presence of the anti-CD20 mAb when compared to cells in the absence of the anti-CD20 mAb at various effector:target (E:T) ratios (FIG. 8).

Figure 9:
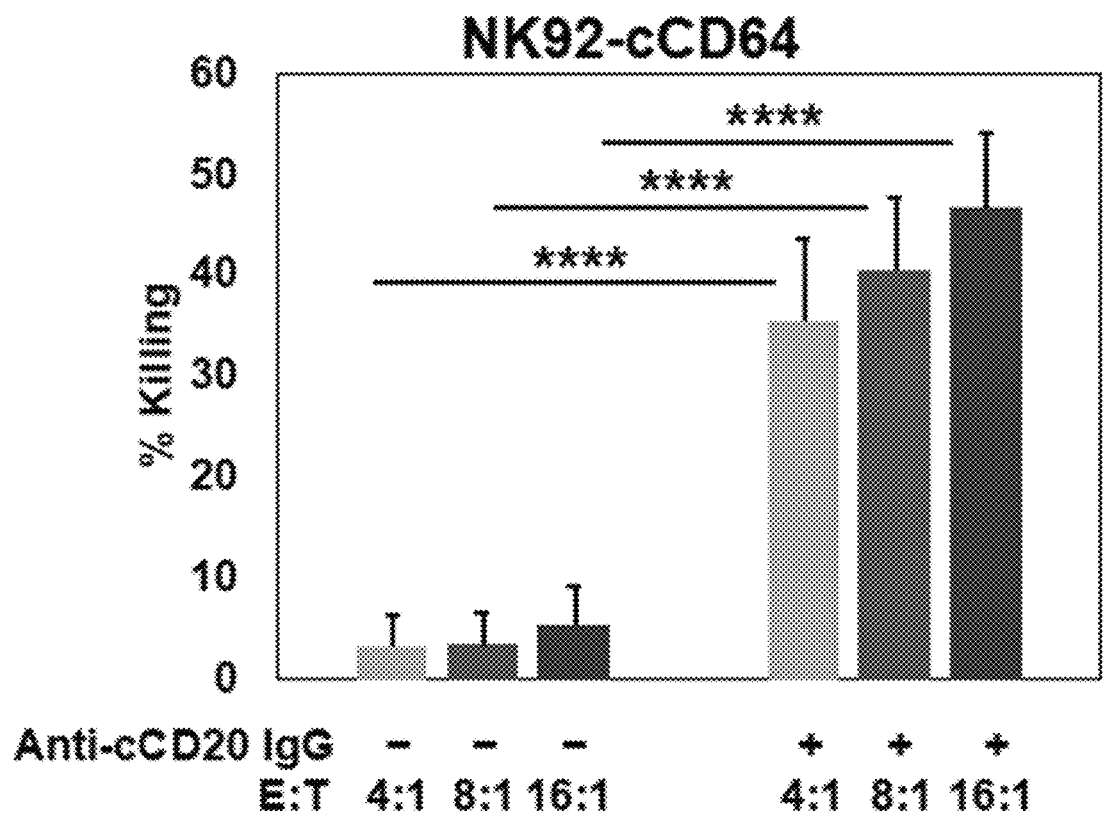
FIG. 9. NK-92 cells expressing canine CD64 mediate ADCC when armed with a tumor-targeting mAb. (A) NK-92 canine CD64 (cCD64) cells were incubated with SKOV-3 canine CD20 cells at the indicated E:T ratios in the presence or absence of a caninized anti-canine CD20 mAb for two hours at 37° C. Data are represented as % specific release and the mean±SD of three independent experiments is shown. Statistical significance is indicated as ****p<0.0001. (B) NK-92 cCD16A and NK-92 cCD64 cells were incubated with or without biotinylated canine IgG at various concentrations for one hour at 37° C., washed, stained with a fluorophore-conjugated streptavidin, and analyzed by flow cytometry. Data are representative of at least three independent experiments.
Figure 9:
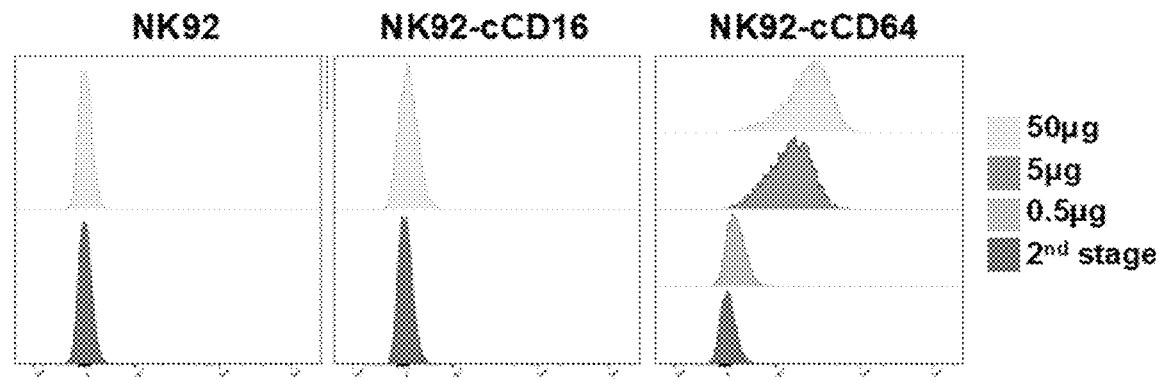
Figure 10:
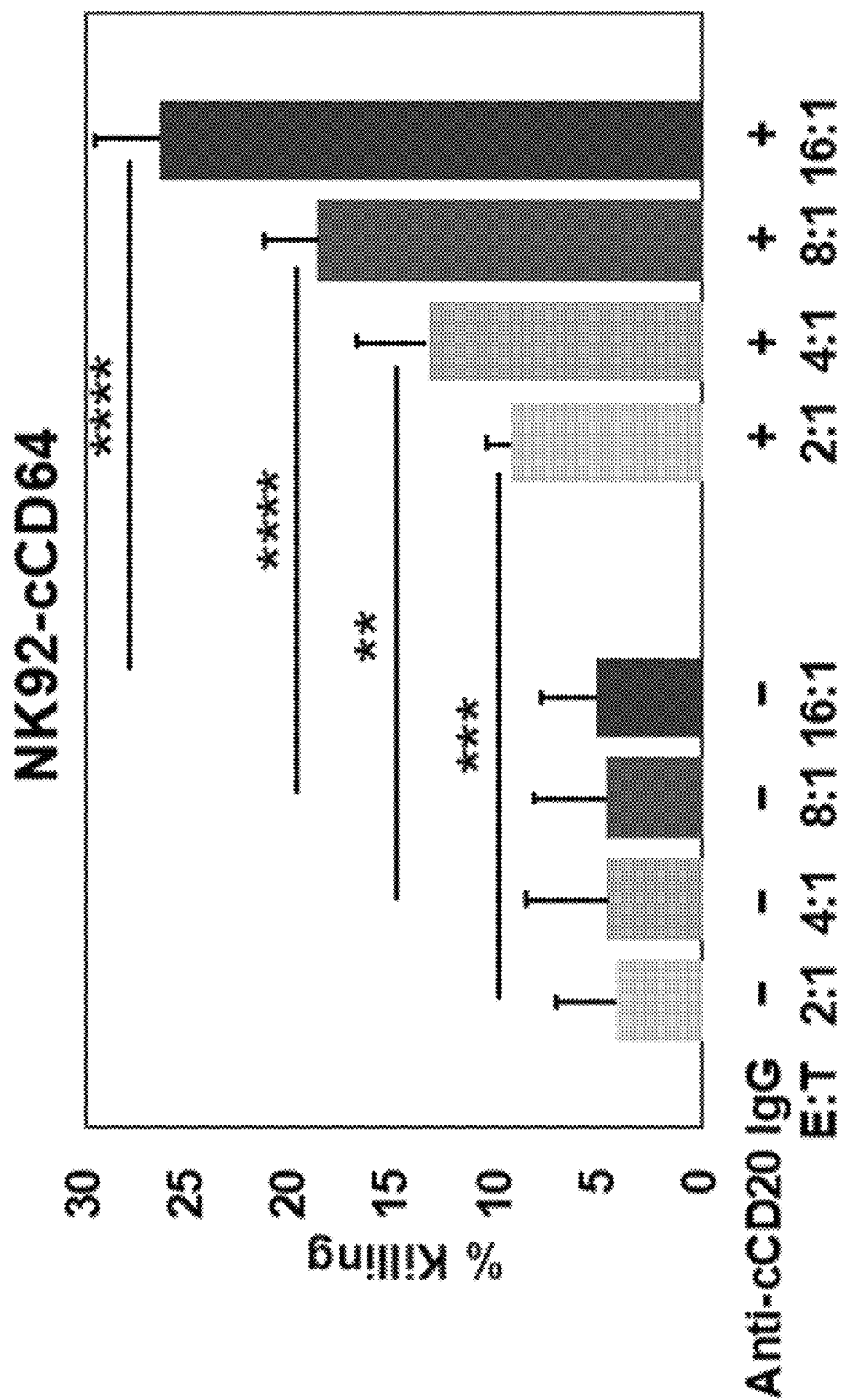
FIG. 10. NK-92 cells expressing canine CD64 mediate ADCC when armed with a tumor-targeting mAb. NK-92 canine CD64 cells were incubated in the presence or absence of caninized anti-canine CD20 mAb (5 g/ml), washed, and exposed to SKOV-3 canine CD20 cells at the indicated E:T ratios for two hours at 37° C. Data are represented as % specific release and the mean±SD of three independent experiments is shown. Statistical significance is indicated as p<0.01, *p<0.001, ****p<0.0001.

Human CD16A and canine CD16A bind to IgG with low affinity and have reduced avidity when downregulated by ADAM17 upon NK cell activation. These events may serve as checkpoint processes for maintaining immune homeostasis, but are also likely to reduce the efficacy of anti-tumor therapeutic mAbs. To bypass these checkpoint processes of CD16A, human NK cells can be engineered with recombinant versions of CD64, the high affinity FcγR. Human CD64 and canine CD64 bind to the same IgG isotypes as CD16A and signals via a noncovalent association with FcRγ and/or CD3ζ. Moreover, CD64 is not cleaved by ADAM17. FIG. 9A shows that NK-92 cells expressing canine CD64 effectively mediate ADCC of SKOV-3 canine CD20 cells in the presence of a caninized anti-CD20 mAb. Due to the high affinity state of CD64, engineered NK-92 cells expressing human CD64 could be armed with tumor-targeting mAbs and mediate ADCC. NK-92 cells expressing canine CD64 also effectively bound soluble monomeric canine IgG when compared to NK-92 cells expressing canine CD16A (FIG. 9B). Additionally, NK-92 cells expressing canine CD64 could be armed with a caninized anti-CD20 mAb to mediate ADCC of SKOV-3-cCD20 cells (FIG. 10). Collectively, the data demonstrate that canine CD64 can induce ADCC by NK-92 cells, similar to human CD64.

Human CD64 and CD16A promote effector activity of anti-tumor therapeutic mAbs. Both FcγRs have been cloned from dog leukocytes and their IgG binding characteristics examined. However, their expression patterns on dog leukocytes have not been determined. This disclosure describes generating mAbs specific to canine CD64 and canine CD16A to reveal expression patterns of canine CD16A and canine CD64 in myeloid and lymphoid leukocyte populations in the dog, which in general are similar to humans. A closer look at canine lymphocytes revealed CD16A expression on CD3$^+$ T cells and CD3$^-$ lymphocytes, but not on B cells. The CD16A$^+$ lymphocytes were also primarily α/β TCR$^+$ and CD8$^+$. Interestingly, canine CD16A$^+$ lymphocytes were predominantly in the CD3$^+$ fraction, whereas in humans, CD16A$^+$ lymphocytes primarily occur in the CD3$^-$ fraction. The proportion of α/β TCR$^+$ CD8$^+$ CD16A$^+$ T cells in humans can increase during certain viral infections and these cells demonstrated NK cell properties.

Canine NK cells are phenotypically distinguished based on their lack of the B cell markers CD3, CD4, and TCRs. CD5$^{bright}$ lymphocytes in the dog have been classified as T cells, but there are conflicting views on CD5 expression by canine NK cells, which has been reported as CD5$^{+/-}$ and CD5$^{dim}$. Both CD5$^{+/-}$ and CD5$^{dim}$ populations have been shown to mediate natural cytotoxicity and ADCC. This disclosure shows CD5 expression levels on CD16A$^+$ lymphocytes ranged from negative to dim, which directly corresponded with their levels of CD3 expression. Thus, canine CD16A$^+$ lymphocytes appear to include CD3$^+$ CD5$^{dim}$ T cells and CD3$^-$ CD5$^-$ CD20$^-$ (or CD22$^-$) lymphocytes. Canine NK cell markers detected by antibodies include CD94 and NKp46. This disclosure shows that CD3$^-$ CD16A$^+$ lymphocytes are primarily CD94$^+$. Canine peripheral blood NK cells include NKp46$^+$ and NKp46$^-$ cells and its expression indicates recent activation and expansion. Using a commercially available anti-canine NKp46 mAb, considerable variability in its staining of dog peripheral blood lymphocytes was observed, which often did not stain above an isotype-matched negative control mAb. As is the case in humans, CD16A may represent a pan-marker of mature NK cells in the peripheral blood of dogs.

This disclosure directly shows that canine CD16A can induce ADCC when expressed in the human NK cell line NK-92. Others have reported that NK-92 cells expressing a canine CD16A fusion protein consisting of the extracellular region of canine CD16A and the transmembrane and intracellular regions of canine FcRγ also mediated ADCC (Mizuno et al., Vet *Immunol Immunopathol* 240:110315, 2021). Human CD16A signaling is normally mediated by a noncovalent association with the signaling adapters FcRγ and/or CD3ζ. NK-92 cells express FcRγ and CD3ζ, and therefore canine CD16A likely associated with these signaling adaptors to induce ADCC. Indeed, seven amino acids in the transmembrane region of human CD16A involved in FcRγ and CD3(association are conserved in the transmembrane region of canine CD16A (FIG. 11, boxed residues).

An effector function of several clinically successful mAbs targeting tumors is antibody-dependent cell-mediated cytotoxicity (ADCC). However, CD16A undergoes rapid shedding from the cell surface of NK cells by ADAM17 following its signaling or by various other stimuli. This appears to reduce the efficacy of tumor mAb therapies, especially in an immunosuppressive tumor microenvironment. Indeed, CD16A downregulation occurs on NK cells in the tumor microenvironment. ADAM17 activity has been demonstrated in canine leukocytes, and data reported herein show that blocking the metalloprotease inhibited CD16A downregulation upon canine lymphocyte activation. Human NK cells expressing a non-cleavable version of CD16A or upon blocking ADAM17 activity demonstrated increased killing of tumor cells by ADCC and production of IFNγ, and thus this may be an approach to enhance ADCC by CD16A$^+$ canine lymphocytes.

Another property of CD16A that appears to decrease the efficacy of mAb therapies is that it is a low affinity member of the FcγR family. Indeed, clinical studies in humans have shown that increasing the affinity by which NK cells engage anti-tumor mAbs significantly improved patient outcome. This is an active area of research that includes approaches such as modifying the Fc region of anti-tumor antibodies or the FcγR on NK cells. For the latter, human NK cells have been engineered to express recombinant versions of human CD64, a high affinity IgG Fc receptor in humans and dogs.

Human CD64 is normally expressed by myeloid cells, but not NK cells; the same CD64 expression pattern exists in dogs. Similar to canine CD16A, canine CD64 expression in NK-92 cells induced ADCC, and due to its high affinity state, monomeric canine IgG could be adsorbed to these cells. Additionally, NK-92-canine CD64 cells armed with a caninized anti-canine CD20 mAb effectively killed target cells expressing canine CD20. Primary dog NK cells can also be engineered to express canine CD64 to maximize their ADCC potency. These cells could provide an off-the-shelf adoptive cell therapy option used in combination with assorted anti-tumor targeting mAbs for broad tumor antigen targeting and treating various malignancies. This approach may have advantages over the time and cost required to modify the Fc region of individual anti-tumor mAbs to enhance their binding affinity to CD16A, a receptor, as mentioned above, that is also subject to downregulation upon NK cell activation.

Having established the expression of canine CD16A and canine CD64, including in recombinant NK cells, this disclosure describes anti-canine CD16A polypeptides that specifically bind to canine CD16A and further describes anti-canine CD64 polypeptides that specifically bind to canine CD64. As used herein, the term "anti-canine CD16A polypeptide" includes polypeptides structurally similar to any one of SEQ ID NO:5 through SEQ ID NO:12. Further, the term "anti-canine CD64 polypeptide" includes polypeptides structurally similar to any one of SEQ ID NO:13 through SEQ ID NO:20.

As used herein, a polypeptide is "structurally similar" to a reference polypeptide if the amino acid sequence of the polypeptide possesses a specified amount of identity compared to the reference polypeptide. Structural similarity of two polypeptides can be determined by aligning the residues of the two polypeptides (for example, a candidate polypeptide and the polypeptide of, for example, any one of SEQ ID NO:5 through SEQ ID NO:20) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate polypeptide is the polypeptide being compared to the reference polypeptide (e.g., any one of SEQ ID NO:5 through SEQ ID NO:20). A candidate polypeptide can be isolated, for example, from an animal, or can be produced using recombinant techniques, or chemically or enzymatically synthesized.

A pair-wise comparison analysis of amino acid sequences can be carried out using the BESTFIT algorithm in the GCG package (version 10.2, Madison WI). Alternatively, polypeptides may be compared using the Blastp program of the BLAST 2 search algorithm, as described by Tatiana et al., (FEMS Microbiol Lett, 174, 247-250 (1999)), and available on the National Center for Biotechnology Information (NCBI) website. The default values for all BLAST 2 search parameters may be used, including matrix=BLOSUM62; open gap penalty=11, extension gap penalty=1, gap x_dropoff=50, expect=10, wordsize=3, and filter on.

In the comparison of two amino acid sequences, structural similarity may be referred to by percent "identity" or may be referred to by percent "similarity." "Identity" refers to the presence of identical amino acids. "Similarity" refers to the presence of not only identical amino acids but also the presence of conservative substitutions. A conservative substitution for an amino acid in a reference polypeptide may be selected from other members of the class to which the amino acid belongs. For example, it is well-known in the art of protein biochemistry that an amino acid belonging to a grouping of amino acids having a particular size or characteristic (such as charge, hydrophobicity and hydrophilicity) can be substituted for another amino acid without altering the activity of a protein, particularly in regions of the protein that are not directly associated with biological activity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine, and glutamine. The positively charged (basic) amino acids include arginine, lysine, and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free —OH is maintained; or Gln for Asn to maintain a free —NH$_2$. Likewise, biologically active analogs of a polypeptide containing deletions or additions of one or more contiguous or noncontiguous amino acids that do not eliminate a functional activity of the polypeptide are also contemplated.

An anti-canine CD16A polypeptide as described herein can include a polypeptide with at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence similarity to any one of SEQ ID NO:5, SEQ ID NO:6, SEQ ID NO:7, SEQ ID NO:8, SEQ ID NO:9, SEQ ID NO: 10, SEQ ID NO: 11 (DTS), or SEQ ID NO: 12.

An anti-canine CD16A polypeptide as described herein can include a polypeptide with at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any one of SEQ ID NO:5, SEQ ID NO:6, SEQ ID NO:7, SEQ ID NO:8, SEQ ID NO:9, SEQ ID NO: 10, SEQ ID NO: 11 (DTS), or SEQ ID NO: 12.

An anti-canine CD64 polypeptide as described herein can include a polypeptide with at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence similarity to any one of SEQ ID NO:13, SEQ ID NO:14, SEQ ID NO:15, SEQ ID NO:16, SEQ ID NO:17, SEQ ID NO:18, SEQ ID NO:19, or SEQ ID NO:20.

An anti-canine CD64 polypeptide as described herein can include a polypeptide with at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any one of SEQ ID NO:13, SEQ ID NO:14, SEQ ID NO:15, SEQ ID NO:16, SEQ ID NO:17, SEQ ID NO:18, SEQ ID NO:19, or SEQ ID NO:20.

An anti-canine CD16A polypeptide or an anti-canine CD64 polypeptide as described herein also can be designed to provide additional sequences, such as, for example, the addition of added C-terminal or N-terminal amino acids that can, for example, facilitate purification by trapping on columns or use of antibodies. Such tags include, for example, histidine-rich tags that allow purification of polypeptides on nickel columns. Such gene modification techniques and suitable additional sequences are well known in the molecular biology arts.

In one or more embodiments, the anti-canine CD16A polypeptide or anti-canine CD64 polypeptide can be an antibody. As used herein, the term "antibody" refers generally an immunoglobulin or a fragment thereof. Thus, as used herein, the term "antibody" encompasses not only immunoglobulins with an intact Fc region, but also antibody fragments capable of binding to a biological molecule (such as an antigen or receptor) or a portion thereof, including but not limited to Fab, Fab' and F(ab')$_2$, pFc', Fd, a single domain antibody (sdAb), a variable fragment (Fv), a single-chain variable fragment (scFv) or a disulfide-linked Fv (sdFv); a diabody or a bivalent diabody; a linear antibody; a single-chain antibody molecule; and a multispecific antibody (e.g., a tribody) formed from antibody fragments. The antibody can be of any type (e.g., IgG, IgE, IgM, IgD, IgA and IgY), class (e.g., IgG1, IgG2, IgG3, IgG4, IgA1 and IgA2), or subclass.

Thus, for example, in one or more embodiments, the anti-canine CD16A polypeptide or anti-CD64 polypeptide can be a humanized antibody derived from an animal single domain antibody. While an scFv has a heavy variable chain component and a light variable chain component joined by a linking segment, a single domain antibody consists of a single monomeric variable chain—i.e., a variable heavy chin or a variable light chain—that is capable of specifically engaging a target. A single domain antibody may be derived from an antibody of any suitable animal such as, for example, a camelid (e.g., a llama or camel) or a cartilaginous fish. A single domain antibody can provide superior physical stability, an ability to bind deep grooves, and increased production yields compared to larger antibody fragments.

This disclosure describes anti-canine CD16 polypeptides, anti-canine CD64 polypeptides, compounds and devices that include an anti-canine CD16 polypeptide or an anti-canine CD64 polypeptide, and methods of using such compounds and devices. Exemplary platforms in which an anti-canine CD16 polypeptide or an anti-canine CD64 polypeptide may be used include, but are not limited to, chimeric antigen receptor therapies (e.g., CAR-NK therapy, CAR-T therapy, CAR-macrophage therapy, etc.), multispecific immune cell engager technologies (e.g., bispecific killer engagers, trispecific killer engagers, bispecific T cell engagers, trispecific T cell engagers, etc.), targeted immunotherapies (e.g., targeted ADAM17 blocker (TAB) therapy), delivery of therapeutics (e.g., antibody-drug conjugates, delivery of therapeutic radioisotopes, delivery of toxins, delivery of cytokines, delivery of chemokines), imaging technologies (delivery of labeling constructs and/or labeling radioisotopes), cell and/or ligand capture technologies (e.g., ELISA, etc.).

Multispecific immune cell engagers may, for example, be used clinically to bridge two cells together (e.g., an effector cell such as a leukocyte and a target cell such as a tumor cell or a cell infected by an infectious agent) and induce activation of the effector cells to kill the target cell. This is of particular importance considering immunotherapies, such as for cancer, are being rapidly developed for companion animals. For example, constructs containing an anti-canine CD16 polypeptide or an anti-canine CD64 polypeptide may be used to engage specific dog leukocyte populations and induce effector functions such as antibody-dependent cellular cytotoxicity (ADCC) and phagocytosis.

Multispecific compounds that include an anti-canine CD16A polypeptide or an anti-CD64 polypeptide can include one or more functional domains in addition to the anti-canine CD16A polypeptide or the anti-CD64 polypeptide. Functional domains of multispecific compounds can include, but are not limited to, a targeting domain that specifically binds to a target antigen or a target cell (e.g., a cell that expresses a target antigen), an immune cell engaging domain that specifically binds to an immune cell or a particular subset of immune cells, and/or an immune cell activating domain.

The targeting domain can include any moiety that selectively binds to an intended target such as, for example, a tumor antigen or an infectious antigen. As used herein, the erm "tumor antigen" refers to an antigen expressed by a tumor cell, in the cancer stroma, or by an immune inhibitory cell such as a myeloid derived suppressor cell. As used herein, the term "infectious antigen" refers to an antigen expressed by an infectious agent (a bacterium, virus, parasite, etc.) or by a cell infected by an infectious agent (e.g., a virally-infected cell). Thus, a targeting domain can include, for example, an anti-tumor antibody such as rituximab (anti-CD20), afutuzumab (anti-CD20), trastuzumab (anti-HER2/neu), pertuzumab (anti-HER2/neu), labetuzumab (anti-CEA), adecatumumab (anti-EpCAM), citatuzumab bogatox (anti-EpCAM), edrecolomab (anti-EpCAM), arcitumomab (anti-CEA), bevacizumab (anti-VEGF-A), cetuximab (anti-EGFR), nimotuzumab (anti-EGFR), panitumumab (anti-EGFR), zalutumumab (anti-EGFR), gemtuzumab ozogamicin (anti-CD33), lintuzumab (anti-CD33), etaracizumab (anti-integrin $\alpha_v\beta_3$), intetumumab (anti-CD51), ipilimumab (anti-CD152), oregovomab (anti-CA-125), votumumab (anti-tumor antigen CTAA16.88), or pemtumumab (anti-MUC1), anti-CD19, anti-CD22, anti-CD133, anti-CD38 anti-mesothelin, anti-ROR1, CSPG4, SS1, or IGFR1. In other exemplary embodiments, the targeting domain can selectively bind to a target on a cell infected by a virus such as, for example, an adenovirus, HIV, CMV, and/or HPV.

In one or more embodiments, the anti-canine CD16A polypeptide or the anti-CD64 polypeptide can perform the function of engaging an immune cell population. A multispecific compound that includes an anti-canine CD16A polypeptide or an anti-CD64 polypeptide can nevertheless include an additional immune cell engaging domain to engage immune cells in addition to those engaged via the anti-canine CD16A polypeptide or the anti-CD64 polypeptide. The immune cell engaging domain can include any moiety that binds to and/or activates an immune cell and/or any moiety that blocks inhibition of an immune cell. In one or more embodiments, the immune cell engaging domain can include an antibody that selectively binds to a component of the surface of an immune cell. In other embodiments, the immune cell engaging domain can include a ligand or small molecule that selectively binds to a component of the surface of an immune cell.

In one or more embodiments, the immune cell engaging domain can selectively bind to a receptor at least partially located at the surface of an immune cell. In certain embodiments, the immune cell engaging domain can serve a function of binding an immune cell and thereby bring the immune cell into spatial proximity with a target to which the targeting domain-described in more detail above-selectively binds.

In one or more embodiments, the immune cell activating domain can include a cytokine, a functional fragment of a cytokine, or a variant of cytokine that possesses immune cell activating activity. Exemplary cytokines include, but are not limited to IL-12 (SEQ ID NO:45 and SEQ ID NO:46), IL-15 (e.g., SEQ ID NO:47 or a variant thereof such as a variant having an N72D or an N72A amino acid substitution compared to SEQ ID NO:47), IL-18, IL-21, IL-4, IL-2, IL-6, IL-7, IL-8, IL-9, IL-21, and IL-13, IFN-7, GM-CSF, TGF-β, and/or TNF-α.

For therapeutic applications in which the immune cell activating domain includes a polypeptide, it may be preferred in one or more embodiments that the polypeptide is from, or is derived from, a protein expressed by the same species as the subject to whom the anti-canine CD16A polypeptide or the anti-CD64 polypeptide will be administered. Thus, for example, if the anti-canine CD16A polypeptide or the anti-CD64 polypeptide is intended to be administered to a human, then the immune cell activating domain can include a human polypeptide or be derived from a human polypeptide (e.g., a human cytokine or a variant of human cytokine that possesses immune cell activating activity). As another example, if the anti-canine CD16A polypeptide or the anti-CD64 polypeptide is intended to be administered to a canine, then the immune cell activating domain can include a canine polypeptide or be derived from a canine polypeptide (e.g., a canine cytokine or a variant of canine cytokine that possesses immune cell activating activity).

Functional domains may be linked using linking segments known in the art for linking domains of fusion polypeptides. Nonlimiting examples of suitable linking segments are included in SEQ ID NO:33 through SEQ ID NO:44.

Thus, this disclosure describes methods of treating a subject having, or at risk of having, a condition treatable with an anti-canine CD16A polypeptide or an anti-canine CD64 polypeptide. Generally, the methods involve administering as anti-canine CD16A polypeptide or an anti-canine CD64 polypeptide, as appropriate for the condition being treated, to a subject in need of treatment. The condition may be, for example, a cancer or an infectious condition. As used herein, "treat" or variations thereof refer to reducing, limiting progression, ameliorating, or resolving, to any extent, the symptoms or signs related to a condition. A "treatment" may be therapeutic or prophylactic. "Therapeutic" and variations thereof refer to a treatment that ameliorates one or more existing symptoms or clinical signs associated with a condition. "Prophylactic" and variations thereof refer to a treatment that limits, to any extent, the development and/or appearance of a symptom or clinical sign of a condition. Generally, a "therapeutic" treatment is initiated after the condition manifests in a subject, while "prophylactic" treatment is initiated before a condition manifests in a subject.

Treatment that is prophylactic is referred to herein as treatment of a subject that is "at risk" of having the condition. As used herein, the term "at risk" refers to a subject that may or may not actually possess the described risk. Thus, for example, a subject "at risk" of infectious condition is a subject present in an area where other individuals have been identified as having the infectious condition and/or is likely to be exposed to the infectious agent even if the subject has not yet manifested any detectable indication of infection by the microbe and regardless of whether the subject may harbor a subclinical amount of the microbe. As another example, a subject "at risk" of a non-infectious condition is a subject possessing one or more risk factors associated with the condition such as, for example, genetic predisposition, ancestry, age, sex, geographical location, lifestyle, or medical history. Treatment may also be continued after symptoms have resolved, for example to prevent or delay their recurrence.

Accordingly, a composition can be administered before, during, or after the subject first exhibits a symptom or clinical sign of the condition or, in the case of infectious conditions, before, during, or after the subject first comes in contact with the infectious agent. Treatment initiated before the subject first exhibits a symptom or clinical sign associated with the condition may result in decreasing the likelihood that the subject experiences clinical evidence of the condition compared to a subject to which the composition is not administered, decreasing the severity of symptoms and/or clinical signs of the condition, and/or completely resolving the condition. Treatment initiated after the subject first exhibits a symptom or clinical sign associated with the condition may result in decreasing the severity of symptoms and/or clinical signs of the condition compared to a subject to which the composition is not administered, and/or completely resolving the condition.

Thus, the method includes administering an effective amount of the composition to a subject having, or at risk of having, a particular condition. As used herein, an "effective amount" is an amount effective to reduce, limit progression, ameliorate, or resolve, to any extent, a symptom or clinical sign related to the condition. In one or more embodiments, an "effective amount" is an amount effective to increase antibody-dependent cellular toxicity (ADCC) in a subject compared to a comparable subject to whom the composition is not administered.

The subject can be a human or an appropriate non-human animal such as, for example, a livestock animal or a companion animal. Exemplary non-human animal subjects include, but are not limited to, animals that are hominid (including, for example chimpanzees, gorillas, or orangutans), bovine (including, for instance, cattle), caprine (including, for instance, goats), ovine (including, for instance, sheep), porcine (including, for instance, swine), equine (including, for instance, horses), members of the family Cervidae (including, for instance, deer, elk, moose, caribou, or reindeer), members of the family Bison (including, for instance, bison), feline (including, for example, domesticated cats, tigers, lions, etc.), canine (including, for example, domesticated dogs, wolves, etc.), avian (including, for example, turkeys, chickens, ducks, geese, etc.), a rodent (including, for example, mice, rats, etc.), a member of the family Leporidae (including, for example, rabbits or hares), members of the family Mustelidae (including, for example ferrets), or member of the order Chiroptera (including, for example, bats). In certain embodiments, the subject is a canine.

An anti-canine CD16A polypeptide or an anti-canine CD64 polypeptide described herein may be formulated with a pharmaceutically acceptable carrier. As used herein, "carrier" includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the active ingredient, its use in the therapeutic compositions is contemplated. Supplementary active ingredients also can be incorporated into the compositions. As used herein, "pharmaceutically acceptable" refers to a material that is not biologically or otherwise undesirable, i.e., the material may be administered to an individual along with an anti-canine CD16A polypeptide or an anti-canine CD64 polypeptide without causing any undesirable biological effects or interacting in a deleterious manner with any of the other components of the pharmaceutical composition in which it is contained.

An anti-canine CD16A polypeptide or an anti-canine CD64 polypeptide may therefore be formulated into a pharmaceutical composition. The pharmaceutical composition may be formulated in a variety of forms adapted to a preferred route of administration. Thus, a composition can be administered via known routes including, for example, oral, parenteral (e.g., intradermal, transcutaneous, subcutaneous, intramuscular, intravenous, intraperitoneal, etc.), or topical (e.g., intranasal, intrapulmonary, intramammary, intravaginal, intrauterine, intradermal, transcutaneous, rectally, etc.). A pharmaceutical composition can be administered to a mucosal surface, such as by administration to, for example, the nasal or respiratory mucosa (e.g., by spray or aerosol). A composition also can be administered via a sustained or delayed release. In one or more embodiments, the composition may be administered intravenously or subcutaneously. In one or more preferred embodiments, the composition may be administered subcutaneously.

Thus, an anti-canine CD16A polypeptide or an anti-canine CD64 polypeptide may be provided in any suitable form including but not limited to a solution, a suspension, an emulsion, a spray, an aerosol, or any form of mixture. The composition may be delivered in formulation with any pharmaceutically acceptable excipient, carrier, or vehicle. For example, the formulation may be delivered in a conventional parenteral dosage form such as, for example, a suspension or a solution. Alternatively, the formulation may be delivered in a conventional topical dosage form such as, for example, a cream, an ointment, an aerosol formulation, a non-aerosol spray, a gel, a lotion, and the like. The formulation may further include one or more additives including such as, for example, an adjuvant, a skin penetration enhancer, a colorant, a fragrance, a flavoring, a moisturizer, a thickener, and the like.

A formulation may be conveniently presented in unit dosage form and may be prepared by methods well known in the art of pharmacy. Methods of preparing a composition with a pharmaceutically acceptable carrier include the step of bringing the active agent into association with a carrier that constitutes one or more accessory ingredients. In general, a formulation may be prepared by uniformly and/or intimately bringing the active compound into association with a liquid carrier, a finely divided solid carrier, or both, and then, if necessary, shaping the product into the desired formulations.

The amount of an anti-canine CD16A polypeptide or an anti-canine CD64 polypeptide administered can vary depending on various factors including, but not limited to, the specific anti-canine CD16A polypeptide or an anti-canine CD64 polypeptide being administered, the weight, physical condition, and/or age of the subject, and/or the route of administration. Thus, the absolute weight of anti-canine CD16A polypeptide or an anti-canine CD64 polypeptide included in a given unit dosage form can vary widely, and depends upon factors such as the species, age, weight, and physical condition of the subject, and/or the method of administration. Accordingly, it is not practical to set forth generally the amount that constitutes an amount of anti-canine CD16A polypeptide or an anti-canine CD64 polypeptide effective for all possible applications. Those of ordinary skill in the art, however, can readily determine the appropriate amount with due consideration of such factors.

In one or more embodiments, the method can include administering sufficient anti-canine CD16A polypeptide or sufficient anti-canine CD64 polypeptide to provide a dose of, for example, from about 100 ng/kg to about 10 mg/kg to the subject, although in one or more embodiments the methods may be performed by administering anti-canine CD16A polypeptide or anti-canine CD64 polypeptide in a dose outside this range.

Thus, in one or more embodiments, the method can includes administering sufficient anti-canine CD16A polypeptide or sufficient anti-canine CD64 polypeptide to provide a minimum dose of at least 100 ng/kg/day such as, for example, at least 1 µg/kg/day, at least 5 µg/kg/day, at least 10 µg/kg/day, at least 25 µg/kg/day, at least 50 µg/kg/day, at least 100 µg/kg/day, at least 200 µg/kg/day, at least 300 µg/kg/day, at least 400 µg/kg/day, at least 500 µg/kg/day, at least 600 µg/kg/day, at least 700 µg/kg/day, at least 800 µg/kg/day, at least 900 µg/kg/day, or at least 1 mg/kg/day.

In one or more embodiments, the method includes administering sufficient anti-canine CD16A polypeptide or sufficient anti-canine CD64 polypeptide to provide a maximum dose of no more than 10 mg/kg/day such as, for example, no more than 5 mg/kg/day, no more than 4 mg/kg/day, no more than 3 mg/kg/day, no more than 2 mg/kg/day, no more than 1 mg/kg/day, no more than 900 µg/kg/day, no more than 800 µg/kg/day, no more than 700 µg/kg/day, no more than 600 µg/kg/day, no more than 500 µg/kg/day, no more than 400 µg/kg/day, no more than 300 µg/kg/day, no more than 200 µg/kg/day, no more than 100 µg/kg/day, no more than 90 µg/kg/day, no more than 80 µg/kg/day, no more than 70 µg/kg/day, no more than 60 µg/kg/day, no more than 50 µg/kg/day, no more than 40 µg/kg/day, no more than 30 µg/kg/day, no more than 20 µg/kg/day, or no more than 10 µg/kg/day. The anti-canine CD16A polypeptide or the anti-canine CD64 polypeptide provides a dose of "no greater than" a specified amount when the anti-canine CD16A polypeptide or the anti-canine CD64 polypeptide is not absent but is present in an amount up to and including the specified amount.

In one or more embodiments, the method includes administering sufficient anti-canine CD16A polypeptide or sufficient anti-canine CD64 polypeptide to provide a dose characterized by a range having endpoints defined by any a minimum dose identified above and any maximum dose that is greater than the selected minimum dose. For example, in one or more embodiments, the method can include administering sufficient anti-canine CD16A polypeptide or sufficient anti-canine CD64 polypeptide to provide a dose of from about 10 µg/kg/day to about 10 mg/kg/day to the subject, a dose of from about 100 µg/kg/day to about 1 mg/kg/day, a dose of from 5 µg/kg/day to 100 µg/kg/day, etc.

In certain embodiments, the method includes administering sufficient anti-canine CD16A polypeptide or sufficient anti-canine CD64 polypeptide to provide a dose that is equal to any minimum dose or any maximum dose listed above. Thus, for example, in certain embodiments, the method can include administering sufficient anti-canine CD16A polypeptide or sufficient anti-canine CD64 polypeptide to provide a dose of 1 µg/kg/day, 5 µg/kg/day, 10 µg/kg/day, 25 µg/kg/day, 50 µg/kg/day, 100 µg/kg/day, 200 µg/kg/day, 500 µg/kg/day, 1 mg/kg/day, 5 mg/kg/day, etc.

In one or more embodiments, an anti-canine CD16A polypeptide or an anti-canine CD64 polypeptide may be administered, for example, from a single dose to multiple doses per week, although in one or more embodiments the method can be performed by administering an anti-canine CD16A polypeptide or an anti-canine CD64 polypeptide at a frequency outside this range. In certain embodiments, an anti-canine CD16A polypeptide or an anti-canine CD64 polypeptide may be administered from about once per month to about five times per week. In one or more embodiments, the doses indicated above, which are described in terms of the amount of anti-canine CD16A polypeptide or anti-canine CD64 polypeptide administered over a 24-hour period, are administered in a seven-day cycle of four days of treatment and three days of rest.

In one or more embodiments, an anti-canine CD16A polypeptide or an anti-canine CD64 polypeptide may be administered, for example, from a single dose to multiple cycles of treatment, although in one or more embodiments the method can be performed by administering an anti-canine CD16A polypeptide or an anti-canine CD64 polypeptide for a duration outside this range. In one or more embodiments, the anti-canine CD16A polypeptide or an anti-canine CD64 polypeptide may be administered for three weeks. In such embodiments, each week may be a treatment cycle such as the exemplary treatment cycle described in the preceding paragraph. In other embodiments, the anti-canine CD16A polypeptide or an anti-canine CD64 polypeptide may be administered for a greater number of treatment cycles, without a gap between one set of treatment cycles and a subsequent set of treatment cycles. The gap between one set of treatment cycles and a subsequent set of treatment cycles may be a gap of one or more weeks, one or more months, or one or more years.

In embodiments in which the treatment involves administering an anti-canine CD64 polypeptide to a subject, the method may further include administering to the subject NK cells engineered to express canine CD64. As noted above, a multispecific immune cell engagers that includes an anti-canine CD64 polypeptide may be used clinically to bridge an NK cell engineered to express canine CD64 and a target cell (e.g., a cell expressing a tumor antigen or a cell expressing an infectious antigen) and induce activation of the effector cells to kill the target cell.

In one or more embodiments, the treatment methods can be employed to treat cancer in the subject. Exemplary cancers that are treatable by administering an anti-canine CD16A polypeptide or an anti-canine CD64 polypeptide to a subject include, but are not limited to, cancer comprises prostate cancer, lung cancer, colon cancer, rectum cancer, urinary bladder cancer, melanoma, kidney cancer, renal cancer, oral cavity cancer, pharynx cancer, pancreas cancer, uterine cancer, thyroid cancer, skin cancer, head and neck cancer, cervical cancer, ovarian cancer, osteosarcoma, or a hematopoietic cancer.

In one or more embodiments, the method further includes administering one or more additional therapeutic agents. The one or more additional therapeutic agents may be administered before, after, and/or coincident to the administration of an anti-canine CD16A polypeptide or an anti-canine CD64 polypeptide. An anti-canine CD16A polypeptide or an anti-canine CD64 polypeptide and the additional therapeutic agents may be co-administered. As used herein, "co-administered" refers to two or more components of a combination administered so that the therapeutic or prophylactic effects of the combination can be greater than the therapeutic or prophylactic effects of either component administered alone. Two components may be co-administered simultaneously or sequentially. Simultaneously co-administered components may be provided in one or more pharmaceutical compositions. Sequential co-administration of two or more components includes cases in which the components are administered so that each component can be present at the treatment site at the same time. Alternatively, sequential co-administration of two components can include cases in which at least one component has been cleared from a treatment site, but at least one cellular effect of administering the component (e.g., cytokine production, activation of a certain cell population, etc.) persists at the treatment site until one or more additional components are administered to the treatment site. Thus, a co-administered combination can, in certain circumstances, include components that never exist in a chemical mixture with one another. When administered sequentially, any component may be administered prior to any other component. In other embodiments, the anti-canine CD16A polypeptide or the anti-canine CD64 polypeptide and the additional therapeutic agent may be administered as part of a mixture or cocktail. In some aspects, administering an anti-canine CD16A polypeptide or an anti-canine CD64 polypeptide may allow for the effectiveness of a lower dosage of other therapeutic modalities when compared to the administration of the other therapeutic agent or agents alone, thereby decreasing the likelihood, severity, and/or extent of side effects (e.g., toxicity) observed when a higher dose of the other therapeutic agent or agents is administered.

Exemplary additional therapeutic agents can include chemotherapy agents. Suitable additional therapeutic agents include, but are not limited to, altretamine, amsacrine, L-asparaginase, colaspase, bleomycin, busulfan, capecitabine, carboplatin, carmustine, chlorambucil, cisplatin, cladribine, cyclophosphamide, cytophosphane, cytarabine, dacarbazine, dactinomycin, daunorubicin, docetaxel, doxorubicin, epirubicin, etoposide, fluorouracil, fludarabine, fotemustine, ganciclovir, gemcitabine, hydroxyurea, idarubicin, ifosfamaide, irinotecan, lomustine, melphalan, mercaptopurine, methotrexate, mitoxantrone, mitomycin C, nimustine, oxaliplatin, paclitaxel, pemetrexed, procarbazine, raltitrexed, temozolomide, teniposide, tioguanine, thiotepa, topotecan, vinblastine, vincristine, vindesine, vinorelbine, an anti-HER2 antibody therapy, an anti-HER3 antibody therapy (see, e.g., Liu et al., 2019, *Biol Proced Online* 21:5), or an anti-HER2/HER3 heterodimer complex antibody therapy (see, e.g., Liu et al., 2019, *Biol Proced Online* 21:5).

In another aspect, this disclosure describes an isolated nucleic acid sequence that encodes any embodiment of an anti-canine CD16A polypeptide or an anti-canine CD64 polypeptide. In one or more embodiments, the isolated nucleic acid encodes the anti-canine CD16A polypeptide or an anti-canine CD64 polypeptide of ay one of SEQ ID NO:5 through SEQ ID NO:20. Given the amino acid sequence of any polypeptide, a person of ordinary skill in the art can determine the full scope of polynucleotides that encode that amino acid sequence using conventional, routine methods.

As used herein, the term "nucleic acid" or "oligonucleotide" refers to polynucleotides such as deoxyribonucleic acid (DNA) or ribonucleic acid (RNA). Nucleic acids include but are not limited to genomic DNA, cDNA, mRNA, iRNA, miRNA, tRNA, ncRNA, rRNA, and recombinantly produced and chemically synthesized molecules such as aptamers, plasmids, anti-sense DNA strands, shRNA, ribozymes, nucleic acids conjugates, and oligonucleotides. A nucleic acid may be single-stranded, double-stranded, linear, or covalently circularly closed molecule. A nucleic acid can be isolated. The term "isolated nucleic acid" means that the nucleic acid (i) was amplified in vitro, for example via polymerase chain reaction (PCR), (ii) was produced recombinantly by cloning, (iii) was purified, for example, by cleavage and separation by gel electrophoresis, (iv) was synthesized, for example, by chemical synthesis, or (vi) extracted from a sample. A nucleic might be introduced—i.e., transfected-into cells. When RNA is used to transfect cells, the RNA may be modified by stabilizing modifications, capping, or polyadenylation.

As used herein "amplified DNA" or "PCR product" refers to an amplified fragment of DNA of defined size. Various techniques are available and well known in the art to detect PCR products. PCR product detection methods include, but are not restricted to, gel electrophoresis using agarose or polyacrylamide gel and adding ethidium bromide staining (a DNA intercalant), labeled probes (radioactive or non-radioactive labels, southern blotting), labeled deoxyribonucleotides (for the direct incorporation of radioactive or non-radioactive labels) or silver staining for the direct visualization of the amplified PCR products; restriction endonuclease digestion, which relies on agarose gel electrophoresis, polyacrylamide gel electrophoresis, or high-performance liquid chromatography (HPLC); dot blots, using the hybridization of the amplified DNA on specific labeled probes (radioactive or non-radioactive labels); high-pressure liquid chromatography using ultraviolet detection; electro-chemiluminescence coupled with voltage-initiated chemical reaction/photon detection; and direct sequencing using radioactive or fluorescently labeled deoxyribonucleotides for the determination of the precise order of nucleotides with a DNA fragment of interest, oligo ligation assay (OLA), PCR, qPCR, DNA sequencing, fluorescence, gel electrophoresis, magnetic beads, allele specific primer extension (ASPE) and/or direct hybridization.

Generally, nucleic acid can be extracted, isolated, amplified, or analyzed by a variety of techniques such as those described by Green and Sambrook, Molecular Cloning: A Laboratory Manual (Fourth Edition), Cold Spring Harbor Laboratory Press, Woodbury, NY 2,028 pages (2012); or as described in U.S. Pat. Nos. 7,957,913; 7,776,616; 5,234,809; and 9,012,208. Examples of nucleic acid analysis include, but are not limited to, sequencing and DNA-protein interaction. Sequencing may be by any method known in the art. DNA sequencing techniques include classic dideoxy sequencing reactions (Sanger method) using labeled terminators or primers and gel separation in slab or capillary, and next generation sequencing methods such as sequencing by synthesis using reversibly terminated labeled nucleotides, pyrosequencing, 454 sequencing, Illumina/Solexa sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Separated molecules may be sequenced by sequential or single extension reactions using polymerases or ligases as well as by single or sequential differential hybridizations with libraries of probes.

In another aspect, this disclosure describes a host cell including any of the isolated nucleic acid sequences and/or proteins described herein. Thus, this disclosure encompasses translation of a nucleic acid (e.g., an mRNA) by a host cell to produce an anti-canine CD16A polypeptide, an anti-canine CD64 polypeptide, human CD16A (SEQ ID NO:1) or a structurally similar polypeptide, canine CD16A (SEQ ID NO:2) or a structurally similar polypeptide, human CD64 (SEQ ID NO:3) or a structurally similar polypeptide, or canine CD64 (SEQ ID NO:4) or a structurally similar polypeptide.

The nucleic acid constructs described herein may be introduced into a host cell to be altered, thus allowing expression of an anti-canine CD16A polypeptide, an anti-canine CD64 polypeptide, human CD16A (SEQ ID NO:1) or a structurally similar polypeptide, canine CD16A (SEQ ID NO:2) or a structurally similar polypeptide, human CD64 (SEQ ID NO:3) or a structurally similar polypeptide, or canine CD64 (SEQ ID NO:4) or a structurally similar polypeptide within the cell, thereby generating a genetically engineered cell. A variety of methods are known in the art and suitable for introduction of nucleic acid into a cell, including viral and non-viral mediated techniques. Examples of typical non-viral mediated techniques include, but are not limited to, electroporation, calcium phosphate mediated transfer, nucleofection, sonoporation, heat shock, magnetofection, liposome mediated transfer, microinjection, microprojectile mediated transfer (nanoparticles), cationic polymer mediated transfer (DEAE-dextran, polyethylenimine, polyethylene glycol (PEG) and the like) or cell fusion. Other methods of transfection include proprietary transfection reagents such as LIPOFECTAMINE (Thermo Fisher Scientific, Inc., Waltham, MA), HILYMAX (Dojindo Molecular Technologies, Inc., Rockville, MD), FUGENE (Promega Corp., Madison, WI), JETPEI (Polyplus Transfection, Illkirch, France), EFFECTENE (Qiagen, Hilden, Germany) and DreamFect (OZ Biosciences, Inc USA, San Diego, CA).

The nucleic acid constructs described herein may be introduced into a host cell to be altered, thus allowing expression within the cell of the protein encoded by the nucleic acid. A variety of host cells are known in the art and suitable for protein expression. Examples of typical cell used for transfection and protein expression include, but are not limited to, a bacterial cell, a eukaryotic cell (e.g., an immune cell such as an NK cell), a yeast cell, an insect cell, or a plant cell such as, for example, *E. coli*, *Bacillus*, *Streptomyces*, *Pichia pastoris*, *Salmonella typhimurium*, *Drosophila* S2, *Spodoptera* SJ9, CHO, COS (e.g., COS-7), 3T3-F442A, HeLa, HUVEC, HUAEC, NIH 3T3, Jurkat, 293, 293H, or 293F.

In one or more embodiments, the anti-canine CD16 polypeptide and/or anti-canine CD64 polypeptide can be used in the context of a diagnostic assay or device. In one or more of these embodiments, the anti-canine CD16 polypeptide can include a detectable label that allows detection of the compound after the compound is administered to a subject or is contacted with a sample that contains CD16 to which the anti-canine CD16 polypeptide binds. The detectable label can be any suitable detectable label. Exemplary detectable labels include, but are not limited to, a radioactive label, a fluorescent label, an enzymatic label, a colorimetric label, a magnetic label, and the like.

In one or more embodiments, the anti-canine CD16 polypeptide may be immobilized to a substrate to, for example, capture CD16 in a sample. Captured CD16 may be detected using any suitable method for detecting captured ligands. Alternatively, captured CD16 may be released from the anti-canine CD16 polypeptide and collected using any suitable method for release and collection of captured ligands.

In one or more embodiments, the anti-canine CD64 polypeptide can include a detectable label that allows detection of the compound after the compound is administered to a subject or is contacted with a sample that contains CD64 to which the anti-canine CD64 polypeptide binds. The detectable label can be any suitable detectable label. Exemplary detectable labels include, but are not limited to, a radioactive label, a fluorescent label, an enzymatic label, a colorimetric label, a magnetic label, and the like.

In one or more embodiments, the anti-canine CD64 polypeptide may be immobilized to a substrate to, for example, capture CD64 in a sample. Captured CD64 may be detected using any suitable method for detecting captured ligands. Alternatively, captured CD64 may be released from the anti-canine CD64 polypeptide and collected using any suitable method for release and collection of captured ligands.

EXEMPLARY EMBODIMENTS

Embodiment 1. An anti-canine CD16 polypeptide comprising one or more of:
SEQ ID NO:6 or a functional variant thereof;
SEQ ID NO:7 or a functional variant thereof;
SEQ ID NO:8 or a functional variant thereof;
SEQ ID NO: 10 or a functional variant thereof;
SEQ ID NO: 11 (DTS) or a functional variant thereof; or
SEQ ID NO: 12, or a functional variant thereof.

Embodiment 2. An anti-canine CD16 polypeptide comprising:
a CDR region of SEQ ID NO:5 or a functional variant thereof, or
a CDR region of SEQ ID NO:9 or a functional variant thereof.

Embodiment 3. An anti-canine CD64 polypeptide comprising one or more of:
SEQ ID NO:14 or a functional variant thereof;
SEQ ID NO:15 or a functional variant thereof;
SEQ ID NO:16 or a functional variant thereof;
SEQ ID NO:18 or a functional variant thereof;
SEQ ID NO:19 or a functional variant thereof; or
SEQ ID NO:20, or a functional variant thereof.

Embodiment 4. An anti-canine CD64 polypeptide comprising:
a CDR region of SEQ ID NO:13 or a functional variant thereof, or
a CDR region of SEQ ID NO:17 or a functional variant thereof.

Embodiment 5. A multispecific compound comprising:
a targeting domain that selectively binds to:
  a target cell; or
  a target antigen expressed by a target cell; and
an immune cell engaging domain operably linked to the targeting domain, the immune cell engaging domain comprising an anti-canine CD16 polypeptide, the anti-canine CD16 polypeptide comprising:
SEQ ID NO:6 or a functional variant thereof;
SEQ ID NO:7 or a functional variant thereof;
SEQ ID NO:8 or a functional variant thereof;
SEQ ID NO: 10 or a functional variant thereof;
SEQ ID NO: 11 (DTS) or a functional variant thereof;
SEQ ID NO: 12, or a functional variant thereof;
a CDR region of SEQ ID NO:5 or a functional variant thereof; or
a CDR region of SEQ ID NO:9 or a functional variant thereof.

Embodiment 6. The multispecific compound of Embodiment 5, wherein the immune cell engaging domain engages a natural killer (NK) cell.

Embodiment 7. The multispecific compound of Embodiment 5 or Embodiment 6, wherein the immune cell engaging domain comprises an scFv, a F(ab)$_2$, a Fab, or a single domain antibody (sdAb).

Embodiment 8. The multispecific compound of any one of Embodiments 5-7, wherein the immune cell engaging domain comprises:
SEQ ID NO:6, SEQ ID NO:7, and SEQ ID NO:8; or
SEQ ID NO:10, SEQ ID NO:11 (DTS), and SEQ ID NO:12.

Embodiment 9. The multispecific compound of any one of Embodiments 5-8, wherein the targeting domain and the immune cell engaging domain are linked by a linking segment comprising any one of SEQ ID NOs:33-44.

Embodiment 10. The multispecific compound of any one of Embodiments 5-9, further comprising an immune cell activating domain.

Embodiment 11. The multispecific compound of Embodiment 10, wherein:
the immune cell comprises an NK cell; and
the immune cell activating domain comprises a cytokine or a functional portion thereof.

Embodiment 12. The multispecific compound of Embodiment 11, wherein the cytokine is IL-12 or a functional variant thereof.

Embodiment 13. The multispecific compound of Embodiment 11, wherein the cytokine is IL-15 or a functional variant thereof.

Embodiment 14. The multispecific compound of Embodiment 13, wherein the functional variant of IL-15 includes an N72D or N72A amino acid substitution compared to SEQ ID NO:47.

Embodiment 15. The multispecific compound of any one of Embodiments Embodiment 10-14, wherein the immune cell activating domain is linked to either the targeting domain or the immune cell engaging domain by a linking segment comprising any one of SEQ ID NOs:33-44.

Embodiment 16. The multispecific compound of any one of Embodiments Embodiment 5-15, wherein the targeting domain specifically binds to a tumor antigen.

Embodiment 17. The multispecific compound of any one of Embodiments Embodiment 5-15, wherein the targeting domain specifically binds to an infectious antigen.

Embodiment 18. The multispecific compound of any one of Embodiments Embodiment 5-15, wherein the targeting domain an scFv, a F(ab)$_2$, a Fab, or a single domain antibody (sdAb).

Embodiment 19. A pharmaceutical composition comprising:
the multispecific compound of any one of Embodiments 5-18; and
a pharmaceutically acceptable carrier.

Embodiment 20. A multispecific compound comprising:
a targeting domain that selectively binds to:
  a target cell; or
  a target antigen expressed by a target cell; and
an immune cell engaging domain operably linked to the targeting domain, the immune cell engaging domain comprising an anti-canine CD64 polypeptide, the anti-canine CD64 polypeptide comprising:
SEQ ID NO:14 or a functional variant thereof;
SEQ ID NO:15 or a functional variant thereof;
SEQ ID NO:16 or a functional variant thereof;
SEQ ID NO:18 or a functional variant thereof;
SEQ ID NO:19 or a functional variant thereof;
SEQ ID NO:20, or a functional variant thereof, a CDR region of SEQ ID NO:13 or a functional variant thereof, or a CDR region of SEQ ID NO:17 or a functional variant thereof.

Embodiment 21. The multispecific compound of Embodiment 20, wherein the immune cell engaging domain engages a natural killer (NK) cell engineered to express canine CD64.

Embodiment 22. The multispecific compound of Embodiment 20 or Embodiment 21, wherein the immune cell engaging domain comprises an scFv, a F(ab)$_2$, a Fab, or a single domain antibody (sdAb).

Embodiment 23. The multispecific compound of any one of Embodiments 20-22, wherein the immune cell engaging domain comprises:

SEQ ID NO:14, SEQ ID NO:15, and SEQ ID NO:16; or
SEQ ID NO:18, SEQ ID NO:19, and SEQ ID NO:20.

Embodiment 24. The multispecific compound of any one of Embodiments 20-23, wherein the targeting domain and the immune cell engaging domain are linked by a linking segment comprising any one of SEQ ID NOs:33-44.

Embodiment 25. The multispecific compound of any one of Embodiments 20-24, further comprising an immune cell activating domain.

Embodiment 26. The multispecific compound of Embodiment 25, wherein:

the immune cell comprises an NK cell; and
the immune cell activating domain comprises a cytokine or a functional portion thereof.

Embodiment 27. The multispecific compound of Embodiment 26, wherein the cytokine is IL-12 or a functional variant thereof.

Embodiment 28. The multispecific compound of Embodiment 26, wherein the cytokine is IL-15 or a functional variant thereof.

Embodiment 29. The multispecific compound of Embodiment 28, wherein the functional variant of IL-15 includes an N72D or N72A amino acid substitution compared to SEQ ID NO:47.

Embodiment 30. The multispecific compound of any one of Embodiments Embodiment 25-29, wherein the immune cell activating domain is linked to either the targeting domain or the immune cell engaging domain by a linking segment comprising any one of SEQ ID NOs:33-44.

Embodiment 31. The multispecific compound of any one of Embodiments Embodiment 20-30, wherein the targeting domain specifically binds to a tumor antigen.

Embodiment 32. The multispecific compound of any one of Embodiments Embodiment 20-30, wherein the targeting domain specifically binds to an infectious antigen.

Embodiment 33. The multispecific compound of any one of Embodiments Embodiment 20-32, wherein the targeting domain comprises an scFv, a F(ab)$_2$, a Fab, or a single domain antibody (sdAb).

Embodiment 34. A pharmaceutical composition comprising:

the multispecific compound of any one of Embodiments 19-31; and
a pharmaceutically acceptable carrier.

Embodiment 35. An isolated nucleic acid sequence encoding the multispecific compound of any one of Embodiments 5-18.

Embodiment 36. A host cell comprising the isolated nucleic acid of Embodiment 35.

Embodiment 37. An isolated nucleic acid sequence encoding the multispecific compound of any one of Embodiments 20-33.

Embodiment 38. A host cell comprising the isolated nucleic acid of Embodiment 37.

Embodiment 39. A human NK cell engineered to express canine CD16.

Embodiment 40. A human NK cell engineered to express canine CD64.

Embodiment 41. A canine NK cell engineered to express canine CD64.

Embodiment 42. A method comprising:

administering to a subject the multispecific compound of any one of Embodiments 5-18 in an amount effective to induce natural killer (NK)-mediated killing of a cell.

Embodiment 43. A method comprising:

administering to the subject NK cells engineered to express canine CD64; and
administering to a subject the multispecific compound of any one of Embodiments 20-23 in an amount effective to induce natural killer (NK)-mediated killing of a cell.

Embodiment 44. A method of treating a subject having, or at risk of having, cancer in which tumor cells express a tumor antigen, the method comprising:

administering to the subject the multispecific compound of any one of Embodiments 5-18 in an amount effective to:
ameliorate at least one symptom or clinical sign of the cancer; or
reduce risk of the subject developing cancer compared a comparable untreated individual; wherein the multispecific compound comprises a targeting domain that specifically binds to the tumor antigen.

Embodiment 45. The method of Embodiment 44, wherein the cancer comprises prostate cancer, lung cancer, colon cancer, rectum cancer, urinary bladder cancer, melanoma, kidney cancer, renal cancer, oral cavity cancer, pharynx cancer, pancreas cancer, uterine cancer, thyroid cancer, skin cancer, head and neck cancer, cervical cancer, ovarian cancer, osteosarcoma, or a hematopoietic cancer.

Embodiment 46. The method of Embodiment 44 or Embodiment 45, wherein the multispecific compound is administered prior to, simultaneously with, or following chemotherapy, surgical resection of a tumor, or radiation therapy.

Embodiment 47. The method of Embodiment 46, wherein the chemotherapy comprises altretamine, amsacrine, L-asparaginase, colaspase, bleomycin, busulfan, capecitabine, carboplatin, carmustine, chlorambucil, cisplatin, cladribine, cyclophosphamide, cytophosphane, cytarabine, dacarbazine, dactinomycin, daunorubicin, docetaxel, doxorubicin, epirubicin, etoposide, fluorouracil, fludarabine, fotemustine, ganciclovir, gemcitabine, hydroxyurea, idarubicin, ifosfamide, irinotecan, lomustine, melphalan, mercaptopurine, methotrexate, mitoxantrone, mitomycin C, nimustine, oxaliplatin, paclitaxel, pemetrexed, procarbazine, raltitrexed, temozolomide, teniposide, tioguanine, thiotepa, topotecan, vinblastine, vincristine, vindesine, or vinorelbine.

Embodiment 48. A method of treating a subject having, or at risk of having, cancer in which tumor cells express a tumor antigen, the method comprising:

administering to the subject NK cells engineered to express canine CD64 or a fragment thereof recognized by the multispecific compound of any one of Embodiments 20-33; and
administering to the subject the multispecific compound of any one of Embodiments 20-33 in an amount effective to:
ameliorate at least one symptom or clinical sign of the cancer; or reduce risk of the subject developing cancer compared a comparable untreated individual; wherein the multispecific compound comprises a targeting domain that specifically binds to the tumor antigen.

Embodiment 49. The method of Embodiment 48, wherein the cancer comprises prostate cancer, lung cancer, colon cancer, rectum cancer, urinary bladder cancer, melanoma, kidney cancer, renal cancer, oral cavity cancer, pharynx cancer, pancreas cancer, uterine cancer, thyroid cancer, skin cancer, head and neck cancer, cervical cancer, ovarian cancer, osteosarcoma, or a hematopoietic cancer.

Embodiment 50. The method of Embodiment 48 or Embodiment 49, wherein the multispecific compound is administered prior to, simultaneously with, or following chemotherapy, surgical resection of a tumor, or radiation therapy.

Embodiment 51. The method of Embodiment 50, wherein the chemotherapy comprises altretamine, amsacrine, L-asparaginase, colaspase, bleomycin, busulfan, capecitabine, carboplatin, carmustine, chlorambucil, cisplatin, cladribine, cyclophosphamide, cytophosphane, cytarabine, dacarbazine, dactinomycin, daunorubicin, docetaxel, doxorubicin, epirubicin, etoposide, fluorouracil, fludarabine, fotemustine, ganciclovir, gemcitabine, hydroxyurea, idarubicin, ifosfamaide, irinotecan, lomustine, melphalan, mercaptopurine, methotrexate, mitoxantrone, mitomycin C, nimustine, oxaliplatin, paclitaxel, pemetrexed, procarbazine, raltitrexed, temozolomide, teniposide, tioguanine, thiotepa, topotecan, vinblastine, vincristine, vindesine, or vinorelbine.

Embodiment 52. A method of treating a subject having, or at risk of having, an infectious condition in which infected cells express an infectious antigen, the method comprising:
  administering to the subject the multispecific compound of any one of Embodiments 5-18 in an amount effective to:
  ameliorate at least one symptom or clinical sign of the infectious condition; or
  reduce risk of the subject developing the infectious compared a comparable untreated individual;
  wherein the multispecific compound comprises a targeting domain that specifically binds to the infectious antigen.

Embodiment 53. A method of treating a subject having, or at risk of having, an infectious condition in which infected cells express an infectious antigen, the method comprising:
  administering to the subject the multispecific compound of any one of Embodiments 20-33 in an amount effective to:
  ameliorate at least one symptom or clinical sign of the infectious condition; or
  reduce risk of the subject developing the infectious compared a comparable untreated individual;
  wherein the multispecific compound comprises a targeting domain that specifically binds to the infectious antigen.

Embodiment 54. A targeted imaging compound comprising:
  a targeting domain comprising the anti-canine CD16 polypeptide of Embodiment 1 or Embodiment 2; and
  an imaging domain linked to the targeting domain.

Embodiment 55. The targeted imaging compound of Embodiment 54, wherein the imaging domain comprises a colorimetric label, a fluorescent label, a radioactive label, a magnetic label, or an enzymatic label.

Embodiment 56. A targeted imaging compound comprising:
  a targeting domain comprising the anti-canine CD64 polypeptide of Embodiment 3 or Embodiment 4; and
  an imaging domain linked to the targeting domain.

Embodiment 57. The targeted imaging compound of Embodiment 56, wherein the imaging domain comprises a colorimetric label, a fluorescent label, a radioactive label, a magnetic label, or an enzymatic label.

Embodiment 58. A capture assay device comprising the anti-canine CD16 polypeptide of Embodiment 1 or Embodiment 2 immobilized to a substrate.

Embodiment 59. A capture assay device comprising the anti-canine CD64 polypeptide of Embodiment 3 or Embodiment 4 immobilized to a substrate.

Embodiment 60. The anti-canine CD16 polypeptide of Embodiment 1 or Embodiment 2, the multispecific compound of any one of Embodiments 5-18, the pharmaceutical composition of Embodiment 19, the nucleic acid of Embodiment 37, the host cell of Embodiment 39, the engineered human NK cell of Embodiment 39, the method of any one of Embodiments 42, 44-47, or 52, the targeted imaging compound of Embodiment 54 or Embodiment 55, or the capture assay device of Embodiment 59, wherein the canine CD16 is canine CD16A.

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Reference throughout this specification to "one embodiment," "an embodiment," "certain embodiments," or "one or more embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments. Furthermore, the particular features, configurations, compositions, or characteristics may be combined in any suitable manner in one or more embodiments. Thus, features described in the context of one embodiment may be combined with features described in the context of a different embodiment except where the features are necessarily mutually exclusive.

For any method disclosed herein that includes discrete steps, the steps may be conducted in any feasible order. And, as appropriate, any combination of two or more steps may be conducted simultaneously.

As used herein, the terms "preferred" and "preferably" refer to embodiments of the invention that may afford certain benefits under certain circumstances. However, other embodiments may also be preferred under the same or other circumstances. Furthermore, the recitation of one or more preferred embodiments does not imply that other embodiments are not useful and is not intended to exclude other embodiments from the scope of the invention.

EXAMPLES

The present invention is illustrated by the following examples. It is to be understood that the particular examples, materials, amounts, and procedures are to be interpreted broadly in accordance with the scope and spirit of the invention as set forth herein.

Example 1

Cells

Peripheral blood was collected from healthy pet dogs with consent from owners. The dogs consisted of various breeds and mixed breeds. All animals had received routine veterinary care, vaccinations, parasite control, and were considered to be in overall good health. Blood collection was carried out in strict accordance with the recommendations in the Guide for the Care and Use of Laboratory Animals of the National Institutes of Health. The protocol was approved by the Institutional Animal Care and Use Committee of the University of Minnesota (Protocol Numbers: 1304-30546A and 1903-36913A). Blood was collected in K2-EDTA blood collection tubes (BD Biosciences, Franklin Lakes, NJ). Total leukocytes and PBMCs were isolated as we have previously described (Snyder et al., *Vet Immunol Immunopathol* 231: 110162, 2021). Leukocytes with ≥95% viability, as assessed by trypan blue staining, were used in the described assays. For cell activation, leukocytes were stimulated with phorbol-12-myristate-13-acetate (PMA) (MilliporeSigma, Burlington, MA), as previously described (Snyder et al., *Vet Immunol Immunopathol* 231:110162, 2021). Some cells were pre-incubated for 30 minutes on ice with the function-blocking ant-ADAM17 mAb MEDI3622 (5 µg/ml) prior to activation. The NK-92MI cells, which are IL-2 independent cells and derived from NK-92 cells, SKOV-3 cells, and 293T were obtained from ATCC (Manassas, VA). FreeStyle 293-F cells were obtained from Thermo Fisher Scientific, Inc. (Waltham, MA). All cells were cultured per the manufacturer's directions, as we have previously described (Snyder et al., *Front Immunol* 9:2873, 2018; Hintz et al., *Cancer Immunol Res* 9(11):1270-1282, 2021).

Antibodies

To produce mAbs to canine CD16A and CD64, BALB/c mice were immunized intraperitoneally with purified soluble protein of each FcγR and hybridomas generated based on previous methods (Jones et al., *J Immunol* 156(10):3772-3779, 1996; Walcheck et al., *Blood* 99(11):4063-4069, 2002). The anti-ADAM17 mAb MEDI3622 has been previously described (Mishra et al., *Cancer Immunol Immunother* 67(9):1407-1416, 2018; Snyder et al., *Vet Immunol Immunopathol* 231:110162, 2021; Mishra et al., *Int J Mol Sci* 21:6688, 2020). Isotype-matched negative control mAbs were purchased from BioLegend (San Diego, CA) and BD Biosciences (Franklin Lakes, NJ). Affinity purified canine serum IgG was purchased from SouthernBiotech (Birmingham, AL). Fluorophore-conjugated F(ab')$_2$ goat anti-mouse secondary antibodies and fluorophore-conjugated streptavidin were purchased from Jackson ImmunoResearch Laboratories, Inc. (West Grove, PA) and ZOMBIE VIOLET Fixable Viability Kit was purchased from BioLegend (San Diego, CA). All commercially available mAbs are listed in Table 1.

TABLE 1

Antibodies.

| Antigen | Clone | Species | Company |
| --- | --- | --- | --- |
| Influenza Hemaglutinin (HA)-Tag | 12CA5 | Mouse | Santa Cruz Biotechnology, Inc., Dallas, TX. |
| canine CD4 | YKIX302.9 | Rat | Bio-Rad Laboratories, Inc., Hercules, California |
| canine CD3 | CA17.2A12 | Mouse | Bio-Rad Laboratories, Inc., Hercules, California |
| canine CD5 | YKIX322.3 | Rat | Bio-Rad Laboratories, Inc., Hercules, California |
| human CD14 | TUK4 | Mouse | Bio-Rad Laboratories, Inc., Hercules, California |
| canine CD20 | 6C12 | caninized | Invivogen, San Diego, CA |
| canine CD20 | 6C12 | Mouse | Invivogen, San Diego, CA |
| canine NKp46 | 48A | Mouse | MilliporeSigma, Burlington, MA |
| human CD94 | HP-3D9 (RUO) | Mouse | BD Biosciences, Franklin Lakes, NJ |

Flow Cytometry

For cell staining, nonspecific antibody binding sites were blocked for 30 min using 25% canine serum and 25% FBS in PBS buffer (without $Ca^{+2}$ and $Mg^{+2}$) (Lonza Group AG, Basel, Switzerland) prior to their staining with antibodies. All cell staining was analyzed on a FACSCelesta instruments (BD Biosciences, Franklin Lakes, NJ), as previously described (Snyder et al., *Vet Immunol Immunopathol* 231: 110162, 2021). Briefly, for controls, fluorescence minus one was used as well as appropriate isotype-matched antibodies. An FSC-A/SSC-A plot was used to set an electronic gate on leukocyte populations and an FSC-A/FSC-H plot was used to set an electronic gate on single cells. Fixable viability dyes eFluor 506 (Thermo Fisher Scientific, Inc., Waltham, MA) or ZOMBIE VIOLET (BioLegend, San Diego, CA) were used to assess live vs. dead cells, as per the manufacturers' instructions. Canine leukocyte subsets were identified based on their forward and side light-scattering characteristics and various phenotypic markers, as described.

Canine IgG adsorption to NK-92 cells was performed as previously described (17, 18), with some modifications. Briefly, cells were incubated with the indicated concentrations of canine IgG previously biotinylated using an EZ-LINK Sulfo-NHS-LC-Biotin Kit (Thermo Fisher Scientific, Inc., Waltham, MA) per the manufacturer's instructions, for two hours at 37° C. in MEM-α basal media supplemented with HEPES (10 mM), and 2-mercaptoethanol (0.1 mM). Binding levels of biotinylated canine IgG was determined by staining the cells with allophycocyanin-streptavidin (Jackson ImmunoResearch, Inc., West Grove, PA).

Western Blotting

Protein concentrations were quantified using a bicinchoninic acid assay (BCA) (Pierce Biotechnology, Waltham, MA). Five micrograms rof protein [1× Laemmli sample buffer (Bio-Rad Laboratories, Inc., Hercules, CA), 0.1M DTT] was resolved by SDS-PAGE and transferred to a nitrocellulose membrane. Blots were blocked in Intercept TBS blocking buffer (LI-COR Biosciences, Inc., Lincoln, NE) for one hour at room temperature and incubated with primary antibodies and Quick Western IRDye 680RD detection reagent (LI-COR Biosciences, Inc., Lincoln, NE) overnight at 4° C. Blots were visualized using an ODYSSEY imager (LI-COR Biosciences, Inc., Lincoln, NE). Primary antibodies used were anti-canine CD64 clone 10 and anti-canine-CD16A clone 4A5 at 5 µg/ml each.

Cytotoxicity Assays

Antibody-dependent cellular toxicity (ADCC) assays were conducted using a DELFIA EuTDA cytotoxicity according to the manufacturer's instructions (PerkinElmer, Inc., Waltham, MA) and as we have previously described (Snyder et al., *Front Immunol*, 2018, 9:2873; Hintz et al., *Cancer Immunol Res* 9(11):1270-1282, 2021). Briefly, SKOV-3-canine CD20 target cells were labeled with Bis (acetoxymethyl)-2-2:6,2 terpyridine 6,6 dicarboxylate (BATDA) for 30 minutes in their culture medium, washed in culture medium, and pipetted into a 96-well non-tissue culture-treated U-bottom plates at a density of 8×10 cells/well. Caninized anti-canine CD20 mAb was either adsorbed to NK-92 cells at 5 µg/ml in MEM-α basal media supplemented with HEPES (10 mM), and 2-mercaptoethanol (0.1 mM) then washed with MEM-α basal media or the mAb was added directly to the SKOV-3 cells at 5 µg/ml and NK-92 cells were added at the indicated E:T ratios. The plates were centrifuged at 400×g for one minute and then incubated for two hours in a humidified 5% $CO_2$ atmosphere at 37° C. At the end of the incubation, the plates were centrifuged at 500×g for five minutes and supernatants were transferred to a 96-well DELFIA Yellow Plate (PerkinElmer, Inc., Waltham, MA) and combined with europium. Fluorescence was measured by time-resolved fluorometry using a plate reader (CLARIOSTAR, BMG Labtech, Inc., Ortenberg, Germany). BATDA-labeled target cells alone with or without therapeutic antibodies were cultured in parallel to assess spontaneous lysis and in the presence of 1% Triton-X to measure maximum lysis. ADCC for each sample is represented as % specific release and was calculated using the following formula:

Percent Specific Release =

$$\frac{(\text{Experimental release} - \text{Spontaneous release})}{(\text{Maximal release} - \text{Spontaneous release})} \times 100.$$

For each experiment, assays were conducted in triplicate that were measured using two or three replicate assay wells.
Cloning of Canine CD16A, CD64, and CD20, Generation of Expression Constructs, and Cell Line Transduction Total RNA was isolated from canine peripheral blood leukocytes using TRIzol total RNA isolation reagent (Thermo Fisher Scientific, Inc., Waltham, MA). Peripheral blood cDNA was synthesized with the SuperScript First-Strand Synthesis (Thermo Fisher Scientific, Inc., Waltham, MA) and used in RT-PCR for expression construct generation. Full-length canine CD16A cDNA corresponding to two extracellular domains, transmembrane segment, and cytoplasmic region was amplified using the forward primer 5'-CTC TAG ACT GCC GGA TCC GCA GTG ACT GCC TGA CCC TAA TGT G-3' (SEQ ID NO:48) and the reverse primer 5'-TCG AAT TTA AAT GGA TCC AGA GAG GTC CAG AGG GGT TGC TTT-3' (SEQ ID NO:49). The underlined nucleotides indicate Bam HI restriction sites. To generate N-terminus hemagglutinin A (HA)-tagged canine CD16A, we amplified a cDNA fragment using the forward primer 5'-GCC CAG CCG GCC AGA TCT ACA CAA GCT GCA GAT GTC CCA-3' (SEQ ID NO:50) and the reverse primer 5'-GCG GAT CCC GGG AGA TCT AGA GAG GTC CAG AGG GGT TGC TTT-3' (SEQ ID NO:51). The underlined nucleotides indicate Bgl II restriction sites. An IN-FUSION HD cloning kit (Takara Bio USA, San Jose, CA) was used to clone the canine CD16A cDNA fragment into a pDisplay vector (Thermo Fisher Scientific, Inc., Waltham, MA) linearized with BglII (New England Biolabs, Inc., Ipswich, MA). The expression cassette consisting of Igx signal peptide, N-terminal HA tag, and canine CD16A was amplified using the forward primer 5'-TCT AGA CTG CCG GAT CCA CTA GTA ACG GCC GCC AGT GT-3' (SEQ ID NO:52) and the reverse primer 5'-TCG AAT TTA AAT GGA TCC AGA GAG GTC CAG AGG GGT TGC TTT-3' (SEQ ID NO:53). The underlined nucleotides indicate Bam HI restriction sites. Canine CD16A or HA-tagged CD16A were then cloned into the retrovirus expression vector pBMN-I-GFP (Addgene, Watertown, MA) linearized by Bam HI (New England Biolabs, Inc., Ipswich, MA) using the IN-FUSION HD cloning kit (Takara Bio USA, San Jose, CA).

Full-length canine CD64 cDNA corresponding to three extracellular domains, transmembrane segment, and cytoplasmic region was amplified using the forward primer 5'-TCT AGA CTG CCG GAT CCG GAG ATA ACA TGT GGC TCT TGA CAG TTC TA-3' (SEQ ID NO:54) and the reverse primer 5'-TCG AAT TTA AAT GGA TCC AAA AAG AAG TGG GAG GCA CCA TC-3' (SEQ ID NO:55). The underlined nucleotides indicate Bam HI restriction sites. HA-tagged canine CD64 was amplified using the forward primer 5'-GCC CAG CCG GCC AGA TCT CAA ACA GAC CCC GTA AAG GCA-3' SEQ ID NO:21) and the reverse primer 5'-GCG GAT CCC GGG AGA TCT AAA AAG AAG TGG GAG GCA CCA TC-3' (SEQ ID NO:22). The underlined nucleotides indicate Bgl II restriction sites. Their cloning into pDisplay and/or pBMN-I-GFP were carried out as described above.

Full-length canine CD20 cDNA was amplified using the forward primer 5'-TCT AGA CTG CCG GAT CCA GAG GGT GAG ATG ACA ACA CCC AGA-3' (SEQ ID NO:23) and the reverse primer 5'-TCG AAT TTA AAT GGA TCC TTA AGG GAT GCT GTC GTT TTC TAT-3' (SEQ ID NO:24). The underlined nucleotides indicate Bam HI restriction sites. The cloning of canine CD20 into pBMN-I-GFP was carried out as described above. The expression of all constructs in pBMN-I-GFP were confirmed using the sequencing primers 5'-TAG CTG GAA GAA CAC GCC CGT A-3' (SEQ ID NO:25) and 5'-GCA GAA GTA GGA GCC ATT GTG T-3' (SEQ ID NO:26). Pseudo retrovirus particles were generated as previously described (Jing et al., *PLoS One* 10(3): e0121788, 2015), and were subsequently used for NK-92 or SKOV-3 cell transduction. Cells were sorted through FACSAria II cell sorting on GFP expression (BD Biosciences, Franklin Lakes, NJ).
Cloning of Soluble Canine CD16A and CD64, Generation of Expression Constructs, and Cell Line Transduction Canine CD16A cDNA corresponding to amino acids 1-205 with a 6×histidine-tag at the carboxyl terminus was amplified using the forward primer 5'-GAA GAC ACC GAC TCT AGA GCA GTG ACT GCC TGA CCC TAA TGT GA-3' (SEQ ID NO:27), in which the underlined nucleotides indicate an Xba I restriction site, and the reverse primer 5'-GTA GTC AGC CCG GGA TCC TTA ATG ATG ATG ATG ATG ATG GGG CCA GTG TGA AAG GAG TA-3' (SEQ ID NO:28), in which the underlined nucleotides indicate a Bam HI restriction site).

Canine CD64 cDNA corresponding to amino acids 1-280 with a 6×histidine-tag at the carboxyl terminus was amplified using the forward primer 5'-GAC TCT AGA GGA GAT AAC ATG TGG CTC TTG ACA GTT CTA-3' (SEQ ID NO:29), in which the underlined nucleotides indicate an Xba I restriction sites, and the reverse primer 5'-CCG GGA TCC TTA ATG ATG ATG ATG ATG ATG CAC TTG AAG CTC CAA CTC AGG G-3' (SEQ ID NO:30), in which the underlined nucleotides indicate a Bam HI restriction site.

Amplified cDNA was digested by Xba I and Bam HI then and cloned into a pLenti-CMV vector (Vigene Biosciences, Inc., Rockville, MD; Ye at al., *Elife* 10:e64815, 2021) digested with the same restriction enzymes. The expression of all constructs in pLenti-CMV were confirmed using the sequencing primers 5'-CAT GGG AAA GCA TCG CTA CGA A-3' (SEQ ID NO:31) and 5'-TCA GAT TGA CCA CAT GCC CCT C-3' (SEQ ID NO:32). Pseudo-lentiviral particles containing soluble canine CD16A or CD64 were generated using 293T cells and packaging vectors pMD2.G and pCMV-dR8.74psPAX2 (Addgene, Watertown, MA).

Pseudo-lentiviral particles were transduced into the FreeStyle 293-F cells. The 293-F cell line was established under puromycin selection. The 293-F cells stably expressing soluble canine CD16A or CD64 were cultured in the FREESTYLE 293 Expression Medium (Thermo Fisher Scientific, Inc., Waltham, MA) and cell culture supernatants were harvested when cell density reached $2.5\times10^6$/ml. Soluble canine CD16A or CD64 were purified from cell culture supernatants using a two-step purification procedure. First step, Ni-affinity chromatography. His-tagged proteins in cell culture supernatants were purified on a HisTrap HP His tag protein purification column (Cytiva, Marlborough, MA) according to the manufacture's protocol. Second step, Fast protein liquid chromatography. Soluble canine CD16A and CD64 from the first step purification were injected into a Superdex 200 Increase 10/300 GL column (MilliporeSigma, Burlington, MA) on an AKTA pure protein purification system (Cytiva, Marlborough, MA). The purity of proteins was >95% as determined by SDS-PAGE.

Statistical Analyses

Comparison between two groups was done using Student t test. Comparison between three or more groups was done using one-way ANOVA followed by Tukey honest significance post hoc test. Results are depicted as mean±SD. The symbols used to represent the p values were as follows; , $P\leq0.01$; *, $P\leq0.001$; ****, $P\leq0.0001$.

Example 2

A trispecific Killer engager compound (TriKE) was constructed using conventional DNA ligation techniques. The TriKE compound was designed to include, from the amino terminal to the carboxy terminal, an anti-canine CD16 NK engaging domain, a canine IL-15 NK activating domain, and an anti-B7H3 targeting domain (SEQ ID NO:56). The 20-amino-acid linking segment PSGQAGAAASESLFVSNHAY (SEQ ID NO:35) was used to link the anti-CD16 NK engaging domain with the canine IL-15 NK activating domain. The seven-amino-acid linking segment EASGGPE (SEQ ID NO:36) was used to link the NK activating domain and the anti-B7H3 targeting domain. The resulting hybrid 1615B7H3 gene expressed using a pET28c expression vector under the control of an isopropyl-D-thiogalactopyranoside (IPTG) inducible T7 promoter. *Escherichia coli* strain BL21 (DE3) (Novagen, Madison, WI) was used for protein expression after plasmid transfection. Bacteria were cultured over-night in Luria broth containing 50 μg/mL kanamycin for selection. Expression was induced by adding IPTG. Bacterial expression resulted in packaging of the TriKE protein into inclusion bodies, so bacteria were sonicated and centrifuged. The hybrid protein was extracted, refolded, and purified. The final protein was stored in PBS and frozen in −80° C.

Several assays were performed to confirm the activity of each of the three functional domains of the molecule. Binding of the anti-CD16 and anti-B7-H3 antibody fragments were first confirmed by flow cytometry. Functionality of IL-15 was confirmed by measuring lymphocyte expansion/proliferation with trypan blue vital dye. NK cells kill malignant cells by antibody-dependent cell-mediated cytotoxicity (ADCC), a process by which the anti-CD16 arm binds to NK cells and the anti-B7-H3 arm binds to tumor targets thereby facilitating effector target interaction at the cancer site. ADCC functionality was confirmed using a Cr-51 release assay.

Binding of the Anti-CD16 Domain

To test the binding of the anti-CD16 domain, binding was evaluated on canine peripheral blood mononuclear cells (PBMC) that contained canine NK cells, T cells, B cells, and monocytes (Table 2). A single batch of 1615B7H3 TriKE (SEQ ID NO:56) was directly labeled with FITC fluorochrome and tested. The binding of the anti-CD16 fragment alone (anti-CD16-FITC) was tested as a positive control. Binding of an anti-B7H3 fragment alone (antiB7H3-FITC) was tested as a negative control.

TABLE 2

Binding of the anti-CD16 domain of 1615B7H3 TriKE (SEQ ID NO: 56) to dog PBMC

| Protein | Lot Number | Protein Concentration | | |
|---|---|---|---|---|
| | | 2000 nM | 400 nM | 80 nM |
| Data for dog named "Maverick" PBMC | | | | |
| 1615B7H3 | SO022222 | 42.1 | 28.8 | 4.8 |
| 1615B7H3 | 063022 | 44.2 | 22.9 | 2.9 |
| anti-CD16 | SO090121 | 43.6 | 26.5 | 10.1 |
| CD3IL15B7H3 | AS061422 | 31.4 | 9.2 | 1.1 |
| Data for dog named "Freya" PBMC | | | | |
| 1615B7H3 | 063022 | 29.9 | 10.5 | 3.1 |
| anti-CD16 | SO090121 | 27.9 | 16.7 | 9.9 |
| canine IL15 | SO061417 | 0.9 | 0.2 | 0.03 |
| anti-B7H3 | SO121418 | 0.9 | 0.4 | 0.1 |
| Data for dog named "Ripley" PBMC | | | | |
| 1615B7H3 | 063022 | 19.5 | 5.6 | 0.6 |
| anti-CD16 | SO090121 | 16.1 | 11.2 | 2.8 |
| canine IL15 | SO061417 | 0.5 | 0.1 | 0.1 |
| anti-B7H3 | SO121418 | 0.7 | 0.2 | 0.1 |
| Data for dog named Never PBMC | | | | |
| 1615B7H3 | SO022222 | 35.1 | 12.8 | 1.3 |
| 1615B7H3 | 063022 | 32.6 | 8.2 | 1.2 |
| anti-CD16 | SO090121 | 23.8 | 8.8 | 3.7 |
| CD3IL15B7H3 | AS061422 | 29.5 | 6.1 | 0.8 |
| IL-15 Treated PBMC for 6 days* | | | | |
| 1615B7H3 | SO022222 | 41.8 | 20.1 | 8.4 |
| 1615B7H3 | 063022 | 40.6 | 21.9 | 5.0 |
| anti-CD16 | O090121 | 35.8 | 15.3 | 6.2 |
| CD3IL15B7H3 | AS061422 | 35.9 | 16.1 | 6.2 |

*PBMC Treated with IL-15 = 20 ng/ml canine IL15 + 100 ng/ml human IL15 for six days The data indicate that 1615B7H3 TriKE 063022 (SEQ ID NO:56) bound well, comparable to the reference TriKE S0022222 and the anti-canine CD16 antibody fragment alone. Since B7H3 is not expressed on lymphocytes, and the anti-canine CD16 antibody fragment alone bound, the data demonstrate that the binding capability of the anti-canine CD16 antibody moiety of the TriKE is intact.

Binding of the Anti-B7-H3 Moiety

To test binding of the anti-B7H3 moiety, binding was evaluated on B7H3 expressing canine osteosarcoma OSCA78 cells (Table 3).

TABLE 3

Binding anti-B7-H3 moiety to B7-H3 expressing OSCA78 Cells

EXPERIMENT 1

| Protein | Lot Number | Protein Concentration | | |
|---|---|---|---|---|
| | | 2000 nM | 400 nM | 80 nM |
| 1615B7H3 | 101222 | 100.0 | 99.2 | 74.2 |
| BAC3 | SO070816 | 4.1 | 1.5 | 0.7 |
| anti-B7H3 | SO070122 | 99.8 | 98.8 | 64.0 |
| 1615B7H3 | 63022 | 99.9 | 99.3 | 59.3 |

EXPERIMENT 2

| Protein | Lot Number | Protein Concentration | | |
|---|---|---|---|---|
| | | 400 nM | 80 nM | 16 nM |
| 1615B7H3 | SO022222 | 95.3 | 56.0 | 2.5 |
| 1615CAMB7H3 | 063022 | 96.6 | 46.1 | 2.1 |
| anti-CD16 | SO090121 | 5.1 | 1.6 | 1.0 |
| BAC3 | SO070816 | 6.0 | 1.8 | 0.9 |
| anti-B7H3 | SO070122 | 93.7 | 42.1 | 2.8 |
| CD315B7H3 | AS061422 | 99.5 | 94.2 | 23.5 |

The data indicate that TriKE batch 063022, positive control batch 101222, and the anti-B7H3 antibody fragment alone bind to the B7-H3 expressing osteosarcoma cell line OSCA78. BAC3, and the anti-CD16 antibody fragment were negative controls and did not bind well. BAC3 contains an anti-T cell receptor antibody fragment. Since CD16 is not expressed on OSCA-78 cells, and the anti-B7H3 fragment alone bound, the data demonstrate that the binding capability of the anti-B7H3 moiety of the TriKE is intact.

Functionality of the IL-15 Moiety

Figure 13:
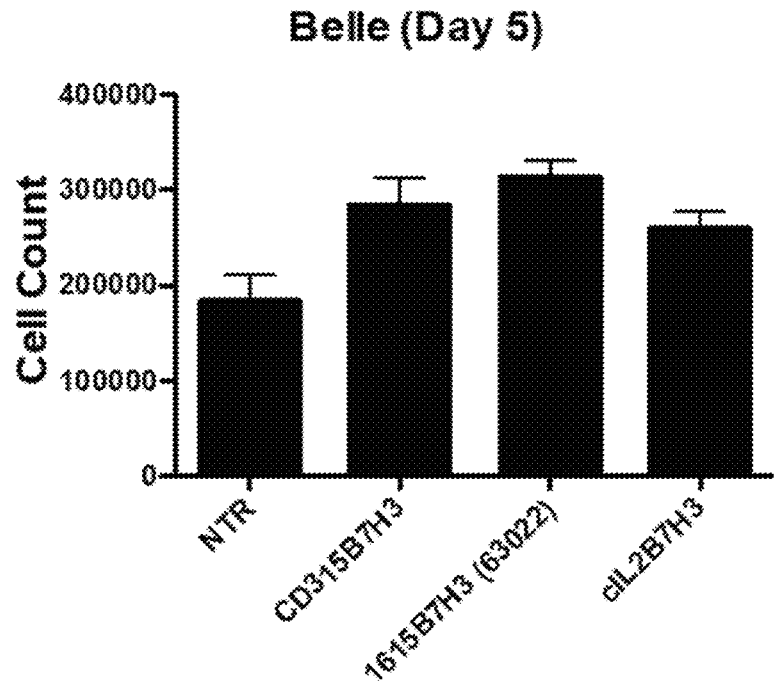
FIG. 13. Trypan blue viability assay to test in vitro lymphocyte cell expansion ability. (A) Data for PBMCs obtained from a dog named Belle. (B) Data for PBMCs obtained from a dog named Yankee 5 days after drug exposure. The 1615B7H3 TriKE (SEQ ID NO:56) compound enhanced lymphocyte expansion.
Figure 13:
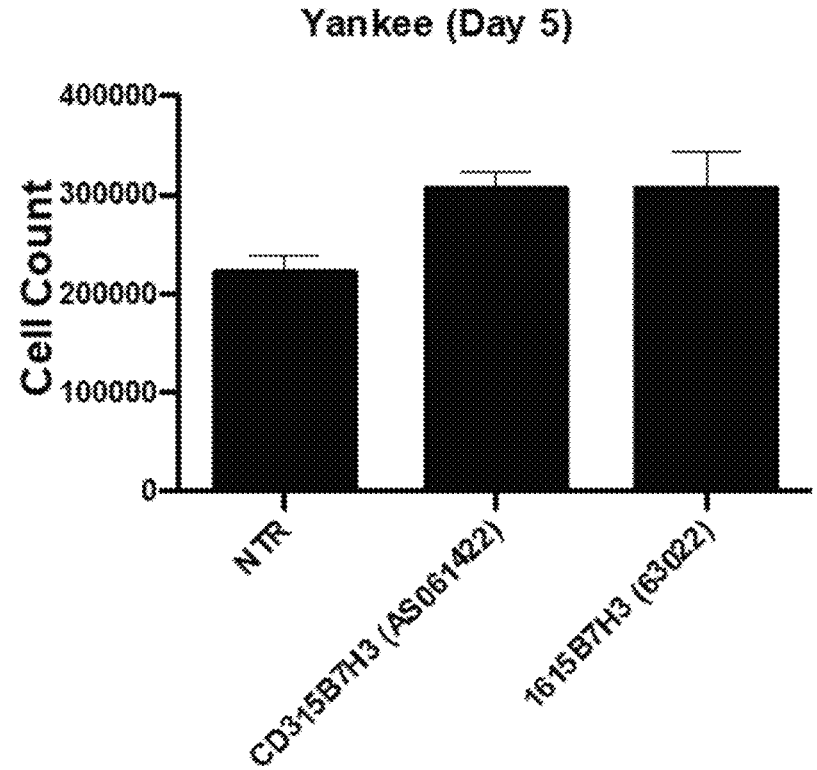

TriKE compounds induce NK expansion. In order to test the ability of the IL-15 moiety to stimulate lymphocytes to proliferate, a trypan blue viability assay was used in which TriKE-treated dog blood samples were evaluated for their in vitro expansion ability. PBMCs from two dogs were separately treated with the clinical 1615B7H3 TriKE (batch 063022; SEQ ID NO:56) or a positive control, either CD3IL15B7H3 or cIL2B7H3. Cellular expansion was observed compared to the no treatment control group when cells were cultured for five days, stained with a vital stain, and then counted. FIG. 13 shows that the clinical TriKE enhanced levels of lymphocytes from the dog named Belle and the dog named Yankee five days after drug exposure.

Toxicity Testing

A toxicity was performed, in which test groups of mice were injected with TriKE and then evaluated for weight loss, changes in liver and kidney enzymes, and pathologic changes (looking for lymphocyte infiltration and any damage to organs) at the end the one-month study. The mice were injected intraperitoneally three times (MWF) per week for 21 days.

Figure 14:
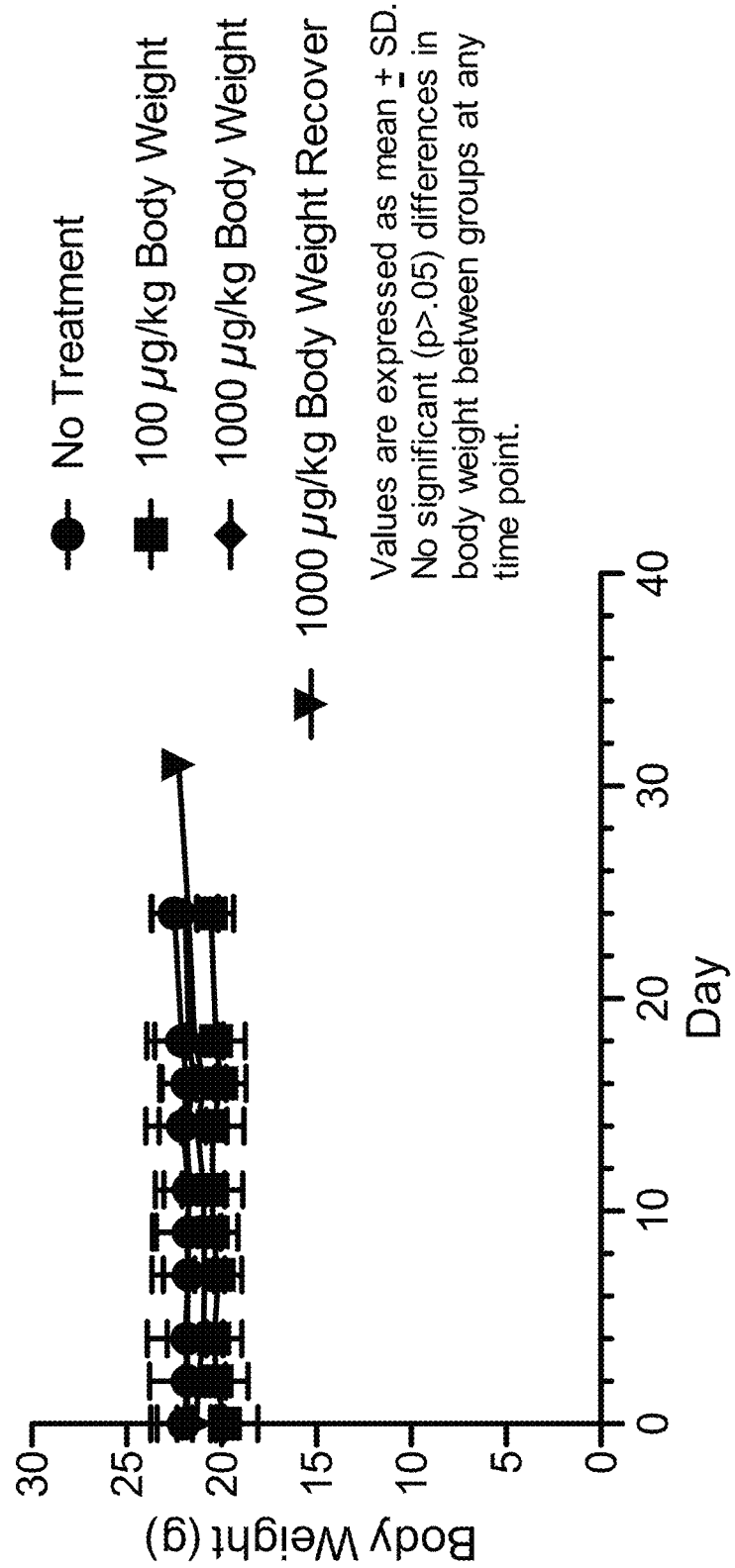
FIG. 14. Body weight of mice treated with low-dose 100 μg/kg TriKE, high dose 1000 μg/kg, or high dose 1000 μg/kg given a week to recover.
Figure 15:
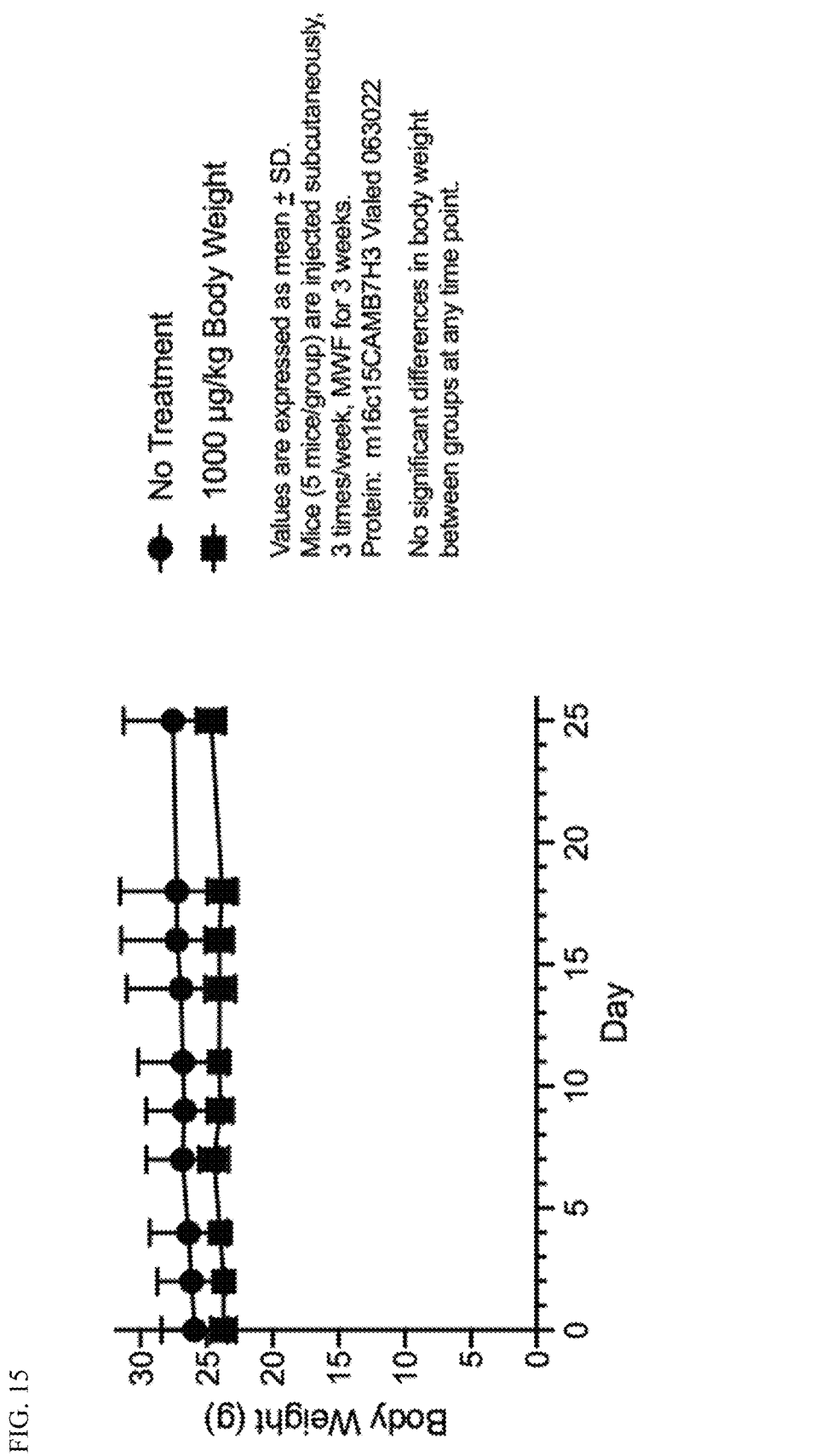
FIG. 15. Groups of BALB/c mice (n=6/group) were given high dose 1000 μg/kg TriKE subcutaneously or control PBS. Animals were weighed over a month period.

Treatment groups (6 BALB/c female mice/group) were:
1. Group 1—No treatment
2. Group 2—Medium dose (100 μg/kg body weight of protein)
3. Group 3—High dose (1000 μg/kg body weight of protein)
4. Group 4—High dose recovery (1000 μg/kg body weight of protein) with one week of recovery before sacrifice Weight Loss Mice in Groups 1-3 were sacrificed on days 28-30 and serum collected for enzyme analysis and organs collected for pathology study. Mice in Group 4 were sacrificed a week after Groups 1-3 mice in order to determine if any lost weight was recovered. No injections were administered in that last week. FIG. 14 shows that no weight loss occurred over the entire course of experiment in any treatment group.

Organ Enzymes

Next, kidney enzymes (BUNN, creatinine) and liver enzymes (ALT, AST) enzymes were tested. Table 4 shows minimal change in enzymes in Groups 1-3. But the high dose recovery Group 4 showed elevated liver enzymes. A pathology study revealed only minimal damage to liver tissues in the Group 4 mice.

TABLE 4

Mean and SD serum biochemistry data** across the four treatment groups.

| Group | BUN (mg/dL) | | Creatinine (mg/dL) | | ALT (U/L) | | AST (U/L) | |
|---|---|---|---|---|---|---|---|---|
| | Mean | SD | Mean | SD | Mean | SD | Mean | SD |
| 1 | 18.7 | 2.3 | <0.2 | 0.0 | 33.2 | 5.6 | 224.5 | 97.9 |
| 2 | 18.8 | 1.2 | <0.2 | 0.0 | 33.0 | 3.5 | 193.5 | 46.1 |
| 3 | 17.0 | 0.6 | <0.2 | 0.0 | 30.7 | 3.9 | 202.0 | 68.2 |
| 4 | 23.8 | 1.9 | <0.2 | 0.0 | 580.5 | 258.7 | 783.5 | 314.1 |

Group 1 = No Treatment
Group 2 = 100 μg/kg treatment
Group 3 = 1000 μg/kg treatment
Group 4 = 1000 μg/kg treatment + Recovery
**Data generated using a Beckman Coulter AU40 automated spectrophotometric chemistry analyzer.

Subcutaneous TriKE Delivery

Subcutaneous (SQ) administration of the TriKE compound was evaluated as an alternative to continuous intravenous infusion, which is the present norm is extremely hard on patients. A weight loss study was undertaken with SQ administration in mice. Mice were injected subcutaneously with 1000 μg/kg body weight 1615B7H3 TriKE (063022; SEQ ID NO:56) three times per week (MWF) for three weeks.

No significant differences in body weight between experimental and control groups were observed at any time point.

ADCC Killing Assay

Figure 16:
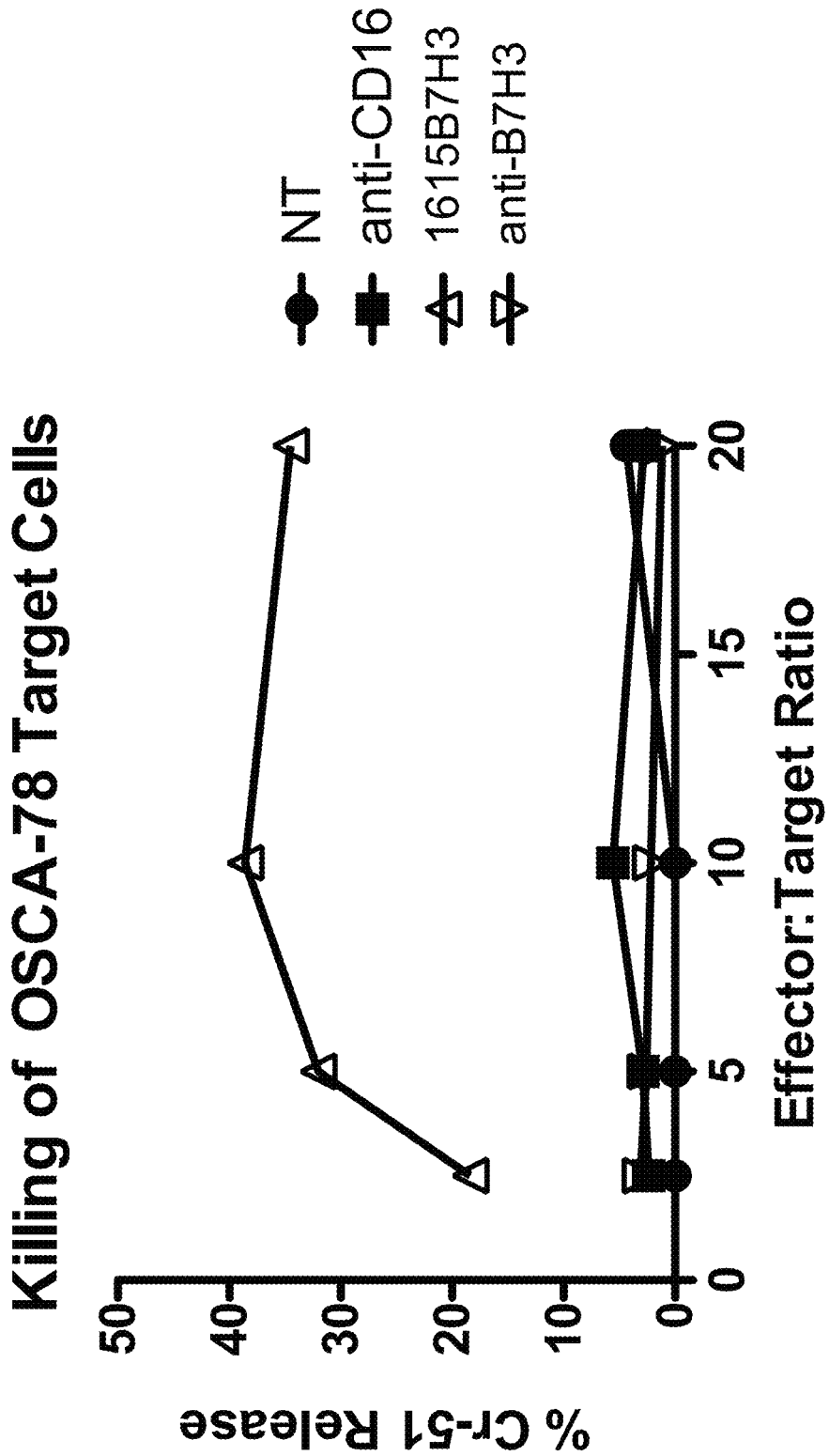
FIG. 16. Increasing numbers of canine PBMC were incubated with $^{51}$Cr labeled target cells for four hours, centrifuged, and then the supernatant was measured for released isotope.

To test the ability of the 1615B7H3TriKE (SEQ ID NO:56) to kill via antibody-dependent cellular cytotoxicity (ADCC), a conventional $^{51}Cr$ release assay was used. $^{51}Cr$ B7-H3 expressing OSCA78 target tumor cells were incubated with canine PBMC and then radioactivity released by the lysed target cells was quantitated. FIG. 16 shows that only the TriKE displayed the ability to lyse and cause release of the isotope. Controls were all negative.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

```
Sequence Listing Free Text
human CD16A
                                                                    SEQ ID NO: 1
MWQLLLPTAL LLLVSAGMRT EDLPKAVVFL EPQWYRVLEK DSVTLKCQGA YSPEDNSTQW

FHNESLISSQ ASSYFIDAAT VDDSGEYRCQ TNLSTLSDPV QLEVHIGWLL LQAPRWVFKE

EDPIHLRCHS WKNTALHKVT YLQNGKGRKY FHHNSDFYIP KATLKDSGSY FCRGLFGSKN

VSSETVNITI TQGLAVSTIS SFFPPGYQVS FCLVMVLLFA VDTGLYFSVK TNIRSSTRDW

KDHKFKWRKD PQDK canine CD16A
                                                                    SEQ ID NO: 2
MWQLVSSTAL LLLVSAGTQA DVPKAVVVLE PKWNRVLTMD SVTLKCQGDH LLRDNYTWLH

NGRPISNQIS TYIIKNASIK NSGEYRCQTD QSKLSDPVQL EVHTGWLLLQ VPRLVFQEGE

LIQLKCHSWK NTPVRNVQYF QNGRGKKFFY NNSEYHIPAA TSEHNGSYFC RGIIGKKNES

SEAVNIIIQG SSLPSTSLLL SHWPQIPFSL VMALLFAVDT GLYFAVQRDL RSSMGNLKNS

KVIWSQGS human CD64
                                                                    SEQ ID NO: 3
MWFLTTLLLW VPVDGQVDTT KAVISLQPPW VSVFQEETVT LHCEVLHLPG SSSTQWFLNG

TATQTSTPSY RITSASVNDS GEYRCQRGLS GRSDPIQLEI HRGWLLLQVS SRVFTEGEPL

ALRCHAWKDK LVYNVLYYRN GKAFKFFHWN SNLTILKTNI SHNGTYHCSG MGKHRYTSAG

ISVTVKELFP APVLNASVTS PLLEGNLVTL SCETKLLLQR PGLQLYFSFY MGSKTLRGRN

TSSEYQILTA RREDSGLYWC EAATEDGNVL KRSPELELQV LGLQLPTPVW FHVLFYLAVG

IMFLVNTVLW VTIRKELKRK KKWDLEISLD SGHEKKVTSS LQEDRHLEEE LKCQEQK canine CD64
                                                                    SEQ ID NO: 4
MWLLTVLLLW VPAGAQTDPV KAVITLQPPW VSVFQEESVT LWCEGPHLPG DSSTQWFLNG

TATQTLTPRY RIAAASVNDN GEYRCQTGLS VLSDPIQLGI HRDWLILQVS GRVFTEGEPL

TLRCHGWNNK LVYNVLFYQN GTVLKFSPQN SEFTILKTTL HHNGIYHCSA MGKHRYESAG

VSITIKELFP APVLKASLSS PILEGHVVNL SCETKLLLQR PGLQLYFSFY MGSKTLLSRN

TSSEYQILTA KKEDSGLYWC EATTEDGNVV KRSPELELQV VGPQTLTPVW FHVLFYVAMG

MIFLVDTIFC MIIHKELQRK KKWNLEISLY SGLEKRVDSY LQKERDLEEP KYQELEQLQE

KTPQKPPEGE QQ anti-canine CD16 (clone 4A5) V_H
                                                                    SEQ ID NO: 5
MKCSWVIFFL MAVVIGINSE VQLQQSGAEL VRSGASVKLS CTASGFNIKD YYMHWVKQRP

EQGLEWIGWL DPENGDTVYA PKFQGRATMT ADTSSNTAYL HLSSLTSEDT AVYYCNALVY

SLLGQDYWGQ GTTLTVSSAK TTPPSVYPLA PGSAAQTNSM VTLGCLVKGY FPEPVTVTWN

SGSLSSGVHT FPAVLQSDLY TLSSSVTVPS S
```

```
anti-canine CD16 (clone 4A5) V_H CDR1
                                                         SEQ ID NO: 6
GFNIKDYY anti-canine CD16 (clone 4A5) V_H CDR2
                                                         SEQ ID NO: 7
LDPENGDT anti-canine CD16 (clone 4A5) V_H CDR3
                                                         SEQ ID NO: 8
NALVYSLLGQDY anti-canine CD16 (clone 4A5) V_L
                                                         SEQ ID NO: 9
MDFQVQIFSF LLISASVIMS RGQILLTQSP AIMSASPGEK VTMTCSASSS VGYMHWYQQK

PGSSPKPWIY DTSDLASGFP ARFSGSRSGT SYSLIISSME AEDAATYYCH QRSFYPYTFG

GGTKLEIKRA DAAPTVSIFP PSSEQLTSGG ASVVCFLNNF YPKDINVKWK IDGSERQNGV

LNSWTDQDSK DSTYSMSSTL TLTK anti-canine CD16 (clone 4A5) V_L CDR1
                                                         SEQ ID NO: 10
SSVGY anti-canine CD16 (clone 4A5) V_L CDR2
                                                         SEQ ID NO: 11
DTS anti-canine CD16 (clone 4A5) V_L CDR3
                                                         SEQ ID NO: 12
HQRSFYPYT anti-canine CD64 (clone 10) V_H
                                                         SEQ ID NO: 13
QVQLQQSGAE LVRPGASVTL SCKASGYTFI DFEIHWVKQT PVHGLEWIGA IDPETGGTAY

NQKFKGKATL TADKSSSAAY MELRSLTSED SAVYYCTRRA TVVGSDYWGQ GTTLTVSS anti-canine CD64 (clone 10) V_H CDR1
                                                         SEQ ID NO: 14
DFEIH anti-canine CD64 (clone 10) V_H CDR2
                                                         SEQ ID NO: 15
AIDPETGGTA YNQKFKGKAT anti-canine CD64 (clone 10) V_H CDR3
                                                         SEQ ID NO: 16
RATVVGSDY anti-canine CD64 (clone 10) V_L
                                                         SEQ ID NO: 17
DIVMTQSHKF MSTSVGDRVS IACKASQDVG AAVAWYHQKP GQSPKLLIYW ASTRHTGVPD

RFTGSGSGTD STLTISTVQS EDLAEYFCQQ YSSYPFTFGS GTKLEIK anti-canine CD64 (clone 10) V_L CDR1
                                                         SEQ ID NO: 18
KASQDVGAAV A anti-canine CD64 (clone 10) V_L CDR2
                                                         SEQ ID NO: 19
WASTRHT anti-canine CD64 (clone 10) V_L CDR3
                                                         SEQ ID NO: 20
QQ YSSYPFT linking segment
                                                         SEQ ID NO: 33
GGGGSGGGGS GGGGS linking segment
                                                         SEQ ID NO: 34
GSTSGSGKPG SGEGSTKG
```

-continued linking segment
SEQ ID NO: 35
PSGQAGAAAS ESLFVSNHAY linking segment
SEQ ID NO: 36
EASGGPE linking segment
SEQ ID NO: 37
AEAAKEAAKE AAKEAAKALE AEAAKEAAKE AAKEAAKA linking segment
SEQ ID NO: 38
AEAAKEAAKA linking segment
SEQ ID NO: 39
SGGGGSGGGGS GGGGSGGGGSG linking segment
SEQ ID NO: 40
GGGGSGGGGS linking segment
SEQ ID NO: 41
GSTSGSGKPG SGEGSTKG linking segment
SEQ ID NO: 42
EPKSSDKTHT SPPSP linking segment
SEQ ID NO: 43
RATPSHNSHQ VPSAGGPTAN SGTSG linking segment
SEQ ID NO: 44
SSGGGGSGGG GGGSSRSSL IL-12A
SEQ ID NO: 45
RNLPVATPDP GMFPCLHHSQ NLLRAVSNML QKARQTLEFY PCTSEEIDHE DITKDKTSTV

EACLPLELTK NESCLNSRET SFITNGSCLA SRKTSFMMAL CLSSIYEDLK MYQVEFKTMN

AKLLMDPKRQ IFLDQNMLAV IDELMQALNF NSETVPQKSS LEEPDFYKTK IKLCILLHAF

RIRAVTIDRV MSYLNAS

IL-12B
SEQ ID NO: 46
IWELKKDVYV VELDWYPDAP GEMVVLTCDT PEEDGITWTL DQSSEVLGSG KTLTIQVKEF

GDAGQYTCHK GGEVLSHSLL LLHKKEDGIW STDILKDQKE PKNKTFLRCE AKNYSGRFTC

WWLTTISTDL TFSVKSSRGS SDPQGVTCGA ATLSAERVRG DNKEYEYSVE CQEDSACPAA

EESLPIEVMV DAVHKLKYEN YTSSFFIRDI IKPDPPKNLQ LKPLKNSRQV EVSWEYPDTW

STPHSYFSLT FCVQVQGKSK REKKDRVFTD KTSATVICRK NASISVRAQD RYYSSSWSEW

ASVPCS human IL-15
SEQ ID NO: 47
NWVNVISDLK KIEDLIQSMH IDATLYTESD VHPSCKVTAM KCFLLELQVI SLESGDASIH

DTVENLIILA NNSLSSNGNV TESGCKECEE LEEKNIKEFL QSFVHIVQMF INTS primer
SEQ ID NO: 48
CTCTAGACTG CCGGATCCGC AGTGACTTGC TGACCCTAAT GTG primer
SEQ ID NO: 49
TCGAATTTAA ATGGATCCAG AGAGGTCCAG AGGGGTTGCT TT -continued primer
SEQ ID NO: 50
GCCCAGCCGG CCAGATCTAC ACAAGCTGCA GATGTCCCA primer
SEQ ID NO: 51
GCGGATCCCG GGAGATCTAG AGAGGTCCAG AGGGGTTGCT TT primer
SEQ ID NO: 52
TCTAGACTGC CGGATCCACT AGTAACGGCC GCCAGTGT primer
SEQ ID NO: 53
TCGAATTTAA ATGGATCCAG AGAGGTCCAG AGGGGTTGCT TT primer
SEQ ID NO: 54
TCTAGACTGC CGGATCCGGA GATAACATGT GGCTCTTGAC AGTTCTA primer
SEQ ID NO: 55
TCGAATTTAA ATGGATCCAA AAAGAAGTGG GAGGCACCAT C 1615B7H3
SEQ ID NO: 56
MEQILLTQSP AIMSASPGEK VTMTCSASSS VGYMHWYQQK PGSSPKPWIY DTSDLASGFP

ARFSGSRSGT SYSLIISSME AEDAATYYCH QRSFYPYTFG GGTKLEIKGG GGSGGGGSGG

GGSEVQLQQS GAELVRSGAS VKLSCTASGF NIKDYYMHWV KQRPEQGLEW IGWLDPENGD

TVYAPKFQGR ATMTADTSSN TAYLHLSSLT SEDTAVYYCN ALVYSLLGQD YWGQGTTLTV

SSPSGQAGAA ASESLFVSNH AYNWQDVILD LEKIDNLIQS IHMDATLYTE SDVHPSCKVT

AMKCFLLELG VISLESGSHP IKEAVENLII LANSDLSSKG NITETGCKEC EELEEKSIKE

FLQSFVHIVQ MFINSSEASG GPEQVQLVES GGGLVQPGGS LRLSCAASGF TFSSYWMYWV

RQTPGKGLEW VSTINRDGSA TWYADSVKGR FTISRDNAKN TGYLQMNSLK PDDTAVYYCV

SDPDNYSSDE MVPYWGQGTQ VTVSS
amino acids 1-108: anti-canine CD16 V$_L$
amino acids 109-123: linker segment
amino acids 124-242: anti-canine CD16 V$_H$
amino acids 243-262: linker segment
amino acids 263-376: canine IL15
amino acids 377-383: linker segment
amino acids 384-505: anti-B7H3

1615CD20
SEQ ID NO: 57
MEQILLTQSP AIMSASPGEK VTMTCSASSS VGYMHWYQQK PGSSPKPWIY DTSDLASGFP

ARFSGSRSGT SYSLIISSME AEDAATYYCH QRSFYPYTFG GGTKLEIKGG GGSGGGGSGG

GGSEVQLQQS GAELVRSGAS VKLSCTASGF NIKDYYMHWV KQRPEQGLEW IGWLDPENGD

TVYAPKFQGR ATMTADTSSN TAYLHLSSLT SEDTAVYYCN ALVYSLLGQD YWGQGTTLTV

SSPSGQAGAA ASESLFVSNH AYNWQDVILD LEKIDNLIQS IHMDATLYTE SDVHPSCKVT

AMKCFLLELG VISLESGSHP IKEAVENLII LANSDLSSKG NITETGCKEC EELEEKSIKE

FLQSFVHIVQ MFINSSEASG GPEGTDIVMT QPPAIMSASP GEKVTMTCSA SSSVSYMHWY

QQKSGTSPKR WIYDTSKLAS GVPDRFSSSG SGTDFTLRIS RVEAEDVGVY YCAQNLELPF

TFGGGTKLEI KSSGGGGSGG GGGGSSRSSL EVNVVESGGG LVQPGDSLRL SCATSGFTFD

YFMSWVRQPP GKSLEWLGLI RNKVNGYTAE YSASVKGRFT ISRDNSRGIL YLQMYTLRAE

DSATYYCVRA STGTSFVYWG QGTLVTVSA
amino acids 1-108: anti-canine CD16 V$_L$
amino acids 109-123: linker segment
amino acids 124-242: anti-canine CD16 V$_H$ -continued amino acids 243-262: linker segment
amino acids 263-376: canine IL15
amino acids 377-383: linker segment
amino acids 384-629: anti-CD20 scFv

What is claimed is:

1. An anti-canine CD16 polypeptide comprising SEQ ID NO: 6, SEQ ID NO:7, SEQ ID NO:8, SEQ ID NO:10, DTS, and SEQ ID NO:12.

2. An anti-canine CD64 polypeptide comprising SEQ ID NO: 14, SEQ ID NO: 15, SEQ ID NO: 16, SEQ ID NO: 18, SEQ ID NO: 19, and SEQ ID NO: 20.

3. A multispecific compound comprising:
a targeting domain that selectively binds to:
    a target cell; or
    a target antigen expressed by a target cell; and
an immune cell engaging domain operably linked to the targeting domain, the immune cell engaging domain comprising an anti-canine CD16 polypeptide, the anti-canine CD16 polypeptide comprising SEQ ID NO:6, SEQ ID NO:7, SEQ ID NO:8, SEQ ID NO:10, DTS, and SEQ ID NO:12.

4. The multispecific compound of claim 3, wherein the immune cell engaging domain comprises an scFv, a F(ab)$_2$, or a Fab.

5. The multispecific compound of claim 3, wherein the targeting domain and the immune cell engaging domain are linked by a linking segment comprising any one of SEQ ID NOs: 33-44.

6. The multispecific compound of claim 3, further comprising an immune cell activating domain.

7. The multispecific compound of claim 6, wherein the immune cell activating domain is linked to either the targeting domain or the immune cell engaging domain by a linking segment comprising any one of SEQ ID NOs: 33-44.

8. The multispecific compound of claim 3, wherein the targeting domain specifically binds to a tumor antigen.

9. A multispecific compound comprising:
a targeting domain that selectively binds to:
    a target cell; or
    a target antigen expressed by a target cell; and
an immune cell engaging domain operably linked to the targeting domain, the immune cell engaging domain comprising an anti-canine CD64 polypeptide, the anti-canine CD64 polypeptide comprising SEQ ID NO: 14, SEQ ID NO: 15, SEQ ID NO: 16, SEQ ID NO: 18, SEQ ID NO: 19, and SEQ ID NO:20 .

10. The multispecific compound of claim 9, wherein the immune cell engaging domain comprises an scFv, a F(ab)$_2$, or a Fab.

11. The multispecific compound of claim 9, wherein the targeting domain and the immune cell engaging domain are linked by a linking segment comprising any one of SEQ ID NOs: 33-44.

12. The multispecific compound of claim 9, further comprising an immune cell activating domain.

13. The multispecific compound of claim 12, wherein the immune cell activating domain is linked to either the targeting domain or the immune cell engaging domain by a linking segment comprising any one of SEQ ID NOs: 33-44.

14. The multispecific compound of claim 9, wherein the targeting domain specifically binds to a tumor antigen.

15. A targeted imaging compound comprising:
a targeting domain comprising the anti-canine CD16 polypeptide of claim 1; and
an imaging domain linked to the targeting domain.

16. The targeted imaging compound of claim 15, wherein the imaging domain comprises a colorimetric label, a fluorescent label, a radioactive label, a magnetic label, or an enzymatic label.

17. A targeted imaging compound comprising:
   a targeting domain comprising the anti-canine CD64 polypeptide of claim 2; and
   an imaging domain linked to the targeting domain.

18. The targeted imaging compound of claim 17, wherein the imaging domain comprises a colorimetric label, a fluorescent label, a radioactive label, a magnetic label, or an enzymatic label.

19. A capture assay device comprising the anti-canine CD16 polypeptide of claim 1 immobilized to a substrate.

20. A capture assay device comprising the anti-canine CD64 polypeptide of claim 2 immobilized to a substrate.

* * * * *

UNITED STATES PATENT AND TRADEMARK OFFICE
CERTIFICATE OF CORRECTION

PATENT NO. : 12,269,887 B2  
APPLICATION NO. : 18/099448  
DATED : April 8, 2025  
INVENTOR(S) : Bruce K. Walcheck et al.

Page 1 of 1

It is certified that error appears in the above-identified patent and that said Letters Patent is hereby corrected as shown below:

In the Claims

In Column 57, Line 40 (Claim 1): the term 'DTS' should read --SEQ ID NO:11--.

In Column 57, Line 53 (Claim 3): the term 'DTS' should read --SEQ ID NO:11--.

Signed and Sealed this  
Twenty-fourth Day of June, 2025

Coke Morgan Stewart  
*Acting Director of the United States Patent and Trademark Office*